(12) United States Patent
Diaz et al.

(10) Patent No.: US 9,963,439 B2
(45) Date of Patent: May 8, 2018

(54) SPECIFIC INHIBITORS OF CYTOCHROME P450 26 RETINOIC ACID HYDROXYLASE

(71) Applicants: University of Washington Through its Center for Commercialization, Seattle, WA (US); UNIVERSITY OF MONTANA, Missoula, MT (US)

(72) Inventors: Philippe Diaz, Missoula, MT (US); Nina Isoherranen, Seattle, WA (US); Brian Buttrick, Seattle, WA (US); Nicolas Guilloteau, Missoula, MT (US)

(73) Assignees: University of Washington Through Its Center For Commercialization, Seattle, WA (US); University of Montana, Missoula, MT (US)

( * ) Notice: Subject to any disclaimer, the term of this patent is extended or adjusted under 35 U.S.C. 154(b) by 0 days. days.

(21) Appl. No.: 14/912,479

(22) PCT Filed: Aug. 20, 2014

(86) PCT No.: PCT/US2014/051962
§ 371 (c)(1),
(2) Date: Feb. 17, 2016

(87) PCT Pub. No.: WO2015/026990
PCT Pub. Date: Feb. 26, 2015

(65) Prior Publication Data
US 2016/0200703 A1   Jul. 14, 2016

Related U.S. Application Data

(60) Provisional application No. 61/867,892, filed on Aug. 20, 2013.

(51) Int. Cl.
*C07D 317/30* (2006.01)
*C07C 69/738* (2006.01)
(Continued)

(52) U.S. Cl.
CPC ............ *C07D 317/30* (2013.01); *C07C 57/50* (2013.01); *C07C 59/54* (2013.01); *C07C 59/72* (2013.01);
(Continued)

(58) Field of Classification Search
USPC ................. 514/440, 444, 445, 452
See application file for complete search history.

(56) References Cited

U.S. PATENT DOCUMENTS 4,814,454 A   3/1989 Misra
4,826,969 A   5/1989 Maignan et al.
(Continued)

FOREIGN PATENT DOCUMENTS

CN   102503857   6/2012
EP   0722928 A1   7/1996
(Continued)

OTHER PUBLICATIONS

Ohta (Biorganic and Medicinal Chemistry Letters; 23, 2013, 81-84; available online Nov. 15, 2012).*
(Continued)

*Primary Examiner* — Pancham Bakshi
(74) *Attorney, Agent, or Firm* — McDonnell Boehnen Hulbert & Berghoff LLP

(57) ABSTRACT

The present disclosure is generally directed to compositions and methods for treating diseases that are ameliorated by the inhibition of CYP26 mediated retinoic acid metabolism. The compositions comprise compounds of formula (I). A rep-reid50000060307390 IB/345 nullsents aryl optionally substituted with one, two, three, or four groups that are each independently halogen, cyano, nitro, $C_{1-6}$ alkyl, $C_{1-6}$ haloalkyl, $-NH_2$, $-NH(C_1-C_6$ alkyl), $-N(C_1-C_6$ alkyl$)_2$, $-OH$, $C_1$-$C_6$ alkoxy, and $C_1$-$C_6$ haloalkoxy; X is a bond, $-CH_2-$, $-CHR^5-$, $-C=CHR^4-$, $-NR^4-$, $-N=O-R^4-$, $-O-$, $-S-$, $-SO-$, $-SO_2-$, $-C(O)-$, or $-C(NR^4)-$, or X is of formula (a), (b) or (c), wherein each n is independently 1, 2, or 3; each $R^4$ is independently hydrogen or $C_{1-6}$ alkyl; $R^5$ is independently hydrogen, $C_{1-6}$ alkyl, or $-OR^6$, where $R^6$ is selected from the group consisting of hydrogen, $C_{1-6}$ alkyl, $C_{2-6}$ alkenyl, $C_{2-6}$ alkynyL $C_{3-12}$ cycloalkyl, heterocyclyl, aryl, aryl$C_{1-6}$ alkyl, heteroaryl, or heteroaryl$C_{1-6}$ alkyl; Y is $C_{1-6}$ alkylene, $C_{2-6}$ alkenylene, or $C_{2-6}$ alkylylene moiety.

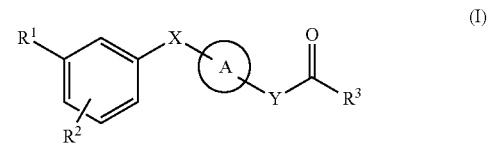

(I)

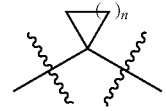

(a)

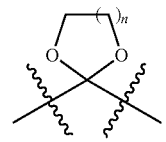

(b)

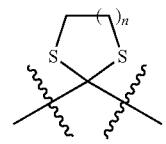

(c)

53 Claims, 4 Drawing Sheets

(51) Int. Cl.
| | |
|---|---|
| C07C 323/65 | (2006.01) |
| C07C 69/616 | (2006.01) |
| C07C 69/73 | (2006.01) |
| C07C 69/734 | (2006.01) |
| C07D 339/06 | (2006.01) |
| C07C 317/44 | (2006.01) |
| C07C 323/62 | (2006.01) |
| C07C 229/42 | (2006.01) |
| C07C 229/44 | (2006.01) |
| C07C 57/50 | (2006.01) |
| C07C 59/54 | (2006.01) |
| C07C 59/72 | (2006.01) |
| C07C 59/86 | (2006.01) |

(52) U.S. Cl.
CPC ............ *C07C 59/86* (2013.01); *C07C 69/616* (2013.01); *C07C 69/73* (2013.01); *C07C 69/734* (2013.01); *C07C 69/738* (2013.01); *C07C 229/42* (2013.01); *C07C 229/44* (2013.01); *C07C 317/44* (2013.01); *C07C 323/62* (2013.01); *C07C 323/65* (2013.01); *C07D 339/06* (2013.01); C07C 2602/10 (2017.05); C07C 2602/28 (2017.05); C07C 2603/74 (2017.05)

(56) References Cited

U.S. PATENT DOCUMENTS

| | | | |
|---|---|---|---|
| 4,829,080 | A | 5/1989 | Maignan et al. |
| 4,833,240 | A | 5/1989 | Maignan et al. |
| 5,023,363 | A | 6/1991 | Maignan et al. |
| 5,128,479 | A | 7/1992 | Janssen et al. |
| 5,556,844 | A | 9/1996 | Reichert et al. |
| 6,258,775 | B1* | 7/2001 | Bernardon ............... C07C 45/46 424/70.1 |
| 6,291,677 | B1 | 9/2001 | Vasudevan et al. |
| 6,300,350 | B1 | 10/2001 | Belloni et al. |
| 6,653,322 | B1 | 11/2003 | Chambon et al. |
| 7,560,589 | B2 | 7/2009 | Britton et al. |
| 7,569,601 | B2 | 8/2009 | Fang et al. |
| 7,964,639 | B2 | 6/2011 | DeLuca et al. |
| 2002/0049250 | A1 | 4/2002 | Maignan et al. |
| 2006/0122282 | A1 | 6/2006 | Leonard |
| 2010/0330200 | A1* | 12/2010 | Carminati ............ A61K 31/192 424/649 |
| 2013/0164663 | A1* | 6/2013 | Hirose ................ G03G 15/0142 430/56 |
| 2014/0086909 | A1 | 3/2014 | Lu et al. |

FOREIGN PATENT DOCUMENTS

| | | |
|---|---|---|
| EP | 0915823 A1 | 5/1999 |
| EP | 2612665 A1 | 7/2013 |
| WO | 200145664 A2 | 6/2001 |
| WO | 2005108338 A1 | 11/2005 |
| WO | 2008025965 A2 | 3/2008 |
| WO | 2008086942 A2 | 7/2008 |
| WO | 2011055843 A1 | 5/2011 |
| WO | 2013040227 A2 | 3/2013 |
| WO | 2013071282 A1 | 5/2013 |
| WO | 2013104399 A1 | 7/2013 |
| WO | 2014016507 A1 | 1/2014 |

OTHER PUBLICATIONS

CAS Registry No. 941688-51-3 (retrieved on SciFinder Aug. 2016).
CAS Registry No. 94497-51-5 (retrieved on SciFinder Aug. 2016).
Cavazzini, et al., "Vitamin A metabolism in cultured somatic cells from rat testis," Molecular and Cellular Biochemistry, vol. 252, No. 1, pp. 165-171, 2003.

Chandraratna, "Rational design of receptor-selective retinoids," Journal of the American Academy of Dermatology, vol. 39, No. 4, Suppl Pt 2, pp. S124-S128, 1998.
Chapman, et al., "Use of captive spray ionization to increase throughput of the data-independent acquisition technique PAcIFIC," Rapid Communications in Mass Spectrometry, vol. 30, No. 9, pp. 1101-1107, 2016.
Charton, et al., "Novel non-carboxylic acid retinoids: 1,2,4-Oxadiazol-5-one derivatives," Bioorganic & Medicinal Chemistry Letters, vol. 19, 2, pp. 489-492, 2009.
Chen, et al., "Biological effects and metabolism of 9-cis-retinoic acid and its metabolite 9,13-di-cis-retinoic acid in HaCaT keratinocytes in vitro: comparison with all-trans-retinoic acid," Archives of Dermatological Research, vol. 292, No. 12, pp. 612-620, 2000.
Cheng, et al., "Voriconazole inhibition of vitamin A metabolism: are adverse events increased in cystic fibrosis patients?" Pediatric Pulmonology, vol. 45, No. 7, pp. 661-666, 2010.
Chiba, et al., "Distinct retinoid X receptor-retinoic acid receptor heterodimers are differentially involved in the control of expression of retinoid target genes in F9 embryonal carcinoma cells," Molecular and Cellular Biology, vol. 17, No. 6, pp. 3013-3020, 1997.
Christie, et al., "Synthesis and evaluation of synthetic retinoid derivatives as inducers of stem cell differentiation," Organic & Biomolecular Chemistry, vol. 6, No. 19, pp. 3497-3507, 2008.
Chung, et al., "Role of retinoid signaling in the regulation of spermatogenesis," Cytogenetic and Genome Research, 105(2-4):189-202, 2004.
Clarke, et al., "Retinoids: potential in cancer prevention and therapy," Expert Reviews in Molecular Medicine, vol. 6, No. 25, pp. 1-23, 2004.
Clugston et al., "Altered hepatic retinyl ester concentration and acyl composition in response to alcohol consumption," Biochimica et Biophysica Acta, vol. 1831, No. 7, pp. 1276-1286, 2013.
Cordoba, et al., "Hypercalcemia due to an interaction of all-trans retinoic acid (ATRA) and itraconazole therapy for acute promyelocytic leukemia successfully treated with zoledronic acid," European Journal of Clinical Pharmacology, vol. 64, No. 10, pp. 1031-1032, 2008.
Cramer, et al., "ApoE-directed therapeutics rapidly clear beta-amyloid and reverse deficits in AD mouse models," Science, vol. 335, No. 6075, pp. 1503-1506, 2012.
Dawson, "Treatment of progressive metastatic prostate cancer," Oncology, vol. 7, No. 5, pp. 17-24, 1993.
Dawson, et al., "An Adamantyl-Substituted Retinoid-Derived Molecule That Inhibits Cancer Cell Growth and Angiogenesis by Inducing Apoptosis and Binds to Small Heterodimer Partner Nuclear Receptor: Effects of Modifying Its Carboxylate Group on Apoptosis, Proliferation, and Protein-Tyrosine Phosphatase Activity," Journal of Medicinal Chemistry, vol. 50, No. 11, pp. 2622-2639, 2007.
Dawson, et al., "Apoptosis Induction in Cancer Cells by a Novel Analogue of 6-[3-(1-Adamantyl)-4-hydroxyphenyl]-2-naphthalenecarboxylic Acid Lacking Retinoid Receptor Transcriptional Activation Activity," Cancer Research, vol. 61, No. 12, pp. 4723-4730, 2001.
Dawson, et al., "Correlation of Retinoid Binding Affinity to Retinoic Acid Receptor a with Retinoid Inhibition of Growth of Estrogen Receptor-positive MCF-7 Mammary Carcinoma Cells," Cancer Research, vol. 55, No. 19, pp. 4446-4451, 1995.
De Coster, et al., "Experimental studies with liarozole (R75251): An antitumoral agent which inhibits retinoic acid breakdown," Journal of Steroid Biochemistry and Molecular Biology, vol. 43, No. 1-3, pp. 197-201, 1992.
Debruyne, et al., "Liarozole-a novel treatment approach for advanced prostate cancer: results of a large randomized trial versus cyproterone acetate. Liarozole Study Group," Urology, vol. 52, No. 1, pp. 72-81, 1998.
Denis, "Controversies in the management of localized and metastatic prostatic cancer," European Journal of Cancer, vol. 27, No. 3, pp. 333-341, 1991.

(56) References Cited

OTHER PUBLICATIONS

Denis, et al., "Early clinical experience with liarozole (Liazal) in patients with progressive prostate cancer," European Journal of Cancer, vol. 34, No. 4, pp. 469-475, 1998.
Dijkman, et al., "Antitumoral effects of liarozole in androgen-dependent and independent R3327-Dunning prostate adenocarcinomas," Journal of Urology, vol. 151, No. 1, pp. 217-222, 1994.
Dijkman, et al., "Liarozole (R75251) in hormone-resistant prostate cancer patients," Prostate, vol. 33, No. 1, pp. 26-31, 1997.
DiSepio et al., "Retinoic Acid Receptor-Nuclear Factor-Interleukin 6 Antagonism: A Novel Mechanism of Retinoid-Dependent Inhibition of a Keratinocyte Hyperproliferative Differentiation Marker," Journal of Biological Chemistry, vol. 272, No. 41, pp. 25555-25559, 1997.
DiSepio, et al., "New drugs in the treatment of psoriasis," Expert Opinion on Investigational Drugs, vol. 9, No. 1, pp. 79-93, 2005.
Dixon, et al., "Pseudotumor cerebri due to the potentiation of all-trans retinoic acid by voriconazole," Journal of the American Pharmacists Association, 50(6):742-744, 2010.
Dockx, et al., "Inhibition of the metabolism of endogenous retinoic acid as treatment for severe psoriasis: an open study with oral liarozole," British Journal of Dermatology, vol. 133, No. 3, pp. 426-432, 1995.
Dong et al., "Distinct roles for cellular retinoic acid-binding proteins I and II in regulating signaling by retinoic acid," Journal of Biological Chemistry, vol. 274, No. 34, pp. 23695-23698, 1999.
Donnelly, et al., "Antiproteases and retinoids for treatment of chronic obstructive pulmonary disease," Expert Opinion on Therapeutic Patents, vol. 13, No. 9, pp. 1345-1372, 2005.
Douguet, et al., "Quantitative structure-activity relationship studies of RAR α, β, γ retinoid agonists," Molecular Informatics, vol. 18, No. 2, pp. 107-123, 1999.
Duester, "Retinoic acid synthesis and signaling during early organogenesis," Cell, vol. 134, No. 6, pp. 921-931, 2008.
Eckhoff, et al., "Human plasma all-trans-, 13-cis- and 13-cis-4-oxoretinoic acid profiles during subchronic vitamin A supplementation: comparison to retinol and retinyl ester plasma levels," Journal of Nutrition, vol. 121, No. 7, pp. 1016-1025, 1991.
el Mansouri et al., "Time- and dose-dependent kinetics of all-trans-retinoic acid in rats after oral or intravenous administration(s)," Drug Metabolism and Disposition, vol. 23, No. 2, pp. 227-231, 1995.
Fields, et al., "Retinoids in biological control and cancer," Journal of Cellular Biochemistry, vol. 102, No. 4, pp. 886-898, 2007.
Fiorella, et al., "Expression of cellular retinoic acid binding protein (CRABP) in *Escherichia coli*. Characterization and evidence that holo-CRABP is a substrate in retinoic acid metabolism," Journal of Biological Chemistry, vol. 266, No. 25, pp. 16572-16579, 1991.
Fiorella, et al., "Microsomal retinoic acid metabolism. Effects of cellular retinoic acid-binding protein (type I) and C18-hydroxylation as an initial step," Journal of Biological Chemistry, vol. 269, No. 14, pp. 10538-10544, 1994.
Fitzgerald, et al., "Retinoic Acid Receptor α Expression Correlates with Retinoid-induced Growth Inhibition of Human Breast Cancer Cells Regardless of Estrogen Receptor Status," Cancer Research, vol. 57, No. 13, pp. 2642-2650, 1997.
Fujii et al., "Metabolic inactivation of retinoic acid by a novel P450 differentially expressed in developing mouse embryos," EMBO Journal, vol. 16, No. 14, pp. 4163-4173, 1997.
Fukuzawa, et al., "Palladium-Catalyzed Coupling Reaction of Diaryl Dichalcogenide with Aryl Bromide Leading to the Synthesis of Unsymmetrical Aryl Chalcogenide," Synlett, vol. 13, pp. 2145-2147, 2006.
Gambone, et al., "Unique Property of Some Synthetic Retinoids: Activatio of the Aryl Hydrocarbon Receptor Pathway," Molecular Pharmacology, vol. 61, No. 2, pp. 334-342, 2002.

Garattini, et al., "Retinoids as differentiating agents in oncology: a network of interactions with intracellular pathways as the basis for rational therapeutic combinations," Current Pharmaceutical Design, 13(13):1375-1400, 2007.
Gediya et al., "Improved synthesis of histone deacetylase inhibitors (HDIs) (MS-275 and CI-994) and inhibitory effects of HDIs alone or in combination with RAMBAs or retinoids on growth of human LNCaP prostate cancer cells and tumor xenografts," Bioorganic & Medicinal Chemistry, vol. 16, No. 6, pp. 3352-3360, 2008.
Gediya, "A new simple and high-yield synthesis of suberoylanilide hydroxamic acid and its inhibitory effect alone or in combination with retinoids on proliferation of human prostate cancer cells," J Med Chem, vol. 48, No. 15, pp. 5047-5051, 2005.
Geria, et al., "Talarozole, a selective inhibitor of P450-mediated all-trans retinoic acid for the treatment of psoriasis acne," Current Opinion in Investigational Drugs, vol. 9, No. 11, pp. 1228-1237, 2008.
Giltaire, et al., "The CYP26 inhibitor R115866 potentiates the effects of all-trans retinoic acid on cultured human epidermal keratinocytes," British Journal of Dermatology, vol. 160, No. 3, pp. 505-513, 2009.
Gluyas, et al., "Disila-analogues of the synthetic retinoids EC23 and TTNN: synthesis, structure and biological evaluation," Organic & Biomolecular Chemistry, vol. 10, No. 34, pp. 6914-6929, 2012.
Godbole, et al., "Autophagy inhibition synergistically enhances anticancer efficacy of RAMBA, VN/12-1 in SKBR-3 cells, and tumor xenografts," Molecular Cancer Therapeutics, vol. 11, No. 4, pp. 898-908, 2012.
Godbole, et al., "Murine toxicology and pharmacokinetics evaluation of retinoic acid metabolism blocking agent (RAMBA), VN/12-1," Cancer Chemotherapy and Pharmacology, vol. 70, No. 2, pp. 339-344, 2012.
Sookoian, et al., "Epigenetic regulation of insulin resistance in nonalcoholic fatty liver disease: impact of liver methylation of the peroxisome proliferator-activated receptor gamma coactivator 1alpha promoter," Hepatology, vol. 52, No. 6, pp. 1992-2000, 2010.
Soprano et al., "Retinoic acid receptors and cancers," Annual Review of Nutrition, vol. 24, pp. 201-221, 2004.
Staels, "Regulation of lipid and lipoprotein metabolism by retinoids," Journal of the American Academy of Dermatology, vol. 45, No. 5, pp. S158-S167, 2001.
Stearns, et al., "Liarozole and 13-cis-retinoic acid anti-prostatic tumor activity," Cancer Research, vol. 53, No. 13, pp. 3073-3077, 1993.
Stoll, et al., "Retinoid regulation of heparin-binding EGF-like growth factor gene expression in human keratinocytes and skin," Experimental Dermatology, vol. 7, No. 6, pp. 391-397, 1998.
Stopple, et al., "R115866 inhibits all-trans-retinoic acid metabolism and exerts retinoidal effects in rodents," Journal of Pharmacology and Experimental Therapeutics, vol. 293, No. 1, pp. 304-312, 2000.
St-Pierre, et al., "Bioenergetic analysis of peroxisome proliferator-activated receptor gamma coactivators 1alpha and 1beta (PGC-1alpha and PGC-1beta) in muscle cells," Journal of Biological Chemistry, vol. 278, No. 29, pp. 26597-26603, 2003.
Sun, et al., "Highly efficient chemoselective deprotection of O,O-acetals and O,O-ketals catalyzed by molecular iodine in acetone," Journal of Organic Chemistry, vol. 69, No. 25, pp. 8932-8934, 2004.
Symoens, et al., "An evaluation of two years of clinical experience with ketoconazole [with discussion and concluding remarks]," Reviews of Infectious Diseases, vol. 2, No. 4, pp. 674-691, 1980.
Taimi et al., "A novel human cytochrome P450, CYP26C1, involved in metabolism of 9-cis and all-trans isomers of retinoic acid," Journal of Biological Chemistry, vol. 279, No. 1, pp. 77-85, 2004.
Takeuchi, et al., "Re-induction of complete remission with a new synthetic retinoid, Am-80, for relapse of acute promyelocytic leukaemia previously treated with all-trans retinoic acid," British Journal of Haematology, vol. 97, No. 1, pp. 137-140, 1997.
Tallman, et al., "All-trans-Retinoic Acid in Acute Promyelocytic Leukemia," New England Journal of Medicine, vol. 337, No. 15, pp. 1021-1028, 1997.

(56) References Cited

OTHER PUBLICATIONS

Tang, "Retinoids, retinoic acid receptors, and cancer," Annual Review of Pathology: Mechanisms of Disease, vol. 6, pp. 345-364, 2011.

Tang-Liu, et al., "Clinical pharmacokinetics and drug metabolism of tazarotene: a novel topical treatment for acne and psoriasis," Clinical Pharmacokinetics, vol. 37, No. 4, pp. 273-287, 1999.

Tapazoglou, et al., "High-dose ketoconazole therapy in patients with metastatic prostate cancer," American Journal of Clinical Oncology, vol. 9, No. 5, pp. 369-375, 1986.

Tay, et al., "A comparison of the roles of peroxisome proliferator-activated receptor and retinoic acid receptor on CYP26 regulation," Molecular Pharmacology, vol. 77, No. 2, pp. 218-227, 2010.

Thatcher, "The role of CYP26 enzymes in retinoic acid clearance," Expert Opinion on Drug Metabolism & Toxicology, vol. 5, No. 8, pp. 875-886, 2009.

Thatcher, et al., "Substrate specificity and ligand interactions of CYP26A1, the human liver retinoic acid hydroxylase," Molecular Pharmacology, vol. 80, No. 2, pp. 228-239, 2011.

Thatcher, et al., "The relative importance of CYP26A1 in hepatic clearance of all-trans retinoic acid," Biochemical Pharmacology, vol. 80, No. 6, pp. 903-912, 2010.

Tiboni, et al., "Fluconazole alters CYP26 gene expression in mouse embryos," Reproductive Toxicology, vol. 27, No. 2, pp. 199-202, 2009.

Topletz et al., "Comparison of the function and expression of CYP26A1 and CYP26B1, the two retinoic acid hydroxylases," Biochemical Pharmacology, vol. 83, No. 1, pp. 149-163, 2012.

Topletz, et al., "Induction of CYP26A1 by Metabolites of Retinoic Acid: Evidence that CYP26A1 is an Important Enzyme in the Elimination of Active Retinoids," Molecular Pharmacology, vol. 87, No. 3, pp. 430-441, 2015.

Trasino, et al., "Obesity Leads to Tissue, but not Serum Vitamin A Deficiency," Scientific Reports, vol. 5, 10 pages, 2015.

Travis, et al., "Diseases caused by defects in the visual cycle: retinoids as potential therapeutic agents," Annual Review of Pharmacology and Toxicology, vol. 47, pp. 469-512, 2007.

Tripathy, et al., "All-Trans-Retinoic Acid Enhances Mitochondrial Function in Models of Human Liver," Molecular Pharmacology, vol. 89, No. 5, pp. 560-574, 2016.

Uehara, et al., "CYP26A1 and CYP26C1 cooperatively regulate anterior-posterior patterning of the developing brain and the production of migratory cranial neural crest cells in the mouse," Developmental Biology, vol. 302, No. 2, pp. 399-411, 2007.

Ueno, et al., "Itraconazole and retinoid resistance," American Journal of Hematology, vol. 50, No. 4, pp. 319-320, 1995.

van der Leede, et al., "Autoinduction of retinoic acid metabolism to polar derivatives with decreased biological activity in retinoic acid-sensitive, but not in retinoic acid-resistant human breast cancer cells," Journal of Biological Chemistry, vol. 272, No. 29, pp. 17921-17928, 1997.

Van Ginckel, et al., "Antitumoral effects of R 75251 on the growth of transplantable R3327 prostatic adenocarcinoma in rats," Prostate, vol. 16, No. 4, pp. 313-323, 1990.

Van heusden, et al., "All-trans-retinoic acid metabolites significantly inhibit the proliferation of MCF-7 human breast cancer cells in vitro," British Journal of Cancer, vol. 77, No. 1, pp. 26-32, 1998.

Van Heusden, et al., "Inhibition of all-trans-retinoic acid metabolism by R116010 induces antitumour activity," British Journal of Cancer, vol. 86, No. 4, pp. 605-611, 2002.

Van Heusden, et al., "Liarozole potentiates the all-trans-retinoic acid-induced structural remodelling in human breast carcinoma MCF-7 cells in vitro," European Journal of Cell Biology, vol. 71, No. 1, pp. 89-98, 1996.

Van heusden, et al., "The antiproliferative activity of all-trans-retinoic acid catabolites and isomers is differentially modulated by liarozole-fumarate in MCF-7 human breast cancer cells," British Journal of Cancer, vol. 77, No. 8, pp. 1229-1235, 1998.

van Pelt, et al., (Mar.-Apr. 1998) "Effects of systemic treatment with liarozole on cutaneous inflammation, epidermal proliferation and differentiation in extensive plaque psoriasis," Skin Pharmacology and Applied Skin Physiology, vol. 11, No. 2, pp. 70-79, 1998.

Van Wauwe et al., "Ketoconazole inhibits the in vitro and in vivo metabolism of all-trans-retinoic acid," Journal of Pharmacology and Experimental Therapeutics, vol. 245, No. 2, pp. 718-722, 1988.

Van Wauwe, et al., "Effects of cytochrome P-450 inhibitors on the in vivo metabolism of all-trans-retinoic acid in rats," Journal of Pharmacology and Experimental Therapeutics, vol. 252, No. 1, pp. 365-369, 1990.

Van Wauwe, et al., "Liarozole fumarate inhibits the metabolism of 4-keto-all-trans-retinoic acid," Biochemical Pharmacology, vol. 47, No. 4, pp. 737-741, 1994.

Van Wauwe, et al., "Liarozole, an inhibitor of retinoic acid metabolism, exerts retinoid-mimetic effects in vivo," Journal of Pharmacology and Experimental Therapeutics, vol. 261, No. 2, pp. 773-779, 1992.

Vanier et al., "Interaction of all-trans-retinoic acid with fluconazole in acute promyelocytic leukemia," Journal of Pediatric Hematology/Oncology, vol. 25, No. 5, pp. 403-404, 2003.

Varhe et al., "Fluconazole, but not terbinafine, enhances the effects of triazolam by inhibiting its metabolism," British Journal of Clinical Pharmacology, vol. 41, No. 4, pp. 319-323, 1996.

Varhe, et al. "Oral triazolam is potentially hazardous to patients receiving systemic antimycotics ketoconazole or itraconazole,"Clinical Pharmacology & Therapeutics, vol. 56, No. 6, Pt 1, pp. 601-607, 1994.

Vasaitis, et al., "CYP17 inhibitors for prostate cancer therapy," Journal of Steroid Biochemistry & Molecular Biology, vol. 125, No. 1-2, pp. 23-31, 2011.

Veal, et al., "Pharmacokinetics and metabolism of 13-cis-retinoic acid (isotretinoin) in children with high-risk neuroblastoma—a study of the United Kingdom Children's Cancer Study Group," British Journal of Cancer, vol. 96, No. 3, pp. 424-431, 2007.

Verlaine et al., "Retinoic acid metabolism blocking agents (RAMBAs): a new paradigm in the treatment of hyperkeratotic disorders," Journal der Deutschen Dermatologischen Gesellschaft (Journal of the German Society of Dermatology), vol. 6, No. 5, pp. 355-364, 2008.

Verfaille, et al. "Oral R115866 in the treatment of moderate to severe facial acne vulgaris: an exploratory study," British Journal of Dermatology, vol. 157, No. 1, pp. 122-126, 2007.

Verfaille, et al., "Oral R115866 in the treatment of moderate to severe plaque-type psoriasis," Journal of the European Academy of Dermatology and Venereology, vol. 21, No. 8, pp. 1038-1046, 2007.

Walsky, et al., "Validated assays for human cytochrome P450 activities," Drug metabolism and disposition: the biological fate of chemicals, vol. 32, No. 6, pp. 647-660, 2004.

Wang, et al., "Peroxisome proliferator-activated receptor {delta} is an essential transcriptional regulator for mitochondrial protection and biogenesis in adult heart," Circulation Research, vol. 106, No. 5, pp. 911-919, 2010.

Ward, et al., "The antioxidant status of patients with either alcohol-induced liver damage or myopathy," Alcohol and Alcoholism, vol. 27, No. 4, pp. 359-365, 1992.

Wei, et al., "Nonalcoholic fatty liver disease and mitochondrial dysfunction," World Journal of Gastroenterology, vol. 14, No. 2, pp. 193-199, 2008.

Weinstein, et al., "Tazarotene gel, a new retinoid, for topical therapy of psoriasis: Vehicle-controlled study of safety, efficacy, and duration of therapeutic effect," Journal of the American Academy of Dermatology, vol. 37, No. 1, pp. 85-92, 1997.

White, et al., "cDNA cloning of human retinoic acid-metabolizing enzyme (hP450RAI) identifies a novel family of cytochromes P450," Journal of Biological Chemistry, vol. 272, No. 30, pp. 18538-18541, 1997.

White, et al., "Identification of the human cytochrome P450, P450RAI-2, which is predominantly expressed in the adult cerebellum and is responsible for all-trans-retinoic acid metabolism," Proceedings of the National Academy of Sciences USA, vol. 97, No. 12, pp. 6403-6408, 2000.

White, et al., "Identification of the retinoic acid-inducible all-trans-retinoic acid 4-hydroxylase," Journal of Biological Chemistry, vol. 271, No. 47, pp. 29922-29927, 1996.

(56) References Cited

OTHER PUBLICATIONS

Wikipedia, "Bexarotene," retrieved online at: https://en.wikipedia.org/wiki/Bexarotene , 2016.
Williams, "Ketoconazole for prostate cancer," Lancet, vol. 2, No. 8404, pp. 696, 1984.
Williams, et al., "Inhibition of retinoic acid metabolism by imidazole antimycotics in F9 embryonal carcinoma cells," Biochemical Pharmacology, vol. 36, No. 8, pp. 1386-1388, 1987.
Woerdeman, et al., "In Young Men, a Moderate Inhibition of Testosterone Synthesis Capacity is Only Partly Compensated by Increased Activity of the Pituitary and the Hypothalamus," Clinical Endocrinology, vol. 72, No. 1, pp. 76-80, 2010.
Wolbach, et al., "Tissue Changes Following Deprivation of Fat-Soluble A Vitamin," Journal of Experimental Medicine, vol. 42, No. 6, pp. 753-777, 1925.
Wolf , "Retinoic acid activation of peroxisome proliferation-activated receptor delta represses obesity and insulin resistance," Nutrition Reviews, vol. 68, No. 1, pp. 67-70, 2010.
Wouters, et al., "Effects of liarozole, a new antitumoral compound, on retinoic acid-induced inhibition of cell growth and on retinoic acid metabolism in MCF-7 human breast cancer cells," Cancer Research, vol. 52, No. 10, pp. 2841-2846, 1992.
Xi, et al., "Expression of RALDHs (ALDH1As) and CYP26s in human tissues and during the neural differentiation of P19 embryonal carcinoma stem cell," Gene Expression Patterns, vol. 8, No. 6, pp. 438-442, 2008.
Xiao, et al., "Endogenous Retinoic Acid Receptor (RAR)-Retinoid X Receptor (RXR) Heterodimers Are the Major Functional Forms Regulating Retinoid-responsive Elements in Adult Human Keratinocytes: Binding of Ligands to RAR Only is Sufficient for RAR-RXR Heterodimers to Confer Ligand-Dependent Activation of hRARβ2/RARE (DR5)," Journal of Biological Chemistry, vol. 270, No. 7, pp. 3001-3011, 1995.
Yamamoto, et al., "Regulation of CYP26 (cytochrome P450RAI) mRNA expression and retinoic acid metabolism by retinoids and dietary vitamin A in liver of mice and rats," FASEB Journal, vol. 14, No. 13, pp. 2119-2127, 2000.
Yanagitani, et al., "Retinoic acid receptor alpha dominant negative form causes steatohepatitis and liver tumors in transgenic mice," Hepatology, vol. 40, No. 2, pp. 366-375, 2004.
Yang, et al., "All-trans retinoic acid regulates hepatic bile acid homeostasis," Biochemical Pharmacology, vol. 91, No. 4, pp. 483-489, 2014.
Yashiro, et al., "Regulation of retinoic acid distribution is required for proximodistal patterning and outgrowth of the developing mouse limb," Developmental Cell, vol. 6, No. 3, pp. 411-422, 2004.
Yee, et al., "Novel tetralone-derived retinoic acid metabolism blocking agents: synthesis and in vitro evaluation with liver microsomal and MCF-7 CYP26A1 cell assays," Journal of Medicinal Chemistry, vol. 48, No. 23, pp. 7123-7131, 2005.
Yoon, et al., "Pathogenesis and therapeutic approaches for nonalcoholic fatty liver disease," World Journal of Hepatology, vol. 6, No. 11, pp. 800-811, 2014.
Yu, et al., "Application of the Heck reaction in the synthesis of truncated naphthoic acid retinoids," Bioorganic & Medicinal Chemistry Letters, vol. 6, No. 23, pp. 2859-2864, 1996.
Yu, et al., "Retinoic acid induces neurogenesis by activating both retinoic acid receptors (RARs) and peroxisome proliferator-activated receptor beta/delta (PPARbeta/delta)," Journal of Biological Chemistry, vol. 287, No. 50, pp. 42195-42205, 2012.
Yu, et al., "Retinoic Acid Receptor β,γ-Selective Ligands: Synthesis and Biological Activity of 6-Substituted 2-Naphthoic Acid Retinoids," Journal of Medicinal Chemistry, vol. 39, No. 12, pp. 2411-2421, 1996.
Yu, et al., "Structural modifications of 6-naphthalene-2-carboxylate retinoids," Bioorganic & Medicinal Chemistry Letters, vol. 6, No. 23, pp. 2865-2870, 1996.
Zezos, et al., "Liver transplantation and non-alcoholic fatty liver disease," World Journal of Gastroenterology, vol. 20, No. 42, pp. 15532-15538, 2014.
Zhang, et al., "Effect of voriconazole and other azole antifungal agents on CYP3A activity and metabolism of tacrolimus in human liver microsomes," Xenobiotica, vol. 42, No. 5, pp. 409-416, 2012.
Zile, et al., "Identification of 13-cis retinoic acid in tissue extracts and its biological activity in rats," Biochimica et Biophysica Acta, vol. 141, No. 3, pp. 639-641, 1967.
Lazzarino et al.,"Clinical relevance of all-trans retinoic acid pharmacokinetics and its modulation in acute promyelocytic leukemia," Leukemia & Lymphoma, vol. 23, No. 5-6, pp. 539-543, 1996.
Lee, et al., (Jun. 1995) "Phase I evaluation of all-trans retinoic acid with and without ketoconazole in adults with solid tumors," Journal of Clinical Oncology, vol. 13, No. 6, pp. 1501-1508, 1995.
Lee, et al., "Retinoic acids and hepatic stellate cells in liver disease," Journal of Gastroenterology and Hepatology, vol. 27, Suppl 2, pp. 75-79, 2012.
Li et al., "Retinoic acid receptor beta stimulates hepatic induction of fibroblast growth factor 21 to promote fatty acid oxidation and control whole-body energy homeostasis in mice," Journal of Biological Chemistry, vol. 288, No. 15, pp. 10490-10504, 2013.
Li, et al., "Retinoids synergized with insulin to induce Srebp-1c expression and activated its promoter via the two liver X receptor binding sites that mediate insulin action," Biochemical and Biophysical Research Communications, vol. 406, No. 2, pp. 268-272, 2011.
Lilley, et al., "Oral retinoids and plasma lipids," Dermatologic Therapy, vol. 26, No. 5, pp. 404-410, 2013.
Liu, et al., "A model for random sampling and estimation of relative protein abundance in shotgun proteomics," Analytical Chemistry, vol. 76, No. 14, pp. 4193-4201, 2004.
Liu, et al., "Association of serum retinoic acid with hepatic steatosis and liver injury in nonalcoholic fatty liver disease," American Journal of Clinical Nutrition, vol. 102, No. 1, pp. 130-137, 2015.
Liu, et al., "Cardiomyocyte-Restricted Deletion of PPARbeta/delta in PPARalpha-Null Mice Causes Impaired Mitochondrial Biogenesis and Defense, but No Further Depression of Myocardial Fatty Acid Oxidation," PPAR Research, 372854, 2011.
Liu, et al., "Peroxisome proliferator-activated receptor beta/delta activation in adult hearts facilitates mitochondrial function and cardiac performance under pressure-overload condition," Hypertension, vol. 57, No. 2, pp. 223-230, 2011.
Lotan et al., "Inhibition of tumor cell growth by retinoids," Methods in Enzymology, vol. 190, pp. 100-110, 1990.
Lotan, "Effects of vitamin A and its analogs (retinoids) on normal and neoplastic cells," Biochimica et Biophysica Acta, vol. 605, No. 1, pp. 33-91, 1980.
Lucker et al., "Topical liarozole in ichthyosis: a double-blind, left-right comparative study followed by a long-term open maintenance study," British Journal of Dermatology, vol. 152, No. 3, pp. 566-569, 2005.
Lucker et al., "Oral treatment of ichthyosis by the cytochrome P-450 inhibitor liarozole," British Journal of Dermatology, vol. 136, No. 1, pp. 71-75, 1997.
Lutz, et al., "Expression and functional characterization of cytochrome P450 26A1, a retinoic acid hydroxylase," Biochemical Pharmacology, vol. 77, No. 2, pp. 258-268, 2009.
MacLean, et al., "Cloning of a novel retinoic-acid metabolizing cytochrome P450, Cyp26B1, and comparative expression analysis with Cyp26A1 during early murine development," Mechanisms of Development, vol. 107, No. 1-2, pp. 195-201, 2001.
Maden, "Retinoic acid in the development, regeneration and maintenance of the nervous system," Nature Reviews Neuroscience, vol. 8, No. 10, pp. 755-765, 2007.
Mahler, et al., "Ketoconazole and liarozole in the treatment of advanced prostatic cancer," Cancer, vol. 71, No. 3 Suppl, pp. 1068-1073, 1993.
Mahler, et al., "The effects of a new imidazole derivative in advanced prostatic cancer. A preliminary report," Progress in Clinical and Biological Research, vol. 303, pp. 205-209, 1989.
Mamoon, et al., (Oct. 2014) "Retinoic acid regulates several genes in bile acid and lipid metabolism via upregulation of small heterodimer partner in hepatocytes," Gene, vol. 550, No. 2, pp. 165-170, 2014.

(56) References Cited

OTHER PUBLICATIONS

Marill, et al., "Identification of human cytochrome P450s involved in the formation of all-trans-retinoic acid principal metabolites," Molecular Pharmacology, vol. 58, No. 6, pp. 1341-1348, 2000.
Mark, et al., "Role of retinoic acid receptor (RAR) signaling in post-natal male germ cell differentiation," Biochimica et Biophysica Acta (BBA)—Gene Regulatory Mechanisms, vol. 1849, No. 2, pp. 84-93, 2015.
McClintick, et al., "Global effects of vitamin a deficiency on gene expression in rat liver: evidence for hypoandrogenism," Journal of Nutritional Biochemistry, vol. 17, No. 5, pp. 345-355, 2006.
McCormick, et al., "13-cis-retinoic acid metabolism in vivo. The major tissue metabolites in the rat have the all-trans configuration," Biochemistry, vol. 22, No. 16, pp. 3933-3940, 1983.
McSorley, et al., "Identification of human cytochrome P450 isoforms that contribute to all-trans-retinoic acid 4- hydroxylation," Biochemical Pharmacology, vol. 60, No. 4, pp. 517-526, 2000.
Menter, "Pharmacokinetics and safety of tazarotene," Journal of the American Academy of Dermatology, vol. 43, No. 2, Pt 3, pp. S31-S35, 2000.
Miller Jr., "The emerging role of retinoids and retinoic acid metabolism blocking agents in the treatment of cancer," Cancer, vol. 83, No. 8, pp. 1471-1482, 1998.
Miller, et al., "Modulation of all-trans retinoic acid pharmacokinetics by liarozole," Cancer Chemotherapy & Pharmacology, vol. 34, No. 6, pp. 522-526, 1994.
Miyabe, et al., "Am80, a retinoic acid receptor agonist, ameliorates murine vasculitis through the suppression of neutrophil migration and activation," Arthritis & Rheumatology, vol. 65, No. 2, pp. 503-512, 2013.
Miyaura, et al., "The Palladium-Catalyzed Cross-Coupling Reaction of Phenylboronic Acid with Haloarenes in the Presence of Bases," Synthetic Communications, vol. 11, No. 7, pp. 513-519, 1981.
Moffat, et al., "Ketoconazole as primary treatment of prostatic cancer," British Journal of Urology, vol. 61, No. 5, 439-440, 1988.
Moriwaki, et al., "Effects of dietary retinoid and triglyceride on the lipid composition of rat liver stellate cells and stellate cell lipid droplets," Journal of Lipid Research, vol. 29, pp. 1523-1534, 1998.
Muindi, et al. (Jan. 1992) "Continuous treatment with all-trans retinoic acid causes a progressive reduction in plasma drug concentrations: implications for relapse and retinoid 'resistance' in patients with acute promyelocytic leukemia," Blood, vol. 79, No. 2, pp. 299-303, 1992.
Muindi, et al., "Clinical pharmacology of oral all-trans retinoic acid in patients with acute promyelocytic leukemia," Cancer Research, vol. 52, No. 8, pp. 2138-2142, 1992.
Mulvihill, et al., "3-[6-(2-Dimethylamino-1-imidazol-1-yl-butyl)-naphthalen-2-yloxy]-2,2-dimethyl-propionic acid as a highly potent and selective retinoic acid metabolic blocking agent," Bioorganic & Medicinal Chemistry Letters, vol. 16, No. 10, pp. 2729-2733, 2006.
Mulvihill, et al., "Potent and selective [2-imidazol-1-yl-2-(6-alkoxy-naphthalen-2-yl)-1-methyl-ethyl]-dimethyl-amines as retinoic acid metabolic blocking agents (RAMBAs)," Bioorganic & Medicinal Chemistry Letters, vol. 15, No. 6, pp. 1669-1673, 2005.
Nadin, et al., "Participation of CYP2C8 in retinoic acid 4-hydroxylation in human hepatic microsomes," Biochemical Pharmacology, vol. 58, No. 7, pp. 1201-1208, 1999.
Napoli, "Biochemical pathways of retinoid transport, metabolism, and signal transduction," Clinical Immunology and Immunopathology, vol. 80, No. 3, Pt 2, pp. S52-S62, 1996.
Nelson, et al. "Therapeutic potential of the inhibition of the retinoic acid hydroxylases CYP26A1 and CYP26B1 by xenobiotics," Current Topics in Medicinal Chemistry, vol. 13, No. 12, pp. 1402-1428, 2013.
Nesvizhskii, et al., "A statistical model for identifying proteins by tandem mass spectrometry," Analytical Chemistry, vol. 75, No. 17, pp. 4646-4658, 2003.
Neuville, et al., "Retinoic Acid Regulates Arterial Smooth Muscle Cell Proliferation and Phenotypic Features In Vivo and In Vitro Through an RARα-Dependent Signaling Pathway," Arteriosclerosis, Thrombosis, and Vascular Biology, vol. 19, pp. 1430-1436, 1999.
Niederreither et al., "Genetic evidence that oxidative derivatives of retinoic acid are not involved in retinoid signaling during mouse development," Nature Genetics, vol. 31, No. 1, pp. 84-88, 2002.
Njar, "Cytochrome p450 retinoic acid 4-hydroxylase inhibitors: potential agents for cancer therapy," Mini Reviews in Medicinal Chemistry, vol. 2, No. 3, pp. 261-269, 2002.
Njar, et al., "Potent inhibition of retinoic acid metabolism enzyme(s) by novel azolyl retinoids," Bioorganic & Medicinal Chemistry Letters, vol. 10, No. 17, pp. 1905-1908, 2000.
Njar, et al., "Retinoic acid metabolism blocking agents (RAMBAs) for treatment of cancer and dermatological diseases," Bioorganic & Medicinal Chemistry, vol. 14, No. 13, pp. 4323-4340, 2006.
Nonnecke, et al., "Reactivity and phenotype of mononuclear leukocytes from nongravid heifers after in vitro exposure to 9,13-di-cis-retinoic acid," Journal of Dairy Science, vol. 80, No. 11, pp. 2833-2841, 1997.
Noy, "Between death and survival: retinoic acid in regulation of apoptosis," Annual Review of Nutrition, vol. 30, pp. 201-217, 2010.
Noy, "Retinoid-binding proteins: mediators of retinoid action," Biochemical Journal, vol. 348, Pt 3, pp. 481-495, 2000.
O'Byrne, et al., "Phase II study of liarozole in advanced non-small cell lung cancer," European Journal of Cancer, vol. 34, No. 9, pp. 1463-1466, 1998.
Obrochta, et al., "Insulin Regulates Retinol Dehydrogenase Expression and all-trans-Retinoic Acid Biosynthesis through FoxO1," Journal of Biological Chemistry, vol. 290, No. 11, pp. 7259-7268, 2015.
CAS Registry No. 110952-37-9 (retrieved on SciFinder Aug. 2016).
CAS Registry No. 111359-44-5 (retrieved on SciFinder Aug. 2016).
CAS Registry No. 111359-55-8 (retrieved on SciFinder Aug. 2016).
CAS Registry No. 112110-24-4 (retrieved on SciFinder Aug. 2016).
CAS Registry No. 112110-25-5 (retrieved on SciFinder Aug. 2016).
CAS Registry No. 112110-28-8 (retrieved on SciFinder Aug. 2016).
CAS Registry No. 112110-30-2 (retrieved on SciFinder Aug. 2016).
CAS Registry No. 112110-33-5 (retrieved on SciFinder Aug. 2016).
CAS Registry No. 112110-40-4 (retrieved on SciFinder Aug. 2016).
CAS Registry No. 112136-02-4 (retrieved on SciFinder Aug. 2016).
CAS Registry No. 113263-05-1 (retrieved on SciFinder Aug. 2016).
CAS Registry No. 117168-45-3 (retrieved on SciFinder Aug. 2016).
CAS Registry No. 117259-96-8 (retrieved on SciFinder Aug. 2016).
CAS Registry No. 117260-03-4 (retrieved on SciFinder Aug. 2016).
CAS Registry No. 117260-04-5 (retrieved on SciFinder Aug. 2016).
CAS Registry No. 118292-41-4 (retrieved on SciFinder Aug. 2016).
CAS Registry No. 1285322-05-5 (retrieved on SciFinder Aug. 2016).
CAS Registry No. 1298117-18-6 (retrieved on SciFinder Aug. 2016).
CAS Registry No. 1298117-19-7 (retrieved on SciFinder Aug. 2016).
CAS Registry No. 1298117-20-0 (retrieved on SciFinder Aug. 2016).
CAS Registry No. 1298117-21-1 (retrieved on SciFinder Aug. 2016).
CAS Registry No. 1298117-23-3 (retrieved on SciFinder Aug. 2016).
CAS Registry No. 1298117-25-5 (retrieved on SciFinder Aug. 2016).
CAS Registry No. 132392-15-5 (retrieved on SciFinder Aug. 2016).
CAS Registry No. 132392-16-6 (retrieved on SciFinder Aug. 2016).
CAS Registry No. 1416254-93-7 (retrieved on SciFinder Aug. 2016).
CAS Registry No. 146670-40-8 (retrieved on SciFinder Aug. 2016).
CAS Registry No. 153559-49-0 (retrieved on SciFinder Aug. 2016).
CAS Registry No. 1561256-11-8 (retrieved on SciFinder Aug. 2016).
CAS Registry No. 1602593-11-2 (retrieved on SciFinder Aug. 2016).
CAS Registry No. 162258-18-6 (retrieved on SciFinder Aug. 2016).
CAS Registry No. 165050-38-4 (retrieved on SciFinder Aug. 2016).
CAS Registry No. 168198-08-1 (retrieved on SciFinder Aug. 2016).

(56) References Cited

OTHER PUBLICATIONS

CAS Registry No. 174154-97-3 (retrieved on SciFinder Aug. 2016).
CAS Registry No. 174406-12-3 (retrieved on SciFinder Aug. 2016).
CAS Registry No. 177361-08-9 (retrieved on SciFinder Aug. 2016).
CAS Registry No. 185629-22-5 (retrieved on SciFinder Aug. 2016).
CAS Registry No. 185685-50-1 (retrieved on SciFinder Aug. 2016).
CAS Registry No. 186526-11-4 (retrieved on SciFinder Aug. 2016).
CAS Registry No. 186526-15-8 (retrieved on SciFinder Aug. 2016).
CAS Registry No. 215307-86-1 (retrieved on SciFinder Aug. 2016).
CAS Registry No. 345952-44-5 (retrieved on SciFinder Aug. 2016).
CAS Registry No. 459820-79-2 (retrieved on SciFinder Aug. 2016).
CAS Registry No. 65170-94-7 (retrieved on SciFinder Aug. 2016).
CAS Registry No. 843662-52-2 (retrieved on SciFinder Aug. 2016).
CAS Registry No. 843662-53-3 (retrieved on SciFinder Aug. 2016).
CAS Registry No. 854883-95-7 (retrieved on SciFinder Aug. 2016).
CAS Registry No. 867183-82-2 (retrieved on SciFinder Aug. 2016).
CAS Registry No. 867187-49-3 (retrieved on SciFinder Aug. 2016).
CAS Registry No. 941688-50-2 (retrieved on SciFinder Aug. 2016).
Gomaa et al., "Synthesis and biological evaluation of 3-(1H-imidazol- and triazol-1-yl)-2,2-dimethyl-3-[4-(naphthalen-2-ylamino)phenyl]propyl derivatives as small molecule inhibitors of retinoic acid 4-hydroxylase (CYP26)," Journal of Medicinal Chemistry, vol. 54, No. 19, pp. 6803-6811, 2011.
Gomaa, et al., "Homology model of human retinoic acid metabolising enzyme cytochrome P450 26A1 (CYP26A1): active site architecture and ligand binding," Journal of Enzyme Inhibition and Medicinal Chemistry, vol. 21, No. 4, pp. 361-369, 2006.
Gomaa, et al., "Novel azolyl-(phenylmethyl)]aryl/heteroarylamines: Potent CYP26 inhibitors and enhancers of all-trans retinoic acid activity in neuroblastoma cells," Bioorganic & Medicinal Chemistry, vol. 16, No. 17, pp. 8301-8313, 2008.
Gomaa, et al., "Novel retinoic acid 4-hydroxylase (CYP26) inhibitors based on a 3-(1-imidazol- and triazol-1-yl)-2,2-dimethyl-3-(4-(henylamino)phenyl)propyl scaffold," Bioorganic & Medicinal Chemistry, vol. 20, No. 14, pp. 4201-4207, 2012.
Gomaa, et al., "Small molecule inhibitors of retinoic acid 4-hydroxylase (CYP26): synthesis and biological evaluation of imidazole methyl 3-(4-(aryl-2-ylamino)phenyl)propanoates," Journal of Medicinal Chemistry, vol. 54, No. 8, pp. 2778-2791, 2011.
Goodman, et al., "Evidence for defective retinoid transport and function in late onset Alzheimer's disease," Proceedings of the National Academy of Sciences USA, vol. 100, No. 5, pp. 2901-2905, 2003.
Goss, et al. (Nov. 2000) "Liarozole fumarate (R85246): in the treatment of ER negative, tamoxifen refractory or chemotherapy resistant postmenopausal metastatic breast cancer," Breast Cancer Research and Treatment, vol. 64, No. 2, pp. 177-188, 2000.
Goss, et al., "Anti-tumor effects of a novel retinoic acid metabolism blocking agent VN/14-1 in the N-methyl-N-nitrosourea-induced rat mammary carcinoma model and its effects on the uterus," Breast Cancer Research and Treatment, vol. 133, No. 1, pp. 137-144, 2012.
Goss, et al., "Effects of liarozole fumarate (R85246) in combination with tamoxifen on N-methyl-N-nitrosourea (MNU)-induced mammary carcinoma and uterus in the rat model," BMC Cancer, vol. 7, No. 26, 2007.
Goss, et al., "Liarozole fumarate (R85246): a novel imidazole in the treatment of receptor positive postmenopausal metastatic breast cancer," Breast Cancer Research and Treatment, vol. 59, No. 1, pp. 55-68, 2000.
Graupner, et al., "6'-Substituted naphthalene-2-carboxylic acid analogs, a new class of retinoic acid receptor subtype-specific ligands," Biochemical and Biophysical Research Communications, vol. 179, No. 3, pp. 1554-1561, 1991.
Greer et al., "Some 1,2-diphenylethane derivatives as inhibitors of retinoic acid-metabolising enzymes," Journal of Enzyme Inhibition and Medicinal Chemistry, vol. 18, No. 5, pp. 431-443, 2003.
Gudas, et al., "Retinoids regulate stem cell differentiation," Journal of Cellular Physiology, vol. 226, No. 2, pp. 322-330, 2011.
Hale, "The relation of maternal vitamin a deficiency to microphthalmia in pigs," Texas State Journal of Medicine, vol. 33, pp. 228-232, 1937.
Hamilton, et al., "A phase II study of liarozole in postmenopausal patients with 'chemotherapy resistant' or 'potentially hormone sensitive' metastatic breast cancer," Breast Cancer Research and Treatment, vol. 60, No. 2, pp. 181-188, 2000.
Han, et al., "Highly specific cytochrome P450-like enzymes for all-trans-retinoic acid in T47D human breast cancer cells," Journal of Clinical Endocrinology & Metabolism, vol. 81, No. 6, pp. 2069-2075, 1996.
Handa et al., "Reduced adiponectin signaling due to weight gain results in nonalcoholic steatohepatitis through impaired mitochondrial biogenesis," Hepatology, vol. 60, No. 1, pp. 133-145, 2014.
Harant, et al., "Retinoic acid receptors in retinoid responsive ovarian cancer cell lines detected by polymerase chain reaction following reverse transcription," British Journal of Cancer, vol. 68, No. 3, pp. 530-536, 1993.
Hartmann et al., "Exposure to retinoic acids in non-pregnant women following high vitamin A intake with a liver meal," International Journal of Vitamin and Nutrition Research, vol. 75, No. 3, pp. 187-194, 2005.
Hartmann, et al., "Exposure to retinyl esters, retinol, and retinoic acids in non-pregnant women following increasing single and repeated oral doses of vitamin A," Annals of Nutrition & Metabolism, vol. 49, No. 3, pp. 155-164, 2005.
Havilio, et al., "Intensity-based statistical scorer for tandem mass spectrometry," Analytical Chemistry, vol. 75, No. 3, pp. 435-444, 2003.
Heise, et al., "Skin retinoid concentrations are modulated by CYP26AI expression restricted to basal keratinocytes in normal human skin and differentiated 3D skin models," Journal of Investigative Dermatology, vol. 126, No. 11, pp. 2473-2480, 2006.
Helvig, et al., "Functional properties and substrate characterization of human CYP26A1, CYP26B1, and CYP26C1 expressed by recombinant baculovirus in insect cells," Journal of Pharmacological and Toxicological Methods, vol. 64, No. 3, pp. 258-263, 2011.
Holmes, et al., "Induction of apoptosis in ovarian carcinoma cells by AHPN/CD437 is mediated by retinoic acid receptors," Journal of Cellular Physiology, vol. 185, No. 1, pp. 61-67, 2000.
Hondares et al., "PPARdelta, but not PPARalpha, activates PGC-1alpha gene transcription in muscle," Biochemical and Biophysical Research Communications, vol. 354, No. 4, pp. 1021-1027, 2007.
Huang, et al., "Targeting FtsZ for Antituberculosis Drug Discovery: Noncytotoxic Taxanes as Novel Antituberculosis Agents," Journal of Medicinal Chemistry, vol. 49, No. 2, pp. 463-466, 2005.
Huynh, et al., "Inhibitory effects of retinoic acid metabolism blocking agents (RAMBAs) on the growth of human prostate cancer cells and LNCaP prostate tumour xenografts in SCID mice," British Journal of Cancer, vol. 4, No. 4, pp. 513-523, 2006.
Idres, et al., "Activation of retinoic acid receptor-dependent transcription by all-trans-retinoic acid metabolites and isomers," Journal of Biological Chemistry, vol. 277, No. 35, pp. 31491-31498, 2002.
Kagechika, et al., "Synthetic Retinoids: Recent Developments Concerning Structure and Clinical Utility," Journal of Medicinal Chemistry, vol. 48, No. 19, pp. 5875-5883, 2005.
Kane, et al., "Identification of 9-cis-retinoic acid as a pancreas-specific autacoid that attenuates glucose-stimulated insulin secretion," Proceedings of the National Academy of Sciences USA, vol. 107, No. 50, pp. 21884-21889, 2010.
Kane, et al., "Quantitative profiling of endogenous retinoic acid in vivo and in vitro by tandem mass spectrometry," Analytical Chemistry, vol. 80, No. 5, pp. 1702-1708, 2008.
Kang, et al., "Liarozole inhibits human epidermal retinoic acid 4-hydroxylase activity and differentially augments human skin responses to retinoic acid and retinol in vivo," Journal of Investigative Dermatology, vol. 107, No. 2, pp. 183-187, 1996.
Karlsson, et al., "Homology Models and Molecular Modeling of Human Retinoic Acid Metabolizing Enzymes Cytochrome P450 26A1 (CYP26A1) and P450 26B1 (CYP26131)," Journal of Chemical Theory and Computation, vol. 4, No. 6, pp. 1021-1027, 2008.

(56) References Cited

OTHER PUBLICATIONS

Keller, et al., 2002 "Empirical statistical model to estimate the accuracy of peptide identifications made by MS/MS and database search," Analytical Chemistry, vol. 74, No. 20, pp. 5383-5392, 2002.
Khandare, et al., "Synthesis and Antitumor Activity of New Retinobenzoic Acids," Chemistry & Biodiversity, vol. 8, No. 5, pp. 841-849, 2011.
Khandelwal, et al., "MS-275 synergistically enhances the growth inhibitory effects of RAMBA VN/66-1 in hormone-insensitive PC-3 prostate cancer cells and tumours," British Journal of Cancer, vol. 98, No. 7, pp. 1234-1243, 2008.
Kim, et al., "All-trans-retinoic acid ameliorates hepatic steatosis in mice by a novel transcriptional cascade," Hepatology, vol. 59, No. 5, pp. 1750-1760, 2014.
Kirby, et al., "Inhibition of retinoic acid metabolising enzymes by 2-(4-aminophenylmethyl)-6-hydroxy-3,4-dihydronaphthalen-1(2H)-one and related compounds," Journal of Enzyme Inhibition and Medicinal Chemistry, vol. 18, No. 1, pp. 27-33, 2003.
Kirby, et al., "Some 3-(4-aminophenyl)pyrrolidine-2,5-diones as all-trans-retinoic acid metabolising enzyme inhibitors (RAMBAs)," Journal of Enzyme Inhibition and Medicinal Chemistry, vol. 17, No. 5, pp. 321-327, 2002.
Kirchmeyer, et al., "All-trans retinoic acid suppresses interleukin-6 expression in interleukin-1-stimulated synovial fibroblasts by inhibition of ERK1/2pathway independently of RAR activation," Arthritis Research & Therapy, vol. 10, No. 3, pp. R141, 12 pages, 2008.
Kistler, "Hypervitaminosis A: side-effects of retinoids," Biochemical Society Transactions, vol. 14, No. 5, pp. 936-939. 1986.
Koh, et al., "Altered expression of small heterodimer partner governs cytochrome P450 (CYP) 2D6 induction during pregnancy in CYP2D6-humanized mice," Journal of Biological Chemistry, vol. 289, No. 6, pp. 3105-3113, 2014.
Koves, et al., "Peroxisome proliferator-activated receptor-gamma co-activator 1alpha-mediated metabolic remodeling of skeletal myocytes mimics exercise training and reverses lipid-induced mitochondrial inefficiency," Journal of Biological Chemistry, vol. 280, No. 39, pp. 33588-33598, 2005.
Krekels, et al., "Analysis of the oxidative catabolism of retinoic acid in rat Dunning R3327G prostate tumors," Prostate, vol. 29, No. 1, pp. 36-41, 1996.
Krekels, et al., "Induction of the oxidative catabolism of retinoid acid in MCF-7 cells," British Journal of Cancer, vol. 75, No. 8, pp. 1098-1104, 1997.
Kuijpers, et al., "The effects of oral liarozole on epidermal proliferation and differentiation in severe plaque psoriasis are comparable with those of acitretin," British Journal of Dermatology, vol. 139, No. 3, pp. 380-389, 1998.
Kurlandsky, et al., "Plasma delivery of retinoic acid to tissues in the rat," Journal of Biological Chemistry, vol. 270, No. 30, pp. 17850-17857, 1995.
Lampen, et al., "Metabolism of vitamin a and its active metabolite all-trans-retinoic acid in small intestinal enterocytes," Journal of Pharmacology and Experimental Therapeutics, vol. 295, No. 3, pp. 979-985, 2000.
Lansink, et al., "Differences in metabolism and isomerization of all-trans-retinoic acid and 9-cis-retinoic acid between human endothelial cells and hepatocytes," European Journal of Biochemistry, vol. 247, No. 2, pp. 596-604, 1997.
Lawrence, et al., "Phase I clinical trial of alitretinoin and tamoxifen in breast cancer patients: toxicity, pharmacokinetic, and biomarker evaluations," Journal of Clinical Oncology, vol. 19, No. 10, pp. 2754-2763, 2001.
O'Byrne, et al., "Retinol and retinyl esters: biochemistry and physiology," Journal of Lipid Research, vol. 54, No. 7, pp. 1731-1743, 2013.
Ohta, et al., "Structure-activity relationship study on benzoic acid part of diphenylamine-based retinoids," Bioorganic & Medicinal Chemistry Letters, vol. 23, No. 1, pp. 81-84, 2013.

Oikawa et al., "Three novel synthetic retinoids, Re 80, Am 580 and Am 80, all exhibit anti-angiogenic activity in vivo," European Journal of Pharmacology, vol. 249, No. 1-2, pp. 113-116, 1993.
Ojima, et al., "Design, Synthesis and Structure-Activity Relationships of Novel Taxane-Based Multidrug Resistance Reversal Agents," Journal of Medicinal Chemistry, vol. 48, No. 6, pp. 2218-2228, 2005.
Oliveros, et al., "Vitamin a deficiency modifies lipid metabolism in rat liver," British Journal of Nutrition, vol. 97, No. 2, pp. 263-272, 2007.
Orfanos, et al., "Current use and future potential role of retinoids in dermatology," Drugs, vol. 53, No. 3, pp. 358-388, 1997.
Osanai, et al., "Expression of the retinoic acid-metabolizing enzyme CYP26A1 limits programmed cell death," Molecular Pharmacology, vol. 67, No. 5, pp. 1808-1817, 2005.
Paik, et al., "Inhibition of retinoic acid biosynthesis by the bisdichloroacetyldiamine WIN 18,446 markedly suppresses spermatogenesis and alters retinoid metabolism in mice," Journal of Biological Chemistry, vol. 289, No. 21, pp. 15104-15117, 2014.
Panchaud, et al. "Faster, quantitative, and accurate precursor acquisition independent from ion count," Analytical Chemistry, vol. 83, No. 6, pp. 2250-2257, 2011.
Panchaud, et al., "Precursor acquisition independent from ion count: how to dive deeper into the proteomics ocean," Analytical Chemistry, vol. 81, No. 15, pp. 6481-6488, 2009.
Pasquali, et al., "Abnormal level of retinoic acid in prostate cancer tissues," Journal of Clinical Endocrinology & Metabolism, vol. 81, No. 6, pp. 2186-2191, 1996.
Patel, et al., "Novel retinoic acid metabolism blocking agents endowed with multiple biological activities are efficient growth inhibitors of human breast and prostate cancer cells in vitro and a human breast tumor xenograft in nude mice," Journal of Medicinal Chemistry, vol. 47, No. 27, pp. 6716-6729, 2004.
Patel, et al., "Novel retinoic acid metabolism blocking agents have potent inhibitory activities on human breast cancer cells and tumour growth," British Journal of Cancer, vol. 96, No. 8, pp. 1204-1215, 2007.
Pautus, et al., "Design and synthesis of substituted imidazole and triazole N-phenylbenzo[d]oxazolamine inhibitors of retinoic acid metabolizing enzyme CYP26," Journal of Enzyme Inhibition and Medicinal Chemistry, vol. 24, No. 2, pp. 487-498, 2009.
Pautus, et al., "Synthesis and CYP26A1 inhibitory activity of 1-[benzofuran-2-yl-(4-alkyliaryl-phenyl)-methyl]-1H-triazoles," Bioorganic & Medicinal Chemistry, 14(11):3643-3653, 2006.
Pavez Lorié, et al., "Topical treatment with CYP26 inhibitor talarozole (R115866) dose dependently alters the expression of retinoid-regulated genes in normal human epidermis," British Journal of Dermatology, vol. 160, No. 1, pp. 26-36, 2009.
Pavez Lorié, et al., "Both all-trans retinoic acid and cytochrome P450 (CYP26) inhibitors affect the expression of vitamin A metabolizing enzymes and retinoid biomarkers in organotypic epidermis," Archives of Dermatological Research, vol. 301, No. 7, pp. 475-485, 2009.
Pavez Lorié, et al., "Expression of retinoid-regulated genes in lamellar ichthyosis vs. healthy control epidermis: changes after oral treatment with liarozole," Acta Dermato-Venereologica, vol. 89, No. 1, pp. 12-20, 2009.
PCT/US2014/051962, International Search Report and Written Opinion dated Feb. 27, 2015 for filed Aug. 20, 2014, 16 pages.
Pessayre, "Role of mitochondria in non-alcoholic fatty liver disease," Journal of Gastroenterology and Hepatology, vol. 22, Suppl 1, pp. S20-S27, 2007.
Petkovich, et al., "A human retinoic acid receptor which belongs to the family of nuclear receptors," Nature, vol. 330, No. 6147, pp. 444-450, 1987.
Pilkington, et al., "Acitretin. A review of its pharmacology and therapeutic use," Drugs, vol. 43, No. 4, pp. 597-627, 1992.
Piu, et al., "Identification of novel subtype selective RAR agonists," Biochemical Pharmacology, vol. 71, No. 1-2, pp. 156-162, 2005.
Pont, et al., "Ketoconazole blocks adrenal steroid synthesis," Annals of Internal Medicine, vol. 97, No. 3, pp. 370-372, 1982.

(56) References Cited

OTHER PUBLICATIONS

Prasad et al., "Ensemble modeling of substrate binding to cytochromes P450: analysis of catalytic differences between CYP1A orthologs," Biochemistry, vol. 46, No. 10, pp. 2640-2654, 2007.
Radominska-Pandya, et al., "Direct interaction of all-trans-retinoic acid with protein kinase C (PKC). Implications for PKC signaling and cancer therapy," Journal of Biological Chemistry, vol. 275, No. 29, pp. 22324-22330, 2000.
Ray, et al., "CYP26, a novel mammalian cytochrome P450, is induced by retinoic acid and defines a new family," Journal of Biological Chemistry, vol. 272, No. 30, pp. 18702-18708, 1997.
RD Bruno, et al., "Targeting cytochrome P450 enzymes: a new approach in anticancer drug development," Bioorganic & Medicinal Chemistry, vol. 15, No. 15, pp. 5047-5060, 2007.
Ren, et al., "Structure prediction and R115866 binding study of human CYP26A1: homology modelling, fold recognition, molecular docking and MD simulations," Molecular Simulation, vol. 34, No. 3, pp. 337-346, 2008.
Rigas, et al., "Constitutive variability in the pharmacokinetics of the natural retinoid, all-trans-retinoic acid, and its modulation by ketoconazole," Journal of the National Cancer Institute, vol. 85, No. 23, pp. 1921-1926, 1993.
Rigopoulos, et al., "The role of isotretinoin in acne therapy: why not as first-line therapy? facts and controversies," Clinics in Dermatolology, vol. 28, No. 1, pp. 24-30, 2010.
Ross, "Cellular metabolism and activation of retinoids: roles of cellular retinoid-binding proteins," FASEB Journal, vol. 7, No. 2, pp. 317-327, 1993.
Ross, "Vitamin A and retinoic acid in T cell-related immunity," American Journal of Clinical Nutrition, vol. 96, No. 5, pp. 1166S-1172S, 2012.
Ross, et al., "Cytochrome P450s in the regulation of cellular retinoic acid metabolism," Annual Review of Nutrition, vol. 31, pp. 65-87, 2011.
Ross, et al., "Multiple cytochrome P-450 genes are concomitantly regulated by vitamin A under steady-state conditions and by retinoic acid during hepatic first-pass metabolism," Physiological Genomics, vol. 43, No. 1, pp. 57-67, 2011.
Rost, et al., "A pan-PPAR ligand induces hepatic fatty acid oxidation in PPARalpha-/- mice possibly through PGC-1 mediated PPARdelta coactivation," Biochimica et Biophysica Acta, vol. 1791, No. 11, pp. 1076-1083, 2009.
Ruzicka et al., "Oral alitretinoin (9-cis-retinoic acid) therapy for chronic hand dermatitis in patients refractory to standard therapy: results of a randomized, double-blind, placebo-controlled, multicenter trial," Archives of Dermatology, 140(12):1453-1459, 2004.
Ryu et al., "Comparison of a label-free quantitative proteomic method based on peptide ion current area to the isotope coded affinity tag method," Cancer Informatics, vol. 6, pp. 243-255, 2008.
Saadeddin, et al., "Pharmacokinetics of the time-dependent elimination of all-trans-retinoic acid in rats," AAPS Journal, vol. 6, No. 1, pp. 1-9, 2004.
Sakuta, et al., "Marked improvement induced in photoaged skin of hairless mouse by ER36009, a novel RARγ-specific retinoid, but not by ER35794, an RXR-selective agonist," International Journal of Dermatology, 45(11):1288-1295, 2006.
Schmitt-Hoffmann et al., "Pharmacokinetic interactions between alitretinoin and ketoconazole or simvastatin or ciclosporin A," Clinical and Experimental Dermatology, vol. 36, pp. 24-28, 2011.
Schug, et al., "Opposing effects of retinoic acid on cell growth result from alternate activation of two different nuclear receptors," Cell, vol. 129, No. 4, pp. 723-733, 2007.
Schwartz, et al., "Inhibition of all-trans-retinoic acid metabolism by fluconazole in vitro and in patients with acute promyelocytic leukemia," Biochemical Pharmacology, vol. 50, No. 7, pp. 923-928, 1995.
Sedjo, et al., "Circulating endogenous retinoic acid concentrations among participants enrolled in a randomized placebo-controlled clinical trial of retinyl palmitate," Cancer Epidemiology, Biomarkers & Prevention, vol. 13, No. 11, Pt 1, pp. 1687-1692, 2004.
Seidmon, et al., "Phase I/II dose-escalation study of liarozole in patients with stage D, hormone-refractory carcinoma of the prostate," Annals of Surgical Oncology, vol. 2, No. 6, pp. 550-556, 1995.
Shaw, et al., "Retinoic acid is a high affinity selective ligand for the peroxisome proliferator-activated receptor beta/delta," Journal of Biological Chemistry, vol. 278, No. 43, pp. 41589-41592, 2003.
Shih, et al., "Nonenzymatic isomerization of 9-cis-retinoic acid catalyzed by sulfhydryl compounds," Drug Metabolism Disposition, vol. 25, No. 1, pp. 27-32, 1997.
Smets, et al., "Liarozole, an antitumor drug, modulates cytokeratin expression in the Dunning AT-6sq prostatic carcinoma through in situ accumulation of all-trans-retinoic acid," Prostate, vol. 27, No. 3, pp. 129-140, 1995.
Smith, et al., "The plasma transport and metabolism of retinoic acid in the rat," Biochemical Journal, vol. 132, No. 4, pp. 821-827, 1973.
Sonneveld, et al., "Human retinoic acid (RA) 4-hydroxylase (CYP26) is highly specific for all-trans-RA and can be induced through RA receptors in human breast and colon carcinoma cells," Cell Growth & Differentiation, vol. 9, No. 8, pp. 629-637, 1998.
[No Authors Listed] "Liarozole. Liarozole fumarate, Liazal, R 75251, R 85246," Drugs in R&D, PubMed: 10763459, vol. 2, No. 6, pp. 427-430, 1999.
Abu-Abed, et al., "Differential expression of the retinoic acid-metabolizing enzymes CYP26A1 and CYP26B1 during murine organogenesis," Mechanisms of Development, vol. 110, No. 1-2, pp. 173-177, 2002.
Abu-Abed, et al., "The retinoic acid-metabolizing enzyme, CYP26A1, is essential for normal hindbrain patterning, vertebral identity, and development of posterior structures," Genes & Development, vol. 15, No. 2, pp. 226-240, 2001.
Acevedo, et al., "Liarozole potentiates the cancer chemopreventive activity of and the up-regulation of gap junctional communication and connexin43 expression by retinoic acid and beta-carotene in 10T1/2 cells," Carcinogenesis, vol. 16, No. 9, pp. 2215-2222, 1995.
Achkar, et al., "Differences in the pharmacokinetic properties of orally administered all-trans-retinoic acid and 9-cis-retinoic acid in the plasma of nude mice," Drug Metabolism and Disposition, vol. 22, No. 3, pp. 451-458, 1994.
Afonja, et al., "RAR agonists stimulate SOX9 gene expression in breast cancer cell lines: evidence for a role in retinoid-mediated growth inhibition," Oncogene, vol. 21, No. 51, pp. 7850-7860, 2002.
Aggarwal, et al., "Nonclassical action of retinoic acid on the activation of the cAMP response element-binding protein in normal human bronchial epithelial cells," Molecular Biology of the Cell, vol. 17, No. 2, pp. 566-575, 2006.
Aharoni-Simon, et al., "Fatty liver is associated with impaired activity of PPARgamma-coactivator 1alpha (PGC1alpha) and mitochondrial biogenesis in mice," Laboratory Investigation, vol. 91, No. 7, pp. 1018-1028, 2011.
Ahluwalia, et al., "Distribution of labeled retinyl acetate and retinoic acid in rat and human testes. A possible site of retinyl acetate incorporation in rat testes," Journal of Nutrition, vol. 105, No. 4, pp. 467-474, 1975.
Ahmad, "Study on cytochrome P-450 dependent retinoic acid metabolism and its inhibitors as potential agents for cancer therapy," Scientia Pharmaceutica, vol. 79, No. 4, pp. 921-935, 2016.
Altucci et al., "Retinoic acid-induced apoptosis in leukemia cells is mediated by paracrine action of tumor-selective death ligand TRAIL," Nature Medicine, vol. 7, No. 6, pp. 680-686, 2001.
Altucci, et al., "RAR and RXR modulation in cancer and metabolic disease," Nature Reviews Drug Discovery, vol. 6, No. 10, pp. 793-810, 2007.
Amann, et al., "Regulation of gene expression by retinoids," Current Medicinal Chemistry, vol. 18, No. 9, pp. 1405-1412, 2011.
Amengual, et al., "Induction of carnitine palmitoyl transferase 1 and fatty acid oxidation by retinoic acid in HepG2 cells," International Journal of Biochemistry and Cell Biology, vol. 44, No. 11, pp. 2019-2027, 2012.

(56) References Cited

OTHER PUBLICATIONS

Amengual, et al., "Retinoic acid treatment increases lipid oxidation capacity in skeletal muscle of mice," Obesity (Silver Spring), vol. 16, No. 3, pp. 585-591, 2008.
Arnold, et al., "A sensitive and specific method for measurement of multiple retinoids in human serum with UHPLC-MS/MS," Journal of Lipid Research, vol. 53, No. 3, pp. 587-598, 2012.
Ashla, et al., "Genetic analysis of expression profile involved in retinoid metabolism in non-alcoholic fatty liver disease," Hepatology Research, vol. 40, No. 6, pp. 594-604, 2010.
Asselineau, et al., (Jun. 1989) "Retinoic acid improves epidermal morphogenesis," Developmental Biology, vol. 133, No. 2, pp. 322-335, 1989.
Attar, et al., "Cytochrome P450 2C8 and Flavin-containing Monooxygenases are Involved in the Metabolism of Tazarotenic Acid in Humans," Drug Metabolism & Disposition, vol. 31, No. 4, pp. 476-481, 2003.
Beard, et al., "Phenylcyclohexene and phenylcyclohexadiene substituted compounds having retinoid antagonist activity," Bioorganic & Medicinal Chemistry Letters, 11(6):765-768, 2001.
Bell, et al., "Retinol and retinyl esters in patients with alcoholic liver disease," Journal of Hepatology, vol. 8, No. 1, pp. 26-31, 1989.
Belosay, et al. (Dec. 2006) "Effects of novel retinoic acid metabolism blocking agent (VN/14-1) on letrozole-insensitive breast cancer cells," Cancer Research, 66(23):11485-11493, 2006.
Bennett, et al., "Hypercalcemia due to all-trans retinoic acid in the treatment of acute promyelocytic leukemia potentiated by voriconazole," Leukemia & Lymphoma, vol. 46, No. 12, pp. 1829-1831, 2005.
Berry, et al., "All-trans-retinoic acid represses obesity and insulin resistance by activating both peroxisome proliferation-activated receptor beta/delta and retinoic acid receptor," Molecular and Cellular Biology, vol. 29, No. 12, pp. 3286-3296, 2009.
Berry, et al., "Is PPARbeta/delta a Retinoid Receptor?" PPAR Research, 73256, 2007.
Berry, et al., "Signaling by vitamin A and retinol-binding protein in regulation of insulin responses and lipid homeostasis," Biochimica et Biophysica Acta, vol. 1821, No. 1, pp. 168-176, 2012.
Bershad, et al., "Changes in plasma lipids and lipoproteins during isotretinoin therapy for acne," New England Journal of Medicine, vol. 313, No. 16, pp. 981-985, 1985.
Berthelot, et al., "Bromation régiosélective en série aromatique. I: Monobromation en position para de phénols et d'aminés aromatiques par le tribromure de tétrabutylammonium," Canadian Journal of Chemistry, vol. 67, No. 12, pp. 2061-2066, 1989.
Berth-Jones, et al., "Treatment of psoriasis with oral liarozole: a dose-ranging study," British Journal of Dermatology, 143(6):1170-1176, 2000.
Betancourt, et al., "Mitochondrial-nuclear genome interactions in non-alcoholic fatty liver disease in mice," Biochemical Journal, vol. 461, No. 2, pp. 223-232, 2014.
Bhushan, et al., "Oral liarozole in the treatment of palmoplantar pustular psoriasis: a randomized, double-blind, placebo-controlled study," British Journal of Dermatology, 145(4):546-553, 2001.
Blomhoff, et al., "Overview of retinoid metabolism and function," Journal of Neurobiology, vol. 66, No. 7, pp. 606-630, 2006.
Boccardo, et al., "R75251 in prostate cancer patients in progression after first-line hormonal treatment," Tumori, vol. 80, No. 4, pp. 276-279, 1994.
Boehm, et al., "Synthesis and structure-activity relationships of novel retinoid X receptor-selective retinoids," Journal of Medicinal Chemistry, vol. 37, No. 18, pp. 2930-2941, 1994.
Bonet, et al., "Lipid metabolism in mammalian tissues and its control by retinoic acid," Biochimica et Biophysica Acta, vol. 1821, No. 1, pp. 177-189, 2012.
Bovenschen, et al., "Oral retinoic acid metabolism blocking agent Rambazole for plaque psoriasis: an immunohistochemical study," British Journal of Dermatology, vol. 156, No. 2, pp. 263-270, 2007.
Boylan, et al., "The level of CRABP-I expression influences the amounts and types of all-trans-retinoic acid metabolites in F9 teratocarcinoma stem cells," Journal of Biological Chemistry, vol. 267, No. 30, pp. 21486-21491, 1992.
Brelsford, et al., "Preventing and managing the side effects of isotretinoin," Seminars in Cutaneous Medicine and Surgery, vol. 27, No. 3, pp. 197-206, 2008.
Brown, et al., "Prediction of in vivo drug-drug interactions from in vitro data: factors affecting prototypic drug-drug interactions involving CYP2C9, CYP2D6 and CYP3A4," Clinical Pharmacokinetics, vol. 45, No. 10, pp. 1035-1050, 2006.
Bruynseels, et al., "R75251, a new inhibitor of steroid biosynthesis," Prostate, vol. 16, No. 4, pp. 345-357, 1990.
Budhu, et al., "Direct channeling of retinoic acid between cellular retinoic acid-binding protein II and retinoic acid receptor sensitizes mammary carcinoma cells to retinoic acid-induced growth arrest," Molecular and Cellular Biology, vol. 22, No. 8, pp. 2632-2641, 2002.
Buttrick, "Characterization of selective and potent inhibitors of the human retinoic acid hydroxylases CYP26A1 and CYP26B1," Master of Science thesis, University of Washington, 73 pages, 2012.
CAS Registry No. 101204-37-9 (retrieved on SciFinder Aug. 2016).
CAS Registry No. 102121-60-8 (retrieved on SciFinder Aug. 2016).
CAS Registry No. 104561-41-3 (retrieved on SciFinder Aug. 2016).
CAS Registry No. 110952-09-5 (retrieved on SciFinder Aug. 2016).
CAS Registry No. 110952-11-9 (retrieved on SciFinder Aug. 2016).
CAS Registry No. 110952-21-1 (retrieved on SciFinder Aug. 2016).
CAS Registry No. 110952-26-6 (retrieved on SciFinder Aug. 2016).
CAS Registry No. 110952-28-8 (retrieved on SciFinder Aug. 2016).

\* cited by examiner

SPECIFIC INHIBITORS OF CYTOCHROME P450 26 RETINOIC ACID HYDROXYLASE

CROSS-REFERENCE TO RELATED APPLICATIONS

This application claims priority to International Patent Application No. PCT/US2014/051962, filed Aug. 20, 2014, which claims priority to U.S. Provisional Application No. 61/867,892, filed Aug. 20, 2013, all of which are hereby incorporated herein by reference in their entireties.

STATEMENT OF GOVERNMENT SUPPORT

This invention was made with government support under UL1 TR000423, P30 NS055022, R41 AG046987, and R01 GM081569, awarded by the National Institutes of Health. The government has certain rights in the invention.

BACKGROUND OF THE INVENTION

Field of the Invention

The present disclosure is generally directed to compositions and methods for treating diseases that are ameliorated by the inhibition of CYP26 mediated retinoic acid metabolism.

Description of Related Art

Retinoic acid (RA), the active metabolite of vitamin A, is an important endogenous signaling molecule regulating cell cycle and maintenance of epithelia. RA isomers are also used as drugs to treat various cancers and dermatological diseases. However, the therapeutic uses of RA isomers are limited due to side effects such as teratogenicity and resistance to treatment, emerging mainly from autoinduction of RA metabolism. To improve the therapeutic usefulness of retinoids, RA metabolism blocking agents (RAMBAs) have been developed. These inhibitors generally target the cytochrome P450 (CYP) enzymes because RA clearance is predominantly mediated by P450s. Since the initial identification of inhibitors of RA metabolism, CYP26 enzymes have been characterized as the main enzymes responsible for RA clearance.

The CYP26A1 and CYP26B1 enzymes appear to be the predominant all-trans-retinoic acid (atRA) hydroxylases in humans, both in the liver and in extrahepatic tissues. In cell culture, differential expression of CYP26A1 changes the cells susceptibility to apoptosis, presumably via different metabolic capacity of the cells. Similarly, inhibition of P450 mediated atRA metabolism makes the cells more susceptible to proapoptotic effects of atRA. In acute promyelocytic leukemia patients receiving atRA therapy, therapy resistance and relapse has been attributed to CYP26 induction and increased atRA elimination in cancer cells. Whether any of the known CYP26A1 inhibitors also inhibit CYP26B1 is currently unknown and the pharmacological effects of selective CYP26A1 versus CYP26B1 inhibition have not been characterized.

SUMMARY OF THE INVENTION

The basic principle of development of CYP26 inhibitors is that endogenous RA concentrations will be increased in the presence of a CYP26 inhibitor, thus, potentiating the activity of endogenous RA in cell-type specific manner. This will reduce side effects compared to administration of RA and allow for more targeted therapy. In clinical trials, inhibitors of RA metabolism have been effective in treatment of acne and psoriasis and other dermatological conditions as well as in some cancers, such as acute promyelocytic leukemia (APL). But, no CYP26 inhibitor has yet been approved for clinical use. The present disclosure provides new and effective inhibitors of CYP26.

Thus, one aspect of the disclosure provides compounds of formula (I):

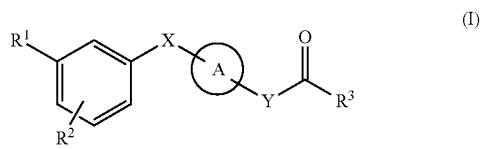

or a pharmaceutically acceptable salt thereof, wherein
A represents aryl optionally substituted with one, two, three, or four groups that are each independently halogen, cyano, nitro, $C_{1-6}$ alkyl, $C_{1-6}$ haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy;
X is a bond, —$CH_2$—, —$CHR^5$—, —C=$CHR^4$—, —$NR^4$—, —N=O—$R^4$—, —O—, —S—, —SO—, —$SO_2$—, —C(O)—, or —$C(NR^4)$—, or X is of formula

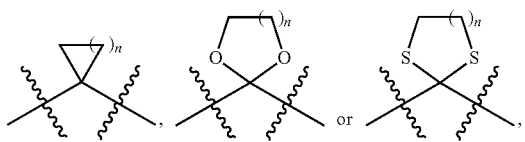

wherein
each n is independently 1, 2, or 3;
each $R^4$ is independently hydrogen or $C_{1-6}$ alkyl;
$R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl;
Y is $C_{1-6}$ alkylene, $C_{2-6}$ alkenylene, or $C_{2-6}$ alkylylene moiety;
$R^1$ is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl;
$R^2$ is hydrogen, halogen, $C_{1-6}$ alkyl, or —$OR^8$, where $R^8$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl;

or R¹ and R² together with the atoms to which they are attached form a $C_{3-12}$ cycloalkyl, heterocyclyl, aryl, or heteroaryl, each optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂; and R³ is hydrogen, $C_{1-6}$ alkyl, $C_{1-6}$ haloalkyl, —OR, —SR, or —NR₂, and each R is independently hydrogen, $C_{1-6}$ alkyl, $C_{2-6}$ alkenyl, $C_{1-6}$ haloalkyl, $C_{3-12}$ cycloalkyl, heterocyclyl, aryl, arylC₁₋₆ alkyl, heteroaryl, or heteroarylC₁₋₆ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁰, —SR⁰, —N(R⁰)₂, —C(O)R⁰, —C(O)OR⁰, —C(O)N(R⁰)₂, —S(O)₂R⁰, —OC(O)R⁰, —OC(O)OR⁰, —OC(O)N(R⁰)₂, —N(R⁰)C(O)R⁰, —N(R⁰)C(O)OR⁰, or —N(R⁰)C(O)N(R⁰)₂, wherein each R⁰ is independently hydrogen or $C_{1-6}$ alkyl.

In another aspect, the disclosure provides pharmaceutical compositions comprising one or more of compounds of the disclosure and a pharmaceutically acceptable carrier, diluent, or excipient.

In another aspect, the disclosure provides methods for treating diseases that are ameliorated by the inhibition of CYP26 mediated retinoic acid metabolism comprising providing to a patient in need of such treatment a therapeutically effective amount of either (a) one or more of compounds of formula (I), or (b) a pharmaceutical composition comprising one or more of compounds of formula (I) and a pharmaceutically acceptable excipient, carrier, or diluent.

In another aspect, the disclosure provides methods for treating diseases that are ameliorated by the inhibition of CYP26 mediated retinoic acid metabolism comprising providing to a patient in need of such treatment a therapeutically effective amount of either (a) one or more of compounds of formula (II), or (b) a pharmaceutical composition comprising one or more of compounds of formula (II) and a pharmaceutically acceptable excipient, carrier, or diluent, wherein formula (II) is:

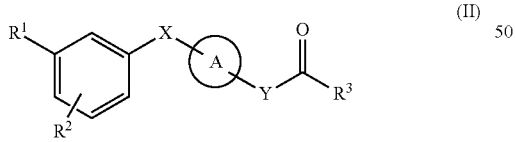

(II)

or a pharmaceutically acceptable salt thereof, wherein

A represents aryl optionally substituted with one, two, three, or four groups that are each independently halogen, cyano, nitro, $C_{1-6}$ alkyl, $C_{1-6}$ haloalkyl, —NH₂, —NH(C₁-C₆ alkyl), —N(C₁-C₆ alkyl)₂, —OH, C₁-C₆ alkoxy, and C₁-C₆ haloalkoxy;

X is a bond, —CH₂—, —CHR⁵, —C=CHR⁴—, —NR⁴—, —N=O—R⁴—, —O—, —S—, —SO—, —SO₂—, —C(O)—, —C(S)—, —C(CH₂)—, —C(NR⁴)—, —C(O)CH₂O—, —CH(OR⁴)CH₂O—, —C(NR⁴)CH₂O—, or —CH(N(R⁴)₂)CH₂O—, or X is of formula

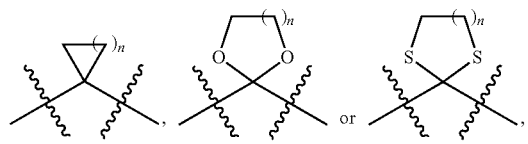

wherein each n is independently 1, 2, or 3;

each R⁴ is independently hydrogen or $C_{1-6}$ alkyl;

R⁵ is independently hydrogen, $C_{1-6}$ alkyl, or —OR⁶, where R⁶ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, arylC₁₋₆ alkyl, heteroaryl, or heteroarylC₁₋₆ alkyl;

Y is $C_{1-6}$ alkylene, $C_{2-6}$ alkenylene, or $C_{2-6}$ alkylylene moiety;

R¹ is $C_{1-6}$ alkyl, $C_{2-6}$ alkenyl, $C_{1-6}$ haloalkyl, $C_{3-12}$ cycloalkyl, heterocyclyl, aryl, arylC₁₋₆ alkyl, heteroaryl, or heteroarylC₁₋₆ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂, wherein each R⁷ is independently hydrogen or $C_{1-6}$ alkyl;

R² is hydrogen, halogen, $C_{1-6}$ alkyl, or —OR⁸, where R⁸ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, arylC₁₋₆ alkyl, heteroaryl, or heteroarylC₁₋₆ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂, wherein each R⁷ is independently hydrogen or $C_{1-6}$ alkyl;

or R¹ and R² together with the atoms to which they are attached form a $C_{3-12}$ cycloalkyl, heterocyclyl, aryl, or heteroaryl, each optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)—C(O)N(R⁷)₂; and R³ is hydrogen, $C_{1-6}$ alkyl, $C_{1-6}$ haloalkyl, —OR, —SR, or —NR₂, and each R is independently hydrogen, $C_{1-6}$ alkyl, $C_{2-6}$ alkenyl, $C_{1-6}$ haloalkyl, $C_{3-12}$ cycloalkyl, heterocyclyl, aryl, arylC₁₋₆ alkyl, heteroaryl, or heteroarylC₁₋₆ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁰, —SR⁰, —N(R⁰)₂, —C(O)R⁰, —C(O)OR⁰, —C(O)N(R⁰)₂, —S(O)₂R⁰, —OC(O)R⁰, —OC(O)OR⁰, —OC(O)N(R⁰)₂, —N(R⁰)C(O)R⁰, —N(R⁰)C(O)OR⁰, or —N(R⁰)C(O)N(R⁰)₂, wherein each R⁰ is independently hydrogen or $C_{1-6}$ alkyl.

In other aspect, the diseases ameliorated by the inhibition of CYP26 mediated retinoic acid metabolism are cancer, such as (but not limited to) acute promyelocytic leukaemia, neuroblastoma, basal cell and squamous cell carcinomas, prostate cancer, lung cancer, and breast cancer; neurodegenerative diseases, such as (but not limited to) Alzheimer's disease, Parkinson's disease and stroke; and dermatological disorders, such as (but not limited to) acne, psoriasis, and ichthyosis.

In further aspect of the present disclosure, the compounds of formula (I) or (II) are capable of selective inhibition of CYP26A1 over CYP26B1.

DETAILED DESCRIPTION OF THE INVENTION

Figure 1:
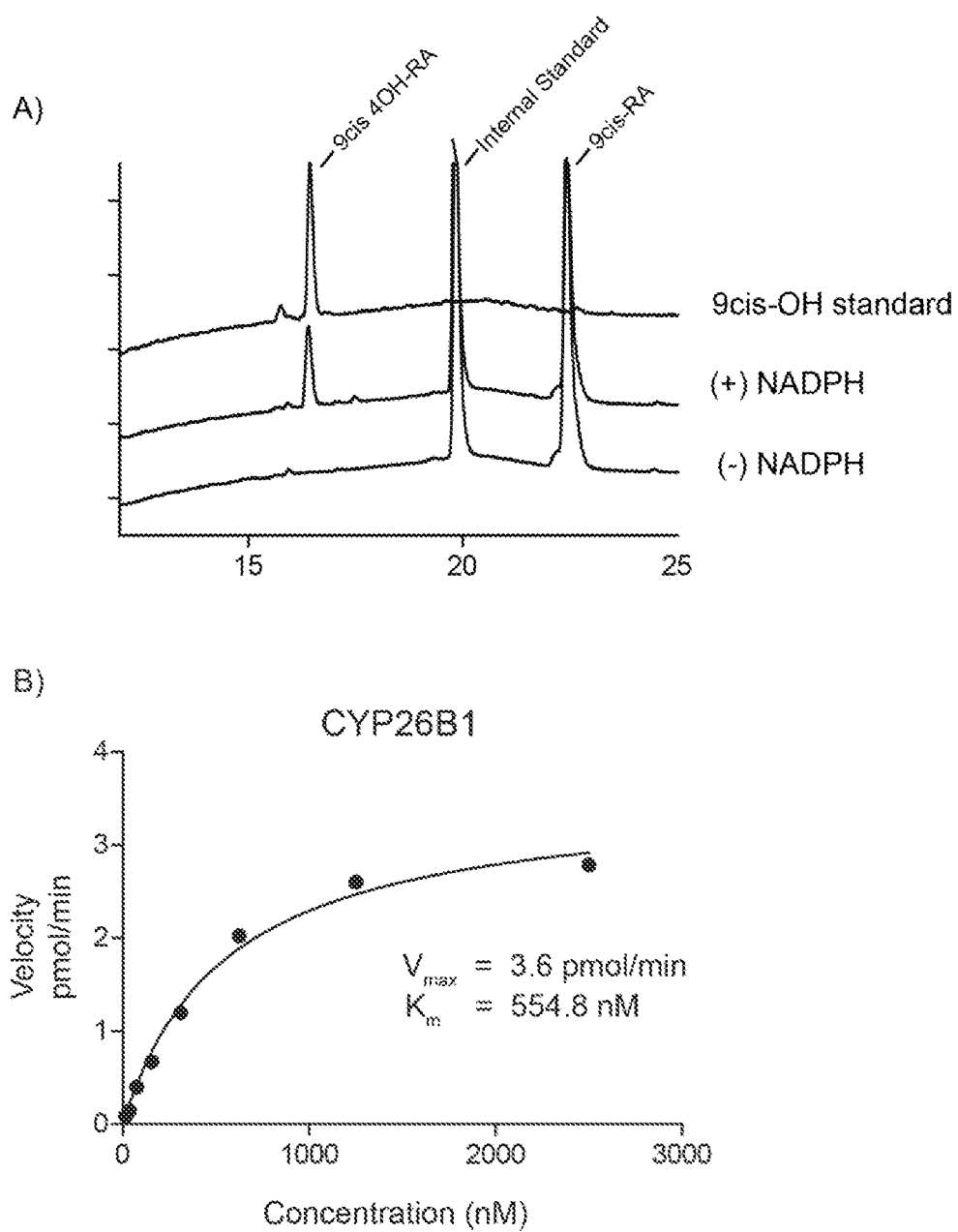
FIG. 1 shows characterization of 9cis-RA as a substrate of CYP26B1. UV chromatograms of 9cisRA incubated with CYP26B1 in the presence and absence of NADPH are shown in panel A. Panel B shows the determination of the Michaelis Menten kinetic constants for 9-cis-4OH-RA formation from 9-cis-RA by CYP26B1.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In view of the present disclosure, the compounds described herein can be configured by the person of ordinary skill in the art to meet the desired need. In general, the disclosed compounds provide improvements in treatment of diseases that are ameliorated by the inhibition of CYP26 mediated retinoic acid metabolism. For example, in certain aspects, the compounds of the disclosure are effective against disorders, including cancers, such as (but not limited to) acute promyelocytic leukaemia, neuroblastoma, basal cell and squamous cell carcinomas, lung, prostate cancer, and breast cancer; neurodegenerative diseases, such as (but not limited to) Alzheimer's disease, Parkinson's disease and stroke; and dermatological disorders, such as (but not limited to) acne, psoriasis, and ichthyosis. Furthermore, the compounds of the disclosure may have the advantage of avoiding side effects usually caused by retinoids, such as skin irritation, teratogenesis, and/or hypervitaminosis-A. Finally, the compounds of the disclosure are capable of selective inhibition of CYP26A1 over CYP26B1.

In one embodiment, the compounds of formula (I) or (II) are those where A is optionally substituted phenyl. Such compound can be represented by formula:

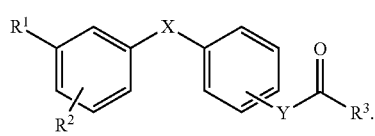

In other embodiments, when A is optionally substituted phenyl, compounds are of formula:

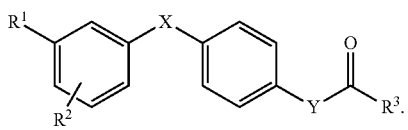

In some other embodiments, when A is optionally substituted phenyl, compounds are of formula:

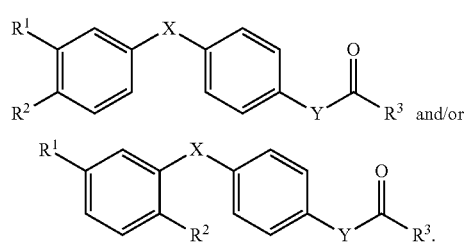

In one embodiment, the compounds of formula (I) or (II) are those where A is optionally substituted naphthyl. Such compound can be represented by formula:

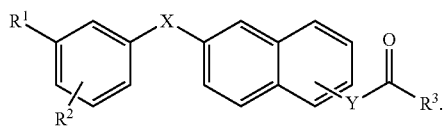

In other embodiments, when A is optionally substituted naphthyl, compounds are of formula:

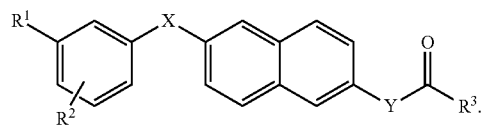

In some other embodiments, when A is optionally substituted naphthyl, compounds are of formula:

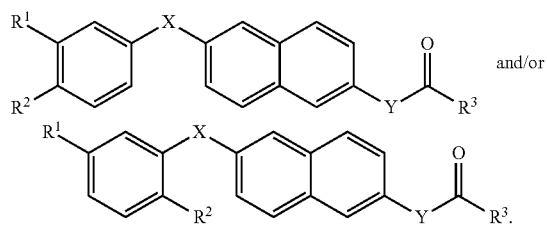

In one embodiment, the compounds of formula (I) or (II) and any preceding embodiment are those where:

X is —CH$_2$—, —CHR$^5$—, —C═CHR$^4$—, —NR$^4$—, —N═O—R$^4$—, —O—, —S—, —SO—, —SO$_2$—, —C(O)—, or —C(NR$^4$)—, or X is of formula

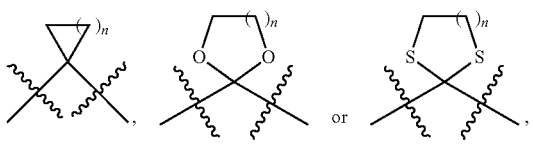

wherein
each n is independently 1, 2, or 3;
each $R^4$ is independently hydrogen or $C_{1-6}$ alkyl; and
$R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl.

In another embodiment, the compounds of formula (I) or (II) and any preceding embodiment are those where X is —$CH_2$—, —$CHR^5$—, —C=$CHR^4$—, —$NR^4$—, —N=O—$R^4$—, —O—, —S—, —SO—, —$SO_2$—, —C(O)—, or —C($NR^4$)—, wherein
each $R^4$ is independently hydrogen or $C_{1-6}$ alkyl; and
$R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl.

Other particularly useful compounds of formula (I) or (II) and any preceding embodiment are those where X is —$CH_2$— or —$CHR^5$—, wherein $R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl. In other embodiments, X is —$CH_2$—. Compounds of formula (I) or (II), in one embodiment, include those where X is —$NR^4_2$—, —O—, —S—, —SO—, —$SO_2$—, —C(O)—, or —C($NR^4$)—, wherein each $R^4$ is independently hydrogen or $C_{1-6}$ alkyl. Certain embodiments of the compounds of the disclosure include those where X is —O—, —S—, —SO—, —$SO_2$—, —C(O)—, or —C($NR^4$)—. In some embodiments, X is —O—, —S—, —SO—, or —$SO_2$—. In other embodiments, X is —O—. In one embodiment of the disclosure, the compounds are those where X is —S—, —SO—, or —$SO_2$—. In another embodiment of the disclosure, the compounds are those where X is —C(O)—.

Other particularly useful compounds of formula (I) or (II) and any preceding embodiment are those where X is of formula

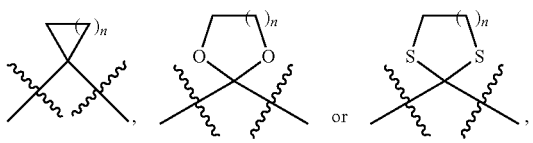

and each n is independently 1 or 2. In one embodiment, each n is independently 1. In another embodiment, X is

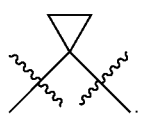

in yet another embodiment, X is of formula

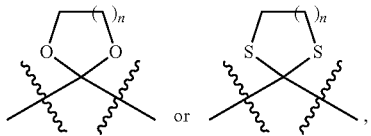

and each n is independently 1 or 2; or each n is independently 1.

Other particularly useful compounds of formula (I) or (II) are those where X is a bond.

Certain embodiments of the compounds of the disclosure include those where X is a bond, —$CH_2$—, —NH—, —S—, —$SO_2$—, —C(O)—,

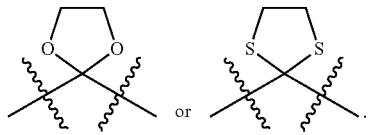 [SMILES: *C1(*)OCCO1 ; *C1(*)SCCS1]

Certain other embodiments of the compounds of the disclosure include those where X is —$CH_2$—, —NH—, —S—, —$SO_2$—, —C(O)—,

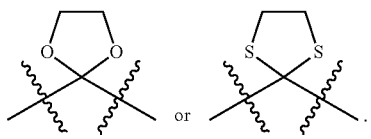

Compounds of formula (I) or (II) and any previous embodiment include compounds wherein Y is $C_{1-6}$ alkylene or $C_{2-6}$ alkenylene. In some embodiments, Y is $C_{1-4}$ alkylene or $C_{2-4}$ alkenylene. In some other embodiments, Y is $C_{1-4}$ alkylene. For example, Y may be methylene, ethylene, or propylene. In other embodiments, Y is methylene and/or ethylene. In one embodiment of the disclosure, the compounds are those where Y is $C_{2-4}$ alkenylene. In one embodiment, Y is —CH=CH—, —$CH_2$CH=CH—, or —CH=CHCH$_2$—.

Compounds of formula (I) or (II) and any previous embodiment include compounds wherein Y is methylene, ethylene, or —CH=CH—.

Other particularly useful compounds of formula (I) or (II) and any preceding embodiment are those where $R^3$ is hydrogen, $C_{1-6}$ alkyl, —OR, or —NR$_2$, and each R is independently hydrogen, $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^o$, —$SR^o$, —$N(R^o)_2$, —$C(O)R^o$, —$C(O)OR^o$, —$C(O)N(R^o)_2$, —$S(O)_2R^o$, —$OC(O)R^o$, —$OC(O)OR^o$, —$OC(O)N(R^o)_2$, —$N(R^o)C(O)R^o$, —$N(R^o)C(O)OR^o$, or —$N(R^o)C(O)N(R^o)_2$, wherein each $R^o$ is independently hydrogen or $C_{1-6}$ alkyl. In some embodiments, $R^3$ is hydrogen or $C_{1-6}$ alkyl. In other embodiments, $R^3$ is hydrogen. In one embodiment of the disclosure, the compounds are those where $R^3$ is $C_{1-6}$ alkyl. For example, $R^3$ may be methyl, ethyl, propyl, isopropyl, butyl, secbutyl, isobutyl, and tertbutyl. In one embodiment, $R^3$ may be methyl, ethyl, propyl, or isopropyl. In a particular embodiment, $R^3$ is methyl.

Certain other embodiments of the compounds of the disclosure (and any preceding embodiments) include those where $R^3$ is $-NR_2$. In some embodiments, each R is independently hydrogen or $C_{1-6}$ alkyl optionally substituted with one, two, three, or four groups that are each independently halogen, cyano, nitro, $C_{1-6}$ alkyl, $C_{1-6}$ haloalkyl, $-OR^O$, $-SR^O$, $-N(R^O)_2$, $-C(O)R^O$, $-C(O)OR^O$, $-C(O)N(R^O)_2$, $-S(O)_2R^O$, $-OC(O)R^O$, $-OC(O)OR^O$, $-OC(O)N(R^O)_2$, $-N(R^O)C(O)R^O$, $-N(R^O)C(O)OR^O$, or $-N(R^O)C(O)N(R^O)_2$, wherein each $R^O$ is independently hydrogen or $C_{1-6}$ alkyl. In some embodiments, each R is independently hydrogen or $C_{1-6}$ alkyl. In some other embodiments, each R is independently hydrogen or methyl.

Other embodiments of the compounds of the disclosure (and any preceding embodiments) include those where $R^3$ is $-OR$. In some embodiments, R is hydrogen, $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $-OR^O$, $-SR^O$, $-N(R^O)_2$, $-C(O)R^O$, $-C(O)OR^O$, $-C(O)N(R^O)_2$, and $-S(O)_2R^O$, wherein each $R^O$ is independently hydrogen or $C_{1-6}$ alkyl. In other embodiments, R is hydrogen, $C_{1-6}$ alkyl, $C_{1-6}$ haloalkyl, $C_{3-12}$ cycloalkyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $-OR^O$, $-SR^O$, $-N(R^O)_2$, $-C(O)R^O$, $-C(O)OR^O$, $-C(O)N(R^O)_2$, and $-S(O)_2R^O$, wherein each $R^O$ is independently hydrogen or $C_{1-6}$ alkyl. In yet other embodiments, R is hydrogen, $C_{1-6}$ alkyl, $C_{1-6}$ haloalkyl, or aryl$C_{1-6}$ alkyl, wherein the alkyl and arylalkyl are optionally substituted with one, two, three, or four groups that are each independently halogen, cyano, nitro, $C_{1-6}$ alkyl, $C_{1-6}$ haloalkyl, $-OR^O$, $-SR^O$, $-N(R^O)_2$, $-C(O)R^O$, $-C(O)OR^O$, $-C(O)N(R^O)_2$, and $-S(O)_2R^O$, wherein each $R^O$ is independently hydrogen or $C_{1-6}$ alkyl.

Some particularly useful compounds of formula (I) or (II) and any preceding embodiment are those where $R^3$ is $-OR$, and R is hydrogen or $C_{1-6}$ alkyl. In one embodiment, R is hydrogen. In another embodiment, R is $C_{1-4}$ alkyl. For example, R may be methyl, ethyl, propyl, isopropyl, butyl, secbutyl, isobutyl, and tertbutyl. In one embodiment, R may be methyl, ethyl, propyl, or isopropyl. In a particular embodiment, R is methyl. In another embodiment, R is hydrogen, methyl, ethyl, propyl, or butyl.

Some other particularly useful compounds of formula (I) or (II) and any preceding embodiment are those where $R^3$ is $-OR$, and R is aryl$C_{1-6}$ alkyl. For example, R may be benzyl.

In another embodiment, the compounds of formula (I) or (II) and any preceding embodiment are those where $R^1$ and $R^2$ together with the atoms to which they are attached form a $C_{3-12}$ cycloalkyl, heterocyclyl, aryl, or heteroaryl, each optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$. For example, one embodiment provides compounds where $R^1$ and $R^2$ together with the atoms to which they are attached form a $C_{3-12}$ cycloalkyl, optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$. Another embodiment provides compounds where $R^1$ and $R^2$ together with the atoms to which they are attached form a cyclohexane, optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$. Some particularly useful compounds are those wherein $R^1$ and $R^2$ together with the atoms to which they are attached form a cyclohexane substituted with four $C_{1-6}$ alkyl groups. For example, $R^1$ and $R^2$ together with the atoms to which they are attached form:

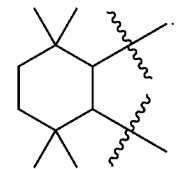 [SMILES: *C1C(*)C(C)(C)CCC1(C)C]

In another embodiment, the compounds of formula (I) or (II) and any preceding embodiment are those where $R^1$ and $R^2$ represent:
$R^1$ is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$, wherein each $R^7$ is independently hydrogen or $C_{1-6}$ alkyl; and
$R^2$ is hydrogen, halogen, $C_{1-6}$ alkyl, or $-OR^8$, where $R^8$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$, wherein
each $R^7$ is independently hydrogen or $C_{1-6}$ alkyl.
Some particularly useful compounds this embodiment are those where $R^1$ is $C_{1-6}$ alkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $-OR^7$, $-SR^7$, $-N(R^7)_2$, $-C(O)R^7$, $-C(O)OR^7$, $-C(O)N(R^7)_2$, $-S(O)_2R^7$, $-OC(O)R^7$, $-OC(O)OR^7$, $-OC(O)N(R^7)_2$, $-N(R^7)C(O)R^7$, $-N(R^7)C(O)OR^7$, or $-N(R^7)C(O)N(R^7)_2$, wherein each $R^7$ is independently hydrogen or $C_{1-6}$ alkyl. Other particularly useful compounds are those wherein $R^1$ is $C_{1-6}$ alkyl, $C_{3-12}$ cycloalkyl, or aryl$C_{1-6}$ alkyl, wherein the alkyl and arylalkyl, heteroaryl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl. In another embodiment, $R^1$ is $C_{1-6}$ alkyl or $C_{3-12}$ cycloalkyl, each optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl.

In one embodiment, the compounds of formula (I) or (II) and any preceding embodiment are those wherein $R^1$ is optionally substituted $C_{1-6}$ alkyl. In one embodiment, $R^1$ is unsubstituted $C_{1-6}$ alkyl. For example, $R^1$ may be methyl, ethyl, propyl, isopropyl, butyl, secbutyl, isobutyl, and tert-butyl. In one embodiment, $R^1$ is tert-butyl.

In one embodiment, the compounds of formula (I) or (II) and any preceding embodiment are those wherein $R^1$ is optionally substituted $C_{3-12}$ cycloalkyl. In one embodiment, $R^1$ is unsubstituted $C_{3-12}$ cycloalkyl. In one embodiment, for example, $R^1$ is adamantyl.

Another embodiment provides the compounds of formula (I) or (II) and any preceding embodiment wherein $R^2$ is halogen, $C_{1-6}$ alkyl, or —$OR^8$. Some particularly useful compounds this embodiment are those where $R^2$ is halogen or $C_{1-6}$ alkyl. Some other particularly useful compounds this embodiment are those where $R^2$ is —$OR^8$. In one embodiment, $R^8$ is selected from the group consisting of hydrogen, $C_{1-6}$ alkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl. In another embodiment, $R^8$ is selected from the group consisting of hydrogen, $C_{1-6}$ alkyl, or aryl$C_{1-6}$ alkyl, wherein the alkyl and arylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl. In yet another embodiment, $R^8$ is of hydrogen or $C_{1-6}$ alkyl.

In one embodiment, the compounds any preceding embodiment are those wherein $R^2$ is —$OR^8$, and $R^8$ is of hydrogen. In another embodiment, the compounds any preceding embodiment are those wherein $R^2$ is —$OR^8$, and $R^8$ is of $C_{1-6}$ alkyl. In another embodiment, the compounds any preceding embodiment are those wherein $R^2$ is —$OR^8$, and $R^8$ is of hydrogen or methyl. In yet another embodiment, the compounds any preceding embodiment are those wherein $R^2$ is —$OR^8$, and $R^8$ is of aryl$C_{1-6}$ alkyl. For example, $R^8$ may be benzyl. In yet another embodiment, the compounds any preceding embodiment are those wherein $R^2$ is —$OR^8$, and $R^8$ is hydrogen, $C_{1-6}$ alkyl, or benzyl.

The compounds of the disclosure are capable of inhibiting the activity of CYP26, and consequently acting as an RA metabolism blocking agents. Inhibition of CYP26 may be either in vivo and/or in vitro. Accordingly, the disclosure provides methods for treating diseases that are ameliorated by the inhibition of CYP26 mediated retinoic acid metabolism comprising providing to a patient in need of such treatment a therapeutically effective amount of either a compound of the disclosure (e.g., compounds formula (I) or (II) or any preceding embodiment), or a pharmaceutical composition comprising one or more of compounds of the disclosure. The diseases ameliorated by the inhibition of CYP26 mediated retinoic acid metabolism are cancer, such as (but not limited to) acute promyelocytic leukaemia, neuroblastoma, basal cell and squamous cell carcinomas, prostate cancer, lung cancer, and breast cancer; neurodegenerative diseases, such as (but not limited to) Alzheimer's disease, Parkinson's disease and stroke; and dermatological disorders, such as (but not limited to) acne, psoriasis, and ichthyosis.

The disclosure also provides methods for selectively inhibiting CYP26A1 over CYP26B1, comprising providing to a patient a therapeutically effective amount of either a compound of the disclosure (e.g., compounds formula (I) or (II) or any preceding embodiment), or a pharmaceutical composition comprising one or more of compounds of the disclosure.

The disclosure also provides methods for treating diseases that are ameliorated by administration of retinoic acid comprising providing to a patient in need of such treatment a therapeutically effective amount of either a compound of the disclosure (e.g., compounds formula (I) or (II) or any preceding embodiments) in combination with retinoic acid, or a pharmaceutical composition comprising one or more of compounds of the disclosure in combination with retinoic acid.

As used herein, the term "subject", "individual," or "patient," used interchangeably, refers to any animal, including mammals, such as mice, rats, other rodents, rabbits, dogs, cats, birds, swine, horses, livestock (e.g., pigs, sheep, goats, cattle), primates or humans. In one embodiment, the patient is a human.

As used here, a subject "in need thereof" refers to a subject that has the disorder or disease to be treated or is predisposed to or otherwise at risk of developing the disease or disorder.

As used here, the terms "treatment" and "treating" means:
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
(v) eliciting the referenced biological effect.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The pharmaceutical compositions described herein generally comprise a combination of one or more of compounds described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In one embodiment, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Definitions

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_{1-6}$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $-(CH_2)_w-$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, and acridin-9-yl.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxido-thiomorpholinyl(thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzathien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "nitro" as used herein, means a —$NO_2$ group.

The term "oxo" as used herein means a ═O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a ═S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

EXAMPLES

Unless otherwise stated, all chemicals were purchased from commercial suppliers and used without further purification. Inhibitors were synthesized through several different routes, as represented in Schemes 1-8.

Scheme 1

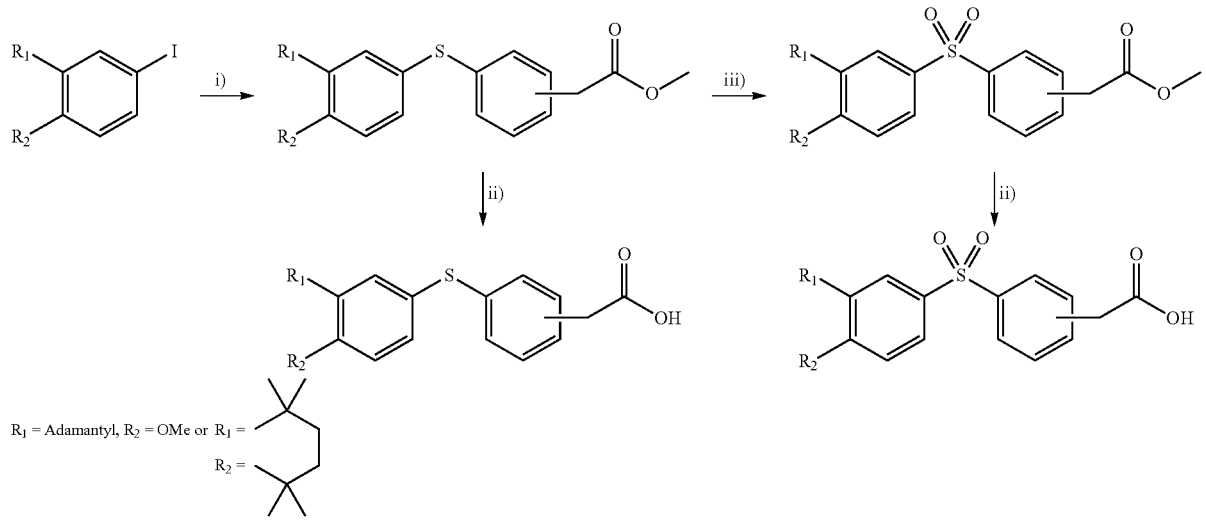

i) 3- or 4-mercaptophenylacetic acid methyl ester, borohydride, polymer supported, (bpy)₂ NiBr₂, dioxane, ButOH, 130-145° C. 3 h 00 to 5 h 00;
ii) LiOH, 1N, THF, H₂O, r.t. 12 h; iii) oxone, H₂O, MeOH, 0° C. to r.t., 12 h.

Example 1: Methyl 2-(4-{[3-(adamantan-1-yl)-4-methoxyphenyl]sulfanyl}phenyl)-acetate (a) 1-(5-iodo-2-methoxyphenyl)adamantane 1-(5-iodo-2-methoxyphenyl)adamantane was prepared according to modified procedures of Kalvinsh et al. (WO2008086942A2) and Sarshar (WO2005108338A1), both incorporated herein by reference. Briefly, sulfuric acid (1 mmol) was slowly added to a solution of 1-adamantanol (1 mmol) and 4-iodoanisole (1.5 mmol) in dichloromethane (20 mL). The mixture was stirred during 48 hours and then poured in water (50 mL). A solution of saturated sodium bicarbonate was added until pH=8. The organic layer was extracted with dichloromethane (3×100 mL) and washed with a 10% sodium sulfite aqueous solution (3×50 mL). After evaporation of volatile, the organic crude was purified by chromatography (cyclohexane/dichloromethane): (95/5) to (75/25) to afford a white powder (65%). mp=135° C. ¹H NMR (400 MHz, CHLOROFORM-d) δ ppm 1.75 (s, 6H), 2.04 (s, 10H), 3.79 (s, 3H), 6.62 (d, J=9.16 Hz, 1H), 7.40-7.50 (m, 2H).

(b) methyl 2-(4-sulfanylphenyl)acetate

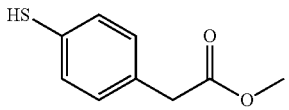

To a solution of 2-(4-sulfanylphenyl)acetic acid (980 mg, 5.8 mmol) in methanol (20 mL), was added conc. sulfuric acid (0.03 mL). The solution was stirred to reflux for 3 hours and then at r.t. overnight. After evaporation of the volatiles, conc. NaHCO₃ was added until pH=8 and the solution was extracted with ethyl acetate (3×50 mL). The organic layers were combined, dried over CaSO4 and evaporated. The crude was purified by column chromatography using the following gradient system, (cyclohexane/ethyl acetate): (93/7) to (60/40), to afford a colorless oil (920 mg, 88%). ¹H NMR (400 MHz, CHLOROFORM-d) δ ppm 3.43 (s, 1H), 3.56 (s, 2H), 3.68 (s, 3H), 7.14 (d, J=8.16 Hz, 2H), 7.23 (d, J=8.16 Hz, 2H).

(c) methyl 2-(4-{[3-(adamantan-1-yl)-4-methoxyphenyl]sulfanyl}phenyl)acetate

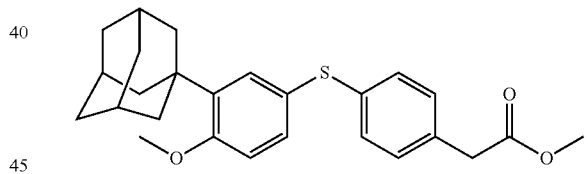

To a mixture of methyl 2-(4-sulfanylphenyl)acetate (130 mg, 0.71 mmol, 1 eq.) and 2-(1-adamantyl)-4-iodoanisole (262 mg, 0.71 mmol, 1 eq.) in dioxane (5 mL) and butanol (5 mL), were added the borohydride, polymer supported (650 mg, 2.5-5 mmol/g, 3 eq.) and (bpy)₂NiBr₂ (70 mg, 0.2 eq.). The mixture was heated to 145° C. under an atmosphere of nitrogen. The polymer beads were removed by filtration, and the mixture was concentrated to dryness before purification by flash chromatography using the following gradient system, (cyclohexane/dichloromethane): (20/80) to (0/100) afforded a colorless oil (120 mg, 14%) as a mixture of methyl 2-(4-{[3-(adamantan-1-yl)-4-methoxyphenyl]sulfanyl}phenyl)acetate and butyl 2-(4-{[3-(adamantan-1-yl)-4-methoxyphenyl]sulfanyl}phenyl)acetate (12%). ¹H NMR (400 MHz, CHLOROFORM-d) δ ppm 1.75 (s, 6H), 2.06 (s, 9H), 3.56 (s, 2H), 3.68 (s, 3H), 3.84 (s, 3H), 6.85 (d, J=8.41 Hz, 1H), 7.05-7.18 (m, 4H), 7.28 (d, J=8.41 Hz, 1H), 7.35 (br. s., 1H).

Example 2: Butyl 2-(4-{[3-(adamantan-1-yl)-4-methoxyphenyl]sulfanyl}phenyl)-acetate

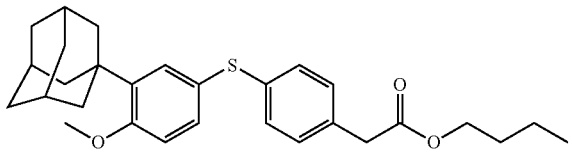 [SMILES: CCCCOC(=O)Cc1ccc(Sc2ccc(OC)c(C34CC5CC(CC(C5)C3)C4)c2)cc1]

butyl 2-(4-{[3-(adamantan-1-yl)-4-methoxyphenyl]sulfanyl}phenyl)acetate was obtained in example 1(c). $^1$H NMR (400 MHz, CHLOROFORM-d) δ ppm 0.90 (t, J=7.09 Hz, 3H), 1.27-1.39 (m, 2H), 1.52-1.56 (m, 2H), 2.06 (s, 9H), 3.56 (s, 2H), 3.84 (s, 3H), 4.07 (t, J=6.59 Hz, 2H), 6.85 (d, J=8.41 Hz, 1H), 7.05-7.18 (m, 4H), 7.28 (d, J=8.41 Hz, 1H), 7.35 (br. s., 1H).

Example 3: 2-(4-{[3-(adamantan-1-yl)-4-methoxyphenyl]sulfanyl}phenyl)acetic Acid

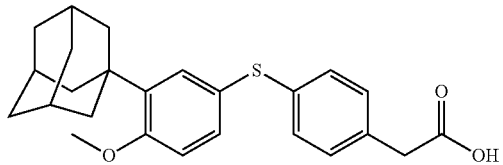 [SMILES: COc1ccc(Sc2ccc(CC(=O)O)cc2)cc1C12CC3CC(CC(C3)C1)C2]

To a solution of the mixture of methyl 2-(4-{[3-(adamantan-1-yl)-4-methoxyphenyl]sulfanyl}phenyl)acetate and butyl 2-(4-{[3-(adamantan-1-yl)-4-methoxyphenyl]sulfanyl}phenyl) (60 mg, 0.118 mmol) in THF (6 mL), was added 440 μL of a 1N solution of lithium hydroxide in water. The reaction was stirred at room temperature overnight. After acidification with 1N HCl until pH=1, the crude was extracted with DCM. The organic layers were combined, dried over Ca$_2$SO$_4$ and concentrated to afford a white solid, without any further purification (57 mg, 99%). mp=132-134° C. $^1$H NMR (400 MHz, CHLOROFORM-d) δ ppm 1.75 (s, 6H), 2.06 (s, 9H), 3.58 (s, 2H), 3.84 (s, 3H), 6.85 (d, J=8.41 Hz, 1H), 7.05-7.18 (m, 4H), 7.29 (dd, J=8.41, 1.88 Hz, 1H), 7.35 (d, J=1.88 Hz, 1H). HRMS (TOF MS ES−) for C25H27O3S$^−$ (M−H)$^−$ calcd. 407.1681, found 407.1695.

Example 4: Methyl 2-(3-{[3-(adamantan-1-yl)-4-methoxyphenyl]sulfanyl}phenyl)-acetate (a) methyl 2-(3-sulfanylphenyl)acetate

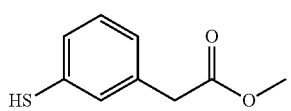

Methyl 2-(3-sulfanylphenyl)acetate was prepared according to example 1(b) starting from 1.16 g of 2-(3-sulfanylphenyl)acetic acid. A colorless oil was obtained (1.2 g, 95%), $^1$H NMR (400 MHz, CHLOROFORM-d) δ ppm 3.45 (s, 1H), 3.56 (s, 2H), 3.69 (s, 3H), 7.06 (d, J=5.77 Hz, 1H), 7.15-7.22 (m, 3H).

(b) Methyl 2-(3-{[3-(adamantan-1-yl)-4-methoxyphenyl]sulfanyl}phenyl)acetate

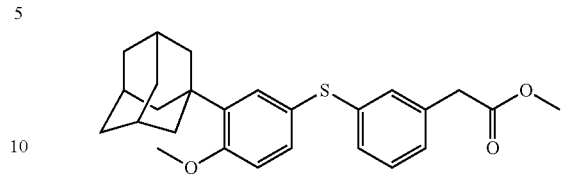

Methyl 2-(3-{[3-(adamantan-1-yl)-4-methoxyphenyl]sulfanyl}phenyl)acetate was prepared according to example 1(c) starting from 180 mg of methyl 2-(3-sulfanylphenyl)acetate. A colorless oil (205 mg, 50%) was obtained as a mixture of methyl 2-(3-{[3-(adamantan-1-yl)-4-methoxyphenyl]sulfanyl}phenyl)acetate and butyl 2-(3-{[3-(adamantan-1-yl)-4-methoxyphenyl]sulfanyl}phenyl)acetate (25%). $^1$H NMR (400 MHz, CHLOROFORM-d) δ ppm 1.76 (s, 6H), 2.06 (s, 9H), 3.55 (s, 2H), 3.67 (s, 3H), 3.85 (s, 3H), 6.86 (d, J=8.28 Hz, 1H), 6.98-7.07 (m, 2H), 7.09 (s, 1H), 7.14-7.22 (m, 1H), 7.30 (d, J=8.41 Hz, 1H), 7.35 (s, 1H).

Example 5: Butyl 2-(3-{[3-(adamantan-1-yl)-4-methoxyphenyl]sulfanyl}phenyl)acetate

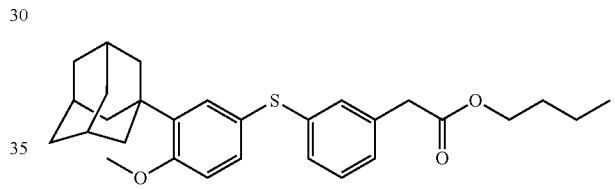

Butyl 2-(3-{[3-(adamantan-1-yl)-4-methoxyphenyl]sulfanyl}phenyl)acetate was obtained in example 4. $^1$H NMR (400 MHz, CHLOROFORM-d) δ ppm 0.91 (t, J=7.09 Hz, 3H), 1.29-1.38 (m, 2H), 1.55-1.62 (m, 2H), 1.76 (s, 6H), 2.06 (s, 9H), 3.55 (s, 2H), 3.85 (s, 3H), 4.07 (t, J=6.71 Hz, 2H), 6.86 (d, J=8.28 Hz, 1H), 6.98-7.07 (m, 2H), 7.09 (s, 1H), 7.14-7.22 (m, 1H), 7.30 (d, J=8.41 Hz, 1H), 7.35 (s, 1H).

Example 6: 2-(3-{[3-(Adamantan-1-yl)-4-methoxyphenyl]sulfanyl}phenyl)acetic Acid

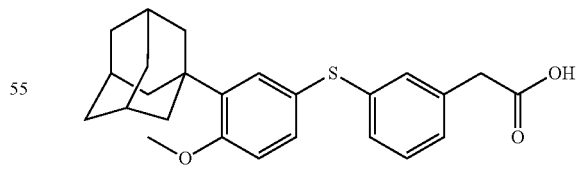

2-(3-{[3-(adamantan-1-yl)-4-methoxyphenyl]sulfanyl}phenyl)acetic acid was prepared according to example 3 using 50 mg of the mixture of methyl 2-(3-{[3-(adamantan-1-yl)-4-methoxyphenyl]sulfanyl}phenyl)acetate and butyl 2-(3-{[3-(adamantan-1-yl)-4-methoxyphenyl]sulfanyl}phenyl)acetate. A white solid was obtained (45 mg, 94%). mp=134° C. $^1$H NMR (400 MHz, CHLOROFORM-d) δ ppm 1.75 (s, 6H) 1.96-2.02-2.10 (m, 9H), 3.56

(s, 2H), 3.84 (m, 3H), 6.85 (d, J=8.41 Hz, 1H), 6.98-7.07 (m, 2H) 7.09 (s, 1H) 7.15-7.22 (m, 1H) 7.29 (dd, J=8.41, 2.26 Hz, 1H) 7.35 (d, J=2.26 Hz, 1H). HRMS (TOF MS ES−) for C25H27O3S− (M−H)− calcd. 407.1681, found 407.1706.

Example 7: Methyl 2-{4-[(5,5,8,8-tetramethyl-5,6,7,8-tetrahydronaphthalen-2-yl)sulfanyl]phenyl}acetate (a) 6-iodo-1,1,4,4-tetramethyl-1,2,3,4-tetrahydronaphthalene

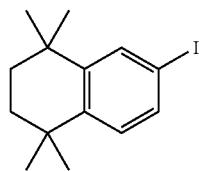

6-iodo-1,1,4,4-tetramethyl-1,2,3,4-tetrahydronaphthalene was prepared according to Christie, Victoria B. et al (Organic & Biomolecular Chemistry, 6(19), 3497-3507; 2008).

(b) methyl 2-{4-[(5,5,8,8-tetramethyl-5,6,7,8-tetrahydronaphthalen-2-yl)sulfanyl]phenyl}acetate

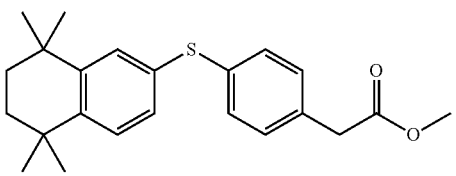 [SMILES: COC(=O)Cc1ccc(Sc2ccc3c(c2)C(C)(C)CCC3(C)C)cc1]

Methyl 2-{4-[(5,5,8,8-tetramethyl-5,6,7,8-tetrahydronaphthalen-2-yl)sulfanyl]phenyl}acetate was prepared according to example 1(c) starting from 305 mg of 6-iodo-1,1,4,4-tetramethyl-1,2,3,4-tetrahydronaphthalene. A colorless oil was obtained (225 mg, 60%) as a mixture of methyl 2-{4-[(5,5,8,8-tetramethyl-5,6,7,8-tetrahydronaphthalen-2-yl)sulfanyl]phenyl}acetate and butyl 2-{4-[(5,5,8,8-tetramethyl-5,6,7,8-tetrahydronaphthalen-2-yl)sulfanyl]phenyl}acetate (25%). $^1$H NMR (400 MHz, CHLOROFORM-d) δ ppm 1.26 (s, 6H), 1.24 (s, 6H), 1.67 (s, 4H), 3.59 (s, 2H), 3.69 (s, 3H), 7.09 (dd, J=8.28, 1.51 Hz, 1H), 7.16-7.21 (m, 2H), 7.22-7.25 (m, 3H), 7.35 (d, J=1.88 Hz, 1H).

Example 8: Butyl 2-{4-[(5,5,8,8-tetramethyl-5,6,7,8-tetrahydronaphthalen-2-yl)sulfanyl]phenyl}acetate

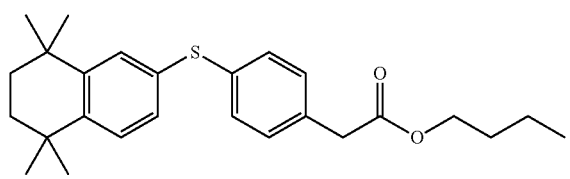 [SMILES: CCCCOC(=O)Cc1ccc(Sc2ccc3c(c2)C(C)(C)CCC3(C)C)cc1]

Butyl 2-{4-[(5,5,8,8-tetramethyl-5,6,7,8-tetrahydronaphthalen-2-yl)sulfanyl]phenyl}acetate was obtained in example 7(b). $^1$H NMR (400 MHz, CHLOROFORM-d) δ ppm 0.92 (t, J=7.09 Hz, 3H), 1.26 (s, 6H), 1.24 (s, 6H), 1.36-1.42 (m, 2H), 1.56-1.63 (m, 2H), 1.67 (s, 4H), 3.69 (s, 3H), 4.08 (t, J=6.71 Hz, 2H), 7.09 (dd, J=8.28, 1.51 Hz, 1H), 7.16-7.21 (m, 2H), 7.22-7.25 (m, 3H)), 7.35 (d, J=1.88 Hz, 1H).

Example 9: 2-{4-[(5,5,8,8-tetramethyl-5,6,7,8-tetrahydronaphthalen-2-yl)sulfanyl]phenyl}acetic Acid

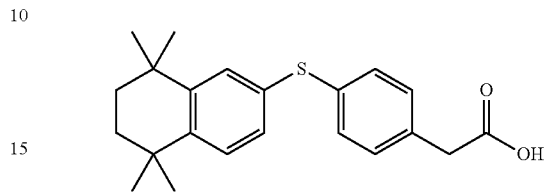

2-{4-[(5,5,8,8-tetramethyl-5,6,7,8-tetrahydronaphthalen-2-yl)sulfanyl]phenyl}acetic acid was prepared according to example 3 using 50 mg of (b) methyl 2-{4-[(5,5,8,8-tetramethyl-5,6,7,8-tetrahydronaphthalen-2-yl)sulfanyl]phenyl}acetate. A white solid was obtained (43 mg, 99%). mp=87° C. $^1$H NMR (400 MHz, CHLOROFORM-d) δ ppm 1.24 (s, 6H) 1.27 (s, 6H) 1.67 (s, 4H) 3.60 (s, 2H) 7.07-7.12 (m, 1H) 7.15-7.25 (m, 5H) 7.33-7.37 (m, 1H). HRMS (TOF MS ES−) for [(C22H26O2S)$_2$−1]− (M−H)− calcd. 707.3229, found 707.3204.

Example 10: Methyl 2-{3-[(5,5,8,8-tetramethyl-5,6,7,8-tetrahydronaphthalen-2-yl)sulfanyl]phenyl}acetate

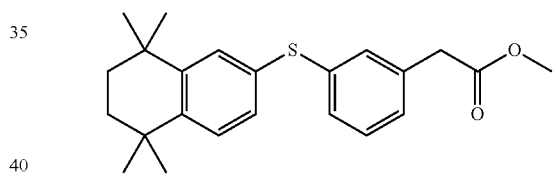

Methyl 2-{3-[(5,5,8,8-tetramethyl-5,6,7,8-tetrahydronaphthalen-2-yl)sulfanyl]phenyl}acetate was prepared according to example 1(c) starting from 305 mg of 6-iodo-1,1,4,4-tetramethyl-1,2,3,4-tetrahydronaphthalene. A colorless oil (210 mg, 55%) was obtained as a mixture of methyl 2-{3-[(5,5,8,8-tetramethyl-5,6,7,8-tetrahydronaphthalen-2-yl)sulfanyl]phenyl} and butyl 2-{3-[(5,5,8,8-tetramethyl-5,6,7,8-tetrahydronaphthalen-2-yl)sulfanyl]phenyl} (25%). $^1$H NMR (400 MHz, CHLOROFORM-d) δ ppm 1.27 (s, 6H), 1.24 (s, 6H), 1.68 (s, 4H), 3.57 (s, 2H), 3.67 (s, 3H), 7.07-7.14 (m, 2H), 7.14-7.18 (m, 1H), 7.23 (m, 3H), 7.34 (d, J=1.88 Hz, 1H).

Example 11: Butyl 2-{3-[(5,5,8,8-tetramethyl-5,6,7,8-tetrahydronaphthalen-2-yl)sulfanyl]phenyl}acetate

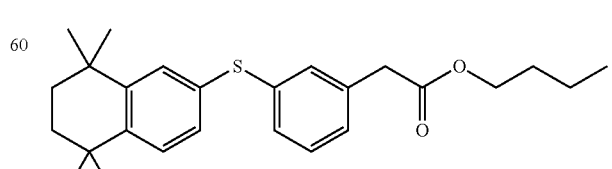

Butyl 2-{3-[(5,5,8,8-tetramethyl-5,6,7,8-tetrahydronaphthalen-2-yl)sulfanyl]phenyl}acetate was obtained in example 10. ¹H NMR (400 MHz, CHLOROFORM-d) δ ppm 0.94 (t, J=7.09 Hz, 3H), 1.27 (s, 6H), 1.24 (s, 6H), 1.32-1.41 (m, 2H), 1.52-1.59 (m, 2H), 1.68 (s, 4H), 3.57 (s, 2H), 4.07 (t, J=6.71 Hz, 2H), 7.07-7.14 (m, 2H), 7.14-7.18 (m, 1H), 7.23 (m, 3H), 7.34 (d, J=1.88 Hz, 1H).

Example 12: 2-{3-[(5,5,8,8-tetramethyl-5,6,7,8-tetrahydronaphthalen-2-yl)sulfanyl]phenyl}acetic Acid

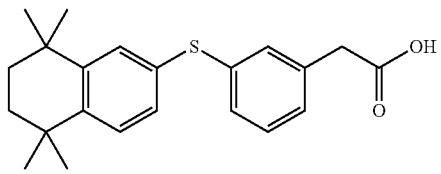 [SMILES: CC1(C)CCC(C)(C)c2cc(Sc3cccc(CC(=O)O)c3)ccc21]

2-{3-[(5,5,8,8-tetramethyl-5,6,7,8-tetrahydronaphthalen-2-yl)sulfanyl]phenyl}acetic acid was prepared according to example 3 using 50 mg of the mixture of methyl 2-{3-[(5,5,8,8-tetramethyl-5,6,7,8-tetrahydronaphthalen-2-yl)sulfanyl]phenyl}acetate and butyl 2-{3-[(5,5,8,8-tetramethyl-5,6,7,8-tetrahydronaphthalen-2-yl)sulfanyl]phenyl}acetate. A colorless oil was obtained (43 mg, 99%). ¹H NMR (400 MHz, CHLOROFORM-d) δ ppm 1.22 (s, 6H), 1.27 (s, 6H), 1.67 (s, 4H), 3.58 (s, 2H), 7.07-7.13 (m, 2H), 7.14-7.19 (m, 1H), 7.19-7.24 (m, 3H), 7.34 (d, J=1.88 Hz, 1H). HRMS (TOF MS ES−) for C22H25O2S⁻ (M−H)⁻ calcd. 353.1575, found 407.1591.

Example 13: Methyl 2-(4-{[3-(adamantan-1-yl)-4-methoxybenzene]sulfonyl}phenyl)-acetate

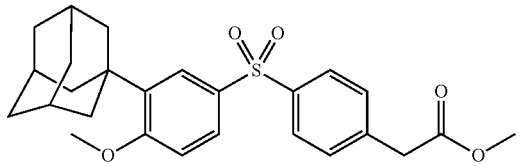 [SMILES: COC(=O)Cc1ccc(S(=O)(=O)c2ccc(OC)c(C34CC5CC(CC(C5)C3)C4)c2)cc1]

To a solution of mixture obtained in example 1(c) (110 mg, 0.26 mmol, 1 eq.) in THF (7 mL), was added a solution of oxone (475 mg, 0.775 mmol, 3 eq.) in water (4 mL). The reaction was stirred overnight at room temperature. Water (10 mL) was added and the mixture was extracted with dichloromethane (3×50 mL). After drying over Ca₂SO₄ and evaporation, the crude was purified by flash chromatography (cyclohexane/dichloromethane): (80/20) to (0/100). A white powder was obtained (80 mg, 70%) as a mixture of methyl 2-(4-{[3-(adamantan-1-yl)-4-methoxybenzene]sulfonyl}phenyl)acetate and butyl 2-(4-{[3-(adamantan-1-yl)-4-methoxybenzene]sulfonyl}phenyl)acetate (10%). ¹H NMR (400 MHz, CHLOROFORM-d) δ ppm 1.76 (s, 6H), 2.05 (s, 9H), 3.67 (s, 2H), 3.69 (s, 3H), 3.87 (s, 3H), 6.91 (d, J=9.16 Hz, 1H), 7.40 (d, J=8.16 Hz, 2H), 7.73-7.80 (m, 2H), 7.88 (d, J=8.28 Hz, 2H).

Example 14: Butyl 2-(4-{[3-(adamantan-1-yl)-4-methoxybenzene]sulfonyl}phenyl)acetate

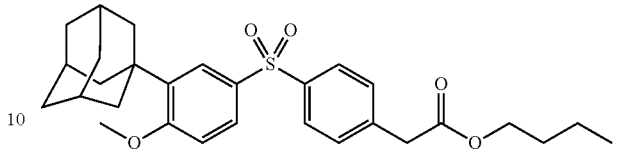

Butyl 2-(4-{[3-(adamantan-1-yl)-4-methoxybenzene]sulfonyl}phenyl)acetate was obtained from example 13. ¹H NMR (400 MHz, CHLOROFORM-d) δ ppm 0.89 (t, J=7.09 Hz, 3H), 1.28-1.37 (m, 2H), 1.51-1.60 (m, 2H), 1.76 (s, 6H), 2.05 (s, 9H), 3.67 (s, 2H), 3.87 (s, 3H), 4.09 (t, J=6.59 Hz, 2H), 6.91 (d, J=9.16 Hz, 1H), 7.40 (d, J=8.16 Hz, 2H), 7.73-7.80 (m, 2H), 7.88 (d, J=8.28 Hz, 2H).

Example 15: 2-(4-{[3-(adamantan-1-yl)-4-methoxybenzene]sulfonyl}phenyl)acetic Acid

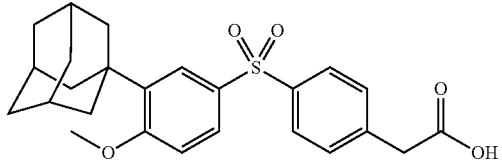 [SMILES: COc1ccc(S(=O)(=O)c2ccc(CC(=O)O)cc2)cc1C12CC3CC(CC(C3)C1)C2]

2-(4-{[3-(adamantan-1-yl)-4-methoxybenzene]sulfonyl}phenyl)acetic acid was prepared according to example 3 using 50 mg of methyl 2-(4-{[3-(adamantan-1-yl)-4-methoxybenzene]sulfonyl}phenyl)acetate. A white solid is obtained (35 mg, 73%). mp=212° C. ¹H NMR (400 MHz, CHLOROFORM-d) δ ppm 1.76 (s, 6H), 2.05 (m, 10H), 3.70 (s, 2H), 3.87 (s, 3H), 6.90 (d, J=9.29 Hz, 1H), 7.39 (m, J=8.28 Hz, 2H), 7.70-7.81 (m, 2H), 7.88 (m, J=8.28 Hz, 2H). HRMS (TOF MS ES−) for C22H25O2S⁻ (M−H)⁻ calcd. 353.1575, found 407.1591. HRMS (TOF MS ES−) for [(C25H28O5S)₂−1]⁻ (M−H)⁻ calcd. 879.3237, found 879.3265.

Example 16: Methyl 2-(3-{[3-(adamantan-1-yl)-4-methoxybenzene]sulfonyl}phenyl)-acetate

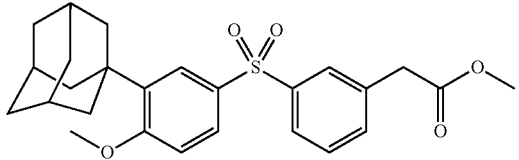 [SMILES: COC(=O)Cc1cccc(S(=O)(=O)c2ccc(OC)c(C34CC5CC(CC(C5)C3)C4)c2)c1]

Methyl 2-(3-{[3-(adamantan-1-yl)-4-methoxybenzene]sulfonyl}phenyl)acetate was prepared according to example 13 using 90 mg of mixture obtained in example 4(b). A thick oil was obtained (50 mg, 50%) as a mixture of methyl 2-(3-{[3-(adamantan-1-yl)-4-methoxybenzene]sulfonyl}phenyl)acetate and the butyl 2-(3-{[3-(adamantan-1-yl)-4-methoxybenzene]sulfonyl}phenyl)acetate (25%). ¹H NMR (400 MHz, CHLOROFORM-d) δ ppm 1.76 (s, 6H), 2.05 (s, 9H), 3.68 (s, 2H), 3.69 (s, 3H), 3.87 (s, 3H), 6.88-6.94 (m, 1H), 7.42-7.49 (m, 2H), 7.74-7.79 (m, 2H), 7.82 (dt, J=6.59, 2.04 Hz, 1H), 7.85 (br.s, 1H).

Example 17: Butyl 2-(3-{[3-(adamantan-1-yl)-4-methoxybenzene]sulfonyl}phenyl)acetate

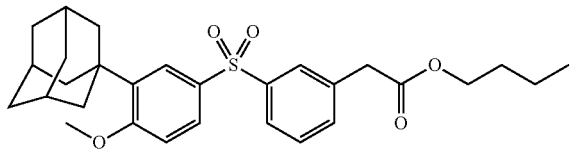 [SMILES: CCCCOC(=O)Cc1cccc(S(=O)(=O)c2ccc(OC)c(C34CC5CC(CC(C5)C3)C4)c2)c1]

Butyl 2-(3-{[3-(adamantan-1-yl)-4-methoxybenzene]sulfonyl}phenyl)acetate was obtained from example 16. $^1$H NMR (400 MHz, CHLOROFORM-d) δ ppm 0.90 (t, J=7.09 Hz, 3H), 1.26-1.38 (m, 2H), 1.55-1.62 (m, 2H), 1.76 (s, 6H), 2.05 (s, 9H), 3.68 (s, 2H), 3.87 (s, 3H), 4.09 (t, J=6.71 Hz, 2H), 6.88-6.94 (m, 1H), 7.42-7.49 (m, 2H), 7.74-7.79 (m, 2H), 7.82 (dt, J=6.59, 2.04 Hz, 1H), 7.85 (br.s, 1H).

Example 18: 2-(3-{[3-(adamantan-1-yl)-4-methoxybenzene]sulfonyl}phenyl)acetic Acid

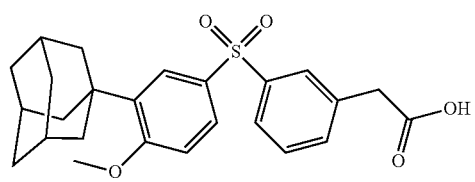 [SMILES: COc1ccc(S(=O)(=O)c2cccc(CC(=O)O)c2)cc1C12CC3CC(CC(C3)C1)C2]

2-(3-{[3-(adamantan-1-yl)-4-methoxybenzene]sulfonyl}phenyl)acetic acid was prepared according to example 3 using 50 mg of the mixture of methyl 2-(3-{[3-(adamantan-1-yl)-4-methoxybenzene]sulfonyl}phenyl)acetate and butyl 2-(3-{[3-(adamantan-1-yl)-4-methoxybenzene]sulfonyl}phenyl)acetate. A white solid is obtained (45 mg, 95%). mp=174° C. $^1$H NMR (400 MHz, CHLOROFORM-d) δ ppm 1.75 (s, 6H), 2.04 (s, 9H), 3.71 (s, 2H), 3.86 (s, 3H), 6.91 (d, J=9.29 Hz, 1H), 7.46 (m, 2H), 7.71-7.79 (m, 2H), 7.79-7.90 (m, 2H). HRMS (TOF MS ES−) for C25H27O5S− (M−H)− calcd. 439.1579, found 439.1600.

Example 19: Methyl 2-[4-(5,5,8,8-tetramethyl-5,6,7,8-tetrahydronaphthalene-2-sulfonyl)phenyl]acetate

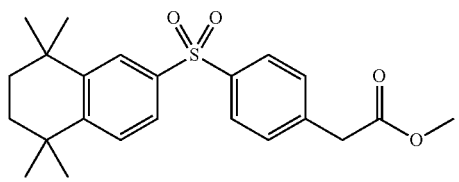 [SMILES: COC(=O)Cc1ccc(S(=O)(=O)c2ccc3c(c2)C(C)(C)CCC3(C)C)cc1]

Methyl 2-[4-(5,5,8,8-tetramethyl-5,6,7,8-tetrahydronaphthalene-2-sulfonyl)phenyl]acetate was prepared according to example 13 using 105 mg of the mixture obtained in example 7(b). An off-white solid was obtained (61 mg, 54%) as a mixture of methyl 2-[4-(5,5,8,8-tetramethyl-5,6,7,8-tetrahydronaphthalene-2-sulfonyl)phenyl]acetate and butyl 2-[4-(5,5,8,8-tetramethyl-5,6,7,8-tetrahydronaphthalene-2-sulfonyl)phenyl]acetate (5%). $^1$H NMR (400 MHz, CHLOROFORM-d) δ ppm 1.29 (s, 6H), 1.26 (s, 6H), 1.68 (s, 4H), 3.67 (s, 2H), 3.69 (s, 3H), 7.40 (m, 3H), 7.58 (dd, J=8.41, 2.01 Hz, 1H), 7.86-7.93 (m, 3H).

Example 20: Butyl 2-[4-(5,5,8,8-tetramethyl-5,6,7,8-tetrahydronaphthalene-2-sulfonyl)phenyl]acetate

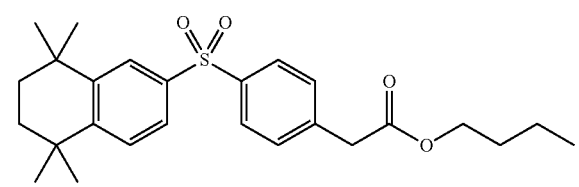 [SMILES: CCCCOC(=O)Cc1ccc(S(=O)(=O)c2ccc3c(c2)C(C)(C)CCC3(C)C)cc1]

Butyl 2-[4-(5,5,8,8-tetramethyl-5,6,7,8-tetrahydronaphthalene-2-sulfonyl)phenyl]acetate was obtained in example 19. $^1$H NMR (400 MHz, CHLOROFORM-d) δ ppm 0.88 (t, J=7.09 Hz, 3H), 1.29 (s, 6H), 1.26 (s, 6H), 1.37-1.43 (m, 2H), 1.56-1.63 (m, 2H), 1.68 (s, 4H), 3.67 (s, 2H), 4.09 (t, J=6.71 Hz, 2H), 7.40 (m, 3H), 7.58 (dd, J=8.41, 2.01 Hz, 1H), 7.86-7.93 (m, 3H).

Example 21: 2-[4-(5,5,8,8-tetramethyl-5,6,7,8-tetrahydronaphthalene-2-sulfonyl)phenyl]acetic Acid

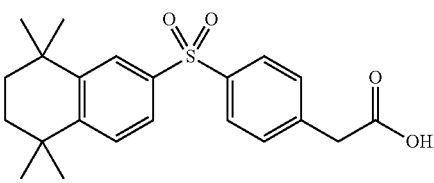 [SMILES: CC1(C)CCC(C)(C)c2cc(S(=O)(=O)c3ccc(CC(=O)O)cc3)ccc21]

2-[4-(5,5,8,8-tetramethyl-5,6,7,8-tetrahydronaphthalene-2-sulfonyl)phenyl]acetic acid was prepared according to example 3 using 45 mg of the mixture of methyl 2-[4-(5,5,8,8-tetramethyl-5,6,7,8-tetrahydronaphthalene-2-sulfonyl)phenyl]acetate and butyl 2-[4-(5,5,8,8-tetramethyl-5,6,7,8-tetrahydronaphthalene-2-sulfonyl)phenyl]acetate. A white solid is obtained (31 mg, 72%). mp=214° C. $^1$H NMR (400 MHz, CHLOROFORM-d) δ ppm 1.29 (s, 6H), 1.25 (s, 6H), 1.68 (s, 4H), 3.70 (s, 2H), 7.40 (m, 3H), 7.58 (dd, J=8.41, 2.01 Hz, 1H), 7.87-7.93 (m, 3H). HRMS (TOF MS ES−) for [(C22H26O4S)$_2$−1]− (M−H)− calcd. 771.3025, found 771.3063.

Example 22: Methyl 2-[3-(5,5,8,8-tetramethyl-5,6,7,8-tetrahydronaphthalene-2-sulfonyl)phenyl]acetate

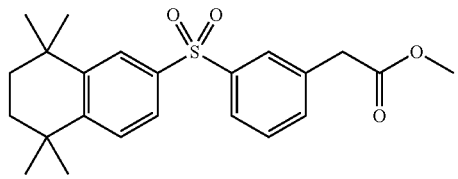 [SMILES: COC(=O)Cc1cccc(S(=O)(=O)c2ccc3c(c2)C(C)(C)CCC3(C)C)c1]

Methyl 2-[3-(5,5,8,8-tetramethyl-5,6,7,8-tetrahydronaphthalene-2-sulfonyl)phenyl]acetate was prepared according to example 13 using 90 mg of the mixture obtained in example 10. A thick oil was obtained (50 mg, 51%). $^1$H NMR (400 MHz, CHLOROFORM-d) δ ppm 1.29 (s, 6H) 1.26 (s, 6H) 1.68 (s, 4H) 3.69 (s, 5H) 7.40 (d, J=8.41 Hz, 1H) 7.43-7.52 (m, 2H) 7.59 (dd, J=8.41, 1.88 Hz, 1H) 7.83 (dt, J=7.00, 1.65 Hz, 1H) 7.88 (s, 1H) 7.90 (d, J=2.01 Hz, 1H).

Example 23: 2-[3-(5,5,8,8-tetramethyl-5,6,7,8-tetrahydronaphthalene-2-sulfonyl)phenyl]-acetic Acid

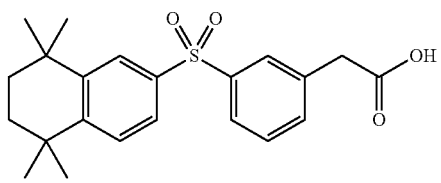 [SMILES: CC1(C)CCC(C)(C)c2cc(S(=O)(=O)c3cccc(CC(=O)O)c3)ccc21]

2-[3-(5,5,8,8-tetramethyl-5,6,7,8-tetrahydronaphthalene-2-sulfonyl)phenyl]acetic acid was prepared according to example 3 using 45 mg of methyl 2-[3-(5,5,8,8-tetramethyl-5,6,7,8-tetrahydronaphthalene-2-sulfonyl)phenyl]acetate. A white solid is obtained (41 mg, 95%). mp=75° C. $^1$H NMR (400 MHz, CHLOROFORM-d) δ ppm 1.25 (s, 6H), 1.27 (s, 6H), 1.67 (s, 4H), 3.72 (s, 2H), 7.39 (d, J=8.41 Hz, 1H), 7.43-7.52 (m, 2H), 7.56-7.63 (m, 1H), 7.84 (d, J=6.27 Hz, 1H), 7.89 (s, 2H). HRMS (TOF MS ES−) for C22H25O4S− (M−H)− calcd. 385.1474, found 385.1494.

Example 24: Ethyl 3-{4-[(5,5,8,8-tetramethyl-5,6,7,8-tetrahydronaphthalen-2-yl)sulfanyl]phenyl}propanoate 5,5,8,8-Tetramethyl-5,6,7,8-tetrahydro-naphthalene-2-disulfide

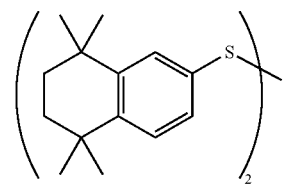

5,5,8,8-Tetramethyl-5,6,7,8-tetrahydro-naphthalene-2-disulfide was prepared according to a procedure described by Boiteau et al. (WO2014016507A1). mp=83-85° C. $^1$H NMR (400 MHz, CHLOROFORM-d) δ ppm 1.24 (s, 6H), 1.21 (s, 6H,) 1.65 (s, 4H), 7.23 (d, J=8.28 Hz, 1H), 7.28 (dd, J=8.28, 1.88 Hz, 1H), 7.41 (d, J=1.88 Hz, 1H).

Scheme 2

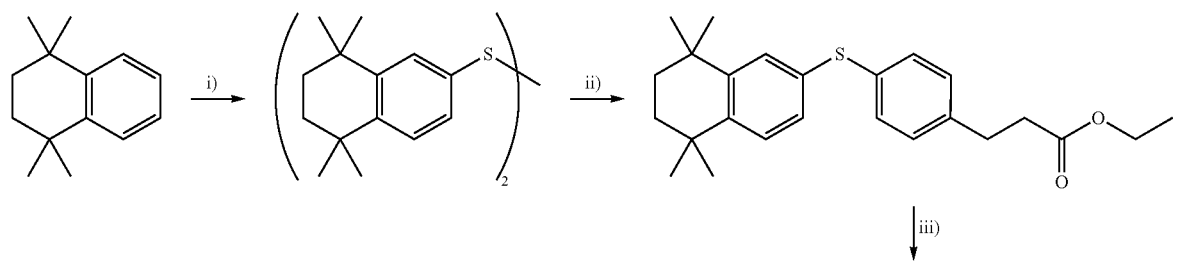

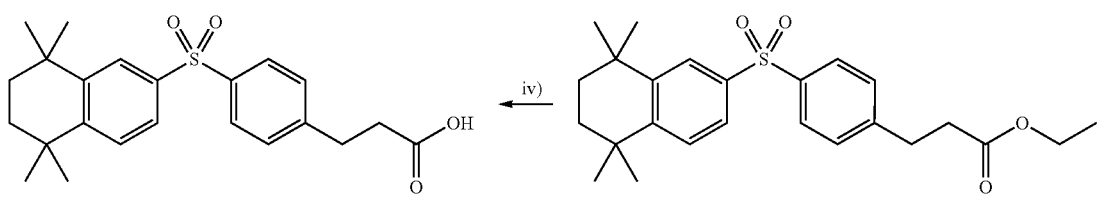

i) 1) Chlorosulfonic acid, 0° C. to r.t., 3 h, 2) Zn, EtOH, conc. HCl, reflux 45 min, r.t. overnight;
ii) ethyl 3-(4-bromophenyl)propanoate, PdCl$_2$(dppf), Zn, THF, relux, 24 h;
iii) oxone, H$_2$O, MeOH, 0° C. to r.t., 12 h; iv) LiOH 1N, THF, H$_2$O, r.t. 12 h.

(a) Ethyl 3-{4-[(5,5,8,8-tetramethyl-5,6,7,8-tetrahydronaphthalen-2-yl)sulfanyl]phenyl}propanoate

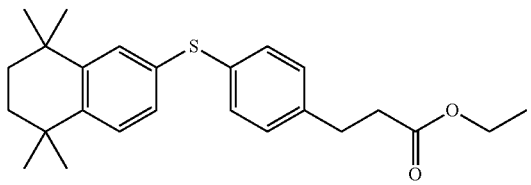 [SMILES: CCOC(=O)CCc1ccc(Sc2ccc3c(c2)C(C)(C)CCC3(C)C)cc1]

Ethyl 3-{4-[(5,5,8,8-tetramethyl-5,6,7,8-tetrahydronaphthalen-2-yl)sulfanyl]phenyl}propanoate was prepared according to the method described by Fukuzawa et al. (Synlett 2006, 13, 2145-47). 5,5,8,8-Tetramethyl-5,6,7,8-tetrahydro-naphthalene-2-disulfide (100 mg, 0.228 mmol, 0.5 eq.), PdCl$_2$(dppf) (17 mg, 0.023 mmol, 0.05 eq.), and zinc (36 mg, 0.547 mmol, 1.2 eq.) were placed in a flask and then a solution of ethyl 3-(4-bromophenyl)propanoate (115 mg, 0.456 mmol, 1 eq.) in THF (3 mL) was added. The mixture was refluxed for 24 h and diluted with Et$_2$O (30 mL) after cooling. The precipitate was removed by filtration and the filtrate was washed with brine and dried over Ca$_2$SO$_4$. After concentration of the organic layer, the crude was concentrated and grossly purified by chromatography over silica gel (cyclohexane/dichloromethane): (95/5) to (55/45). A mixture of the title compound and ethyl 3-(4-bromophenyl)propanoate (30%) was obtained (125 mg). It was used in the next step without any further purification.

Example 25: Ethyl 3-[4-(5,5,8,8-tetramethyl-5,6,7,8-tetrahydronaphthalene-2-sulfonyl)phenyl]propanoate Ethyl 3-[4-(5,5,8,8-tetramethyl-5,6,7,8-tetrahydronaphthalene-2-sulfonyl)phenyl]propanoate was prepared according to example 13 using 125 mg of mixture obtained in example 24 (b). A white solid was obtained (82 mg, 87%). mp=105-106° C. $^1$H NMR (400 MHz, CHLOROFORM-d) δ ppm 1.19 (t, J=7.11 Hz, 3H), 1.28 (s, 6H), 1.25 (s, 6H), 1.68 (s, 4H), 2.62 (t, J=7.53 Hz, 2H), 2.99 (t, J=7.53 Hz, 2H), 4.10 (q, J=7.11 Hz, 2H), 7.33 (m, J=8.16 Hz, 2H), 7.39 (d, J=8.41 Hz, 1H), 7.58 (dd, J=8.41, 1.51 Hz, 1H), 7.85 (m, J=8.16 Hz, 2H), 7.88-7.92 (m, 1H).

Example 26: 3-[4-(5,5,8,8-tetramethyl-5,6,7,8-tetrahydronaphthalene-2-sulfonyl)phenyl]propanoic Acid

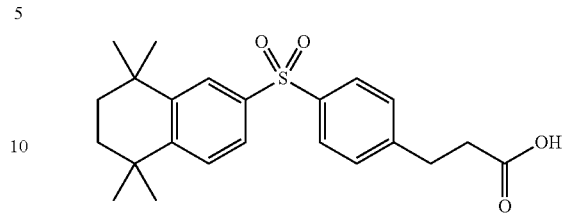

3-[4-(5,5,8,8-tetramethyl-5,6,7,8-tetrahydronaphthalene-2-sulfonyl)phenyl]propanoic acid was prepared according to example 3 starting from 66 mg of ethyl 3-[4-(5,5,8,8-tetramethyl-5,6,7,8-tetrahydronaphthalene-2-sulfonyl)phenyl]propanoate. A white solid is obtained (53 mg, 85%). mp=211° C. $^1$H NMR (400 MHz, METHANOL-d$_4$) δ ppm 1.30 (s, 6H), 1.32 (s, 6H), 1.75 (s, 4H), 2.65 (t, H=7.59 Hz, 2H), 3.01 (t, J=7.59 Hz, 2H), 7.48 (m, J=8.41 Hz, 2H), 7.56 (d, J=8.41 Hz, 1H), 7.65 (dd, J=8.41, 2.01 Hz, 1H), 7.87 (m, J=8.41 Hz, 2H), 7.90 (d, J=2.01 Hz, 1H). HRMS (TOF MS ES−) for C23H27O4S− (M−H)− calcd. 399.1630, found 399.1658.

Scheme 3

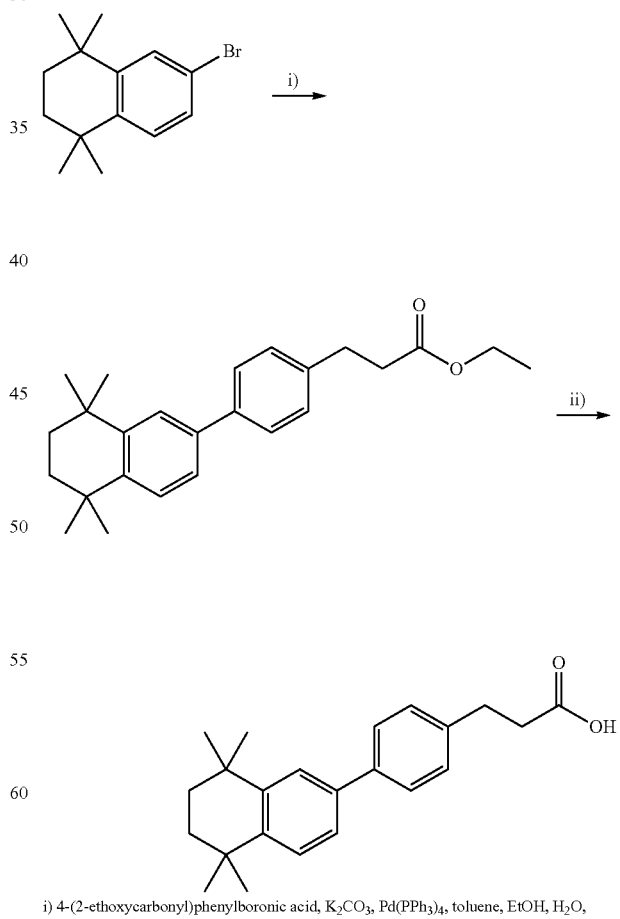

i) 4-(2-ethoxycarbonyl)phenylboronic acid, K$_2$CO$_3$, Pd(PPh$_3$)$_4$, toluene, EtOH, H$_2$O, reflux, 3 h 30; ii) LiOH 1N, THF, H$_2$O r.t. 12 h.

Example 27: Ethyl 3-[4-(5,5,8,8-tetramethyl-5,6,7,8-tetrahydronaphthalen-2-yl)phenyl]propanoate

Example 28: 3-[4-(5,5,8,8-tetramethyl-5,6,7,8-tetrahydronaphthalen-2-yl)phenyl]propanoic Acid

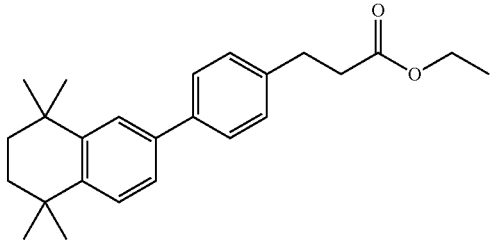 [SMILES: CCOC(=O)CCc1ccc(-c2ccc3c(c2)C(C)(C)CCC3(C)C)cc1]

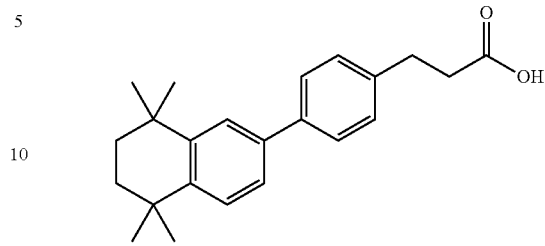

3-[4-(5,5,8,8-tetramethyl-5,6,7,8-tetrahydronaphthalen-2-yl)phenyl]propanoic acid was prepared according to example 3 starting from 60 mg of ethyl 3-[4-(5,5,8,8-tetramethyl-5,6,7,8-tetrahydronaphthalen-2-yl)phenyl]propanoate. A white solid is obtained (50 mg, 88%). mp=196° C. $^1$H NMR (400 MHz, CHLOROFORM-d) δ ppm 1.32 (s, 6H), 1.33 (s, 6H) 1.65-1.77 (m, 4H), 2.73 (t, J=6.90 Hz, 2H), 3.01 (t, J=6.90 Hz, 2H), 7.26-7.30 (m, 2H), 7.30-7.40 (m, 2H), 7.46-7.54 (m, 3H). HRMS (TOF MS ES−) for C23H27O2− (M−H)− calcd. 335.2011 found 335.2010.

Ethyl 3-[4-(5,5,8,8-tetramethyl-5,6,7,8-tetrahydronaphthalen-2-yl)phenyl]propanoate was prepared according to the procedure described by Suzuki and co. (Synth. Com. 1981, 513-19). To a solution of 6-bromo-1,1,4,4-tetramethyl-1,2,3,4-tetrahydronaphthalene (110 mg, 0.41 mmol, 1 eq.) in degassed toluene (1 mL), a solution of 4-(2-ethoxycarbonyl)phenylboronic acid (100 mg, 0.45 mmol, 1.1 eq,) in degassed ethanol (0.2 mL) and a solution of K$_2$CO$_3$ (113 mg, 0.82 mmol, 2 eq.) in degassed water (0.4 mL) were successively added. Then Pd(PPh$_3$)$_4$ (14 mg, 0.0123 mmol, 0.03 eq.) was added and the resulting mixture was heated to reflux for 3 h 30. Water was added and the mixture was extracted with dichloromethane. The resulting organic layers were dried over brine and Ca$_2$SO$_4$ and then concentrated. The crude was purified by flash chromatography, (cyclohexane/dichloromethane): (65/35) to (35/65) to afford a thick yellow oil (80 mg, 60%), $^1$H NMR (400 MHz, CHLOROFORM-d) δ ppm 1.24 (t, J=7.15 Hz, 2H), 1.31 (s, 6H), 1.33 (s, 6H) 1.71 (s, 4H), 2.65 (t, J=7.72 Hz, 2H), 2.98 (t, J=7.72 Hz, 2H), 4.14 (q, J=7.15 Hz, 2H), 7.25 (d, J=7.15 Hz, 2H), 7.30-7.39 (m, 2H), 7.45-7.53 (m, 3H).

Scheme 4

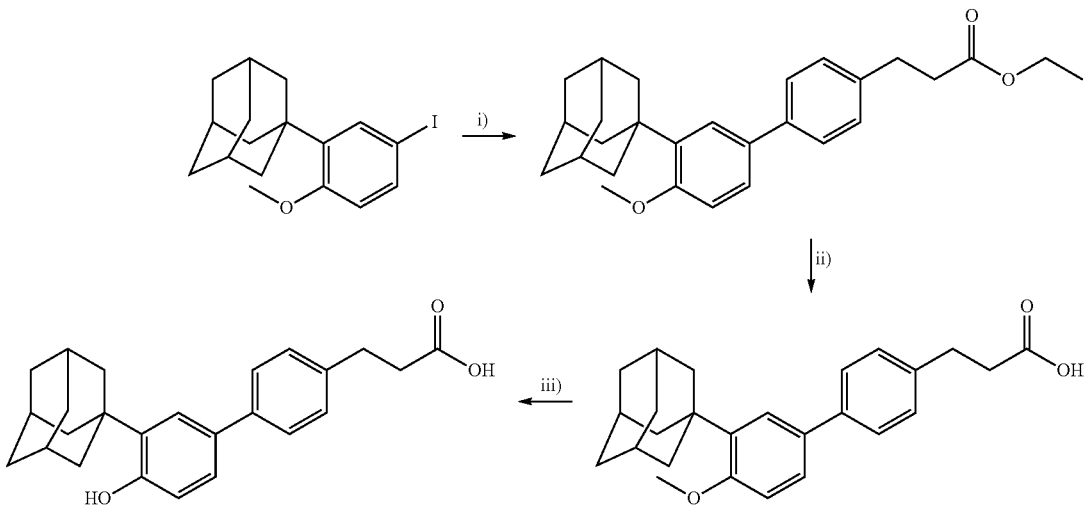

i) 4-(2-ethoxycarbonyl)phenylboronic acid, K$_2$CO$_3$, Pd(PPh$_3$)$_4$, toluene, EtOH, H$_2$O, reflux, overnight;
ii) LiOH 1N, THF, H$_2$O, r.t. 12 h. iv) BBr$_3$, DCM, -78° C., 30 minutes, 0° C., 2 h.

Example 29: Ethyl 3-{4-[3-(adamantan-1-yl)-4-methoxyphenyl]phenyl}propanoate

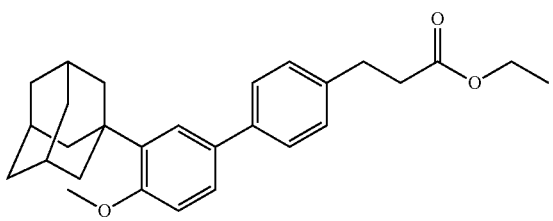 [SMILES: CCOC(=O)CCc1ccc(-c2ccc(OC)c(C34CC5CC(CC(C5)C3)C4)c2)cc1]

Ethyl 3-{4-[3-(adamantan-1-yl)-4-methoxyphenyl]phenyl}propanoate was prepared according to example 27 starting from 600 mg of 2-adamantyl-4-iodoanisole. A white solid was obtained (275 mg, 40%), mp=124° C. ¹H NMR (400 MHz, CHLOROFORM-d) δ ppm 1.25 (t, J=7.03 Hz, 3H), 1.78 (s, 6H), 2.08 (s, 3H), 2.14 (s, 6H), 2.65 (t, J=7.78 Hz, 2H), 2.98 (t, J=7.78 Hz, 2H), 3.86 (s, 3H), 4.14 (q, J=7.03 Hz, 2H), 6.93 (d, J=8.30 Hz, 1H), 7.20-7.28 (m, 2H), 7.38 (d, J=8.30 Hz, 1H), 7.43 (s, 1H), 7.48 (d, J=7.78 Hz, 2H).

Example 30: 3-{4-[3-(adamantan-1-yl)-4-methoxyphenyl]phenyl}propanoic Acid

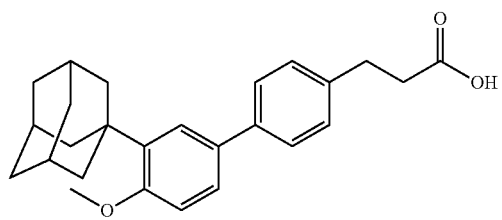 [SMILES: COc1ccc(-c2ccc(CCC(=O)O)cc2)cc1C12CC3CC(CC(C3)C1)C2]

3-{4-[3-(adamantan-1-yl)-4-methoxyphenyl] phenyl}propanoic acid was prepared according to example 3 starting from 275 mg of ethyl 3-{4-[3-(adamantan-1-yl)-4-methoxyphenyl]phenyl}propanoate. A white solid is obtained (200 mg, 75%). mp=252-253° C. ¹H NMR (400 MHz, CHLOROFORM-d) δ ppm 1.78 (s, 6H), 2.08 (s, 3H), 2.14 (s, 6H), 2.72 (t, J=7.76 Hz, 2H), 3.00 (t, J=7.76 Hz, 2H), 3.87 (s, 3H), 6.93 (d, J=8.41 Hz, 1H), 7.24 (s, 2H), 7.38 (dd, J=8.28, 2.13 Hz, 1H), 7.43 (d, J=2.13 Hz, 1H), 7.49 (d, J=8.41 Hz, 2H). HRMS (TOF MS ES+) for $C_{26}H_{31}O_3^+$ (MH+) calcd. 391.2273, found 391.2291.

Example 31: 3-{4-[3-(adamantan-1-yl)-4-hydroxyphenyl]phenyl}propanoic Acid

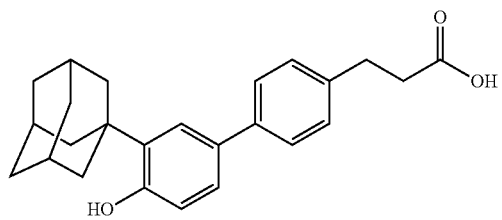 [SMILES: O=C(O)CCc1ccc(-c2ccc(O)c(C34CC5CC(CC(C5)C3)C4)c2)cc1]

3-{4-[3-(adamantan-1-yl)-4-methoxyphenyl] phenyl}propanoic acid (270 mg, 0.7 mmol, 1 eq.) was suspended in dichloromethane (10 mL) and a 1M solution of BBr₃ in dichloromethane (2.8 mL) was slowly added at −78° C. The mixture was stirred at −78° C. for 30 minutes and then slowly warmed up to 0° C. and kept at this temperature for 2 hours. Water was added (10 mL) at 0° C. and the mixture was extracted with dichloromethane (3×50 mL). The resulting organic layers were dried over brine and Ca₂SO₄ and then concentrated to afford a brown solid without any further purification. mp=212-215° C. ¹H NMR (400 MHz, METHANOL-d₄) δ ppm 1.85 (br. s., 6H) 2.09 (br. s., 3H) 2.24 (br. s., 6H) 2.65 (br. s., 2H) 2.95 (br. s., 2H) 6.79 (d, J=7.78 Hz, 1H) 7.15-7.31 (m, 3H) 7.37 (br. s., 1H) 7.41-7.55 (m, 2H). HRMS (TOF MS ES+) for $C_{25}H_{29}O_3^+$ (MH+) calcd. 377.2117, found 377.2107.

Example 32: Benzyl (2E)-3-{4-[3-(adamantan-1-yl)-4-methoxyphenyl]phenyl}prop-2-enoate (a) (E)-Benzyl 3-(4-bromophenyl)acrylate To a stirred solution of the bromobenzaldehyde (1.0 g, 5.4 mmol) in CH₂Cl₂ (20 mL) was added benzyl-2-(triphenylphosphoranylidene)acetate slowly and stirred for 10 minutes at rt. Then refluxed for 2 hours at 50° C. and allowed to cool to r.t. The solution was concentrated under reduced pressure and purified on Biotage to yield a white solid, 1.32 g (77%), mp=97-99° C.; ¹H NMR (400 MHz, CDCl₃) δ 7.65 (d, J=16.0 Hz, 1H), 7.51 (d, J=8.5 Hz, 2H), 7.44-7.32 (m, 7H), 6.47 (d, J=16.0 Hz, 1H), 5.25 (s, 2H).

(b) [3-(adamantan-1-yl)-4-methoxyphenyl]boronic Acid

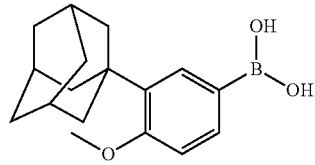 [SMILES: COc1ccc(B(O)O)cc1C12CC3CC(CC(C3)C1)C2]

To a solution of 1-(5-iodo-2-methoxyphenyl)adamantane or 1-(5-bromo-2-methoxyphenyl)adamantane (2.0 g, 6.22 mmol) in dried THF (15 mL) at −78° C. was slowly added nBuLi of 2.5 M solution in hexane (3.0 mL) over 10 minutes. The solution was stirred for 1 hr and B(Oi-Pr)₃ (5.75 mL, 25 mmol) was added by a syringe at −78° C. The solution was stirred for 1 hr at −78° C. and then allowed to warm to rt overnight. The reaction was cooled to 0° C. followed by the sequential addition of water (1.5 mL) and 2 N HCl (1.5 mL). After 5 minutes, an additional 27 mL (2N HCl) was added and stirred for 10 minutes. The mixture was extracted with 3×20 mL EtOAc and the combined organic layers were concentrated to a thick oil. Crystallization with heptanes yielded the title compound as a yellow powder, 1.533 g (86%); M. p. 261-263° C.; R$_f$=0.55 (60% EtOAc: heptanes). ¹H NMR (500 MHz, cdcl₃) δ 8.15 (d, J=1.5 Hz, 1H), 8.05 (dd, J=8.1, 1.5 Hz, 1H), 7.00 (d, J=8.2 Hz, 1H), 3.91 (s, 3H), 2.26-2.06 (m, 9H), 1.82 (s, 6H).

(c) benzyl (2E)-3-{4-[3-(adamantan-1-yl)-4-methoxyphenyl]phenyl}prop-2-enoate

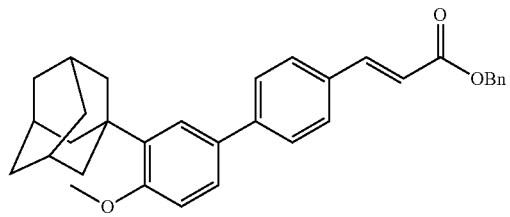 [SMILES: COc1ccc(-c2ccc(/C=C/C(=O)OCc3ccccc3)cc2)cc1C12CC3CC(CC(C3)C1)C2]

In a 50 mL three-necked flask, equipped with a stirrer, a reflux condenser and a gas inlet adapter was introduced 6.41 mg (0.5 mol %) of tris(dibenzylydeneacetone)dipalladium (0) Pd₂(dba)₃ and dissolved in 5 mL of tetrahydrofuran. Then 5.75 mg (1 mol %) of Sphos was added and the solution stirred for 30 min under a slight stream of argon. To the reaction mixture 400 mg (1.4 mmol) 3-(1-adamantyl)-4-methoxyphenylboronic acid and 444 mg (1.4 mmol) of (E)-Benzyl 3-(4-bromophenyl)acrylate were added and stirred until all components were dissolved. A solution of 2 mL of 0.28 M of sodium carbonate was then added. The mixture was vigorously stirred for 4 h with boiling at 80° C. under a slight stream of argon. The two layers were separated and organic layer dried under MgSO$_4$, filtered and concentrated under reduced pressure. Then it was purified on a HP-Sil 25 g Biotage SNAP cartridge and eluted with EtOAc:heptane using a gradient (0-10%) at a flow rate of 20 mL/min to provide a white solid (498 mg, 74%). mp=152-154° C.; $^1$H NMR (400 MHz, CDCl$_3$) δ 7.76 (d, J=16.0 Hz, 1H), 7.62-7.53 (m, 4H), 7.48 (d, J=2.2 Hz, 1H), 7.46-7.31 (m, 6H), 6.95 (d, J=8.5 Hz, 1H), 6.50 (d, J=16.0 Hz, 1H), 5.26 (s, 2H), 3.88 (s, 3H), 2.14 (s, 6H), 2.08 (s, 3H), 1.78 (s, 6H).

Example 33: 2(E)-3-{4-[3-(adamantan-1-yl)-4-methoxyphenyl]phenyl}prop-2-enoic Acid

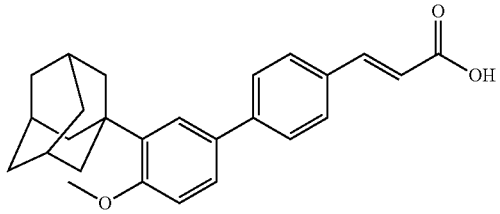 [SMILES: COc1ccc(-c2ccc(/C=C/C(=O)O)cc2)cc1C12CC3CC(CC(C3)C1)C2]

A suspension of the ester benzyl (2E)-3-{4-[3-(adamantan-1-yl)-4-methoxyphenyl]phenyl}prop-2-enoate (100 mg, 0.21 mmol) in 1.0 mL of MeOH:H$_2$O (9:1) was treated with 25 mg (0.45 mmol) of KOH and 0.1 mL THF. The reaction mixture was stirred for 5-6 h at 70-75° C., cooled to room temperature and quenched with water (5.0 mL). The mixture was extracted with Et$_2$O (10 mL) and the aqueous layer was acidified to pH 2 with 1N HCl and extracted with ethyl acetate (3×15 mL). The combined organic phases were dried and evaporated. The residue was crystallized from ethyl acetate-hexane to give 80 mg (99%) of the acid as white crystals. mp=327-328° C.; $^1$H NMR (400 MHz, DMSO) δ 12.38 (s, 1H), 7.73 (d, J=8.3 Hz, 2H), 7.65 (d, J=8.4 Hz, 2H), 7.61 (d, J=16.2 Hz, 1H), 7.53 (dd, J=8.5, 2.1 Hz, 1H), 7.43 (d, J=2.2 Hz, 1H), 7.07 (d, J=8.6 Hz, 1H), 6.54 (d, J=16.0 Hz, 1H), 3.84 (s, 3H), 2.10 (s, 6H), 2.05 (s, 3H), 1.74 (s, 6H) HRMS (TOF MS ES+) for C$_{26}$H$_{29}$O$_3$$^1$ (MH+) calcd. 389.2134, found 389.2117.

Example 34: (2E)-3-{4-[3-(adamantan-1-yl)-4-hydroxyphenyl]phenyl}prop-2-enoic Acid

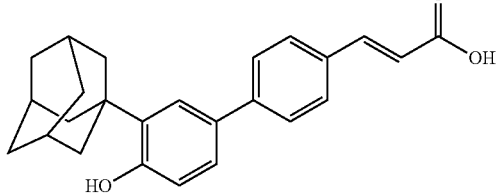

Title compound was prepared according to example 31 starting from 70 mg of 2(E)-3-{4-[3-(adamantan-1-yl)-4-methoxyphenyl]phenyl}prop-2-enoic acid. The residue was purified on a HP-Sil 25 g Biotage SNAP cartridge and eluted with EtOAc:heptane using a gradient (0-25%) at a flow rate of 20 mL/min to provide a yellow solid (41 mg, 61%). mp=273-275° C.; $^1$H NMR (400 MHz, DMSO) δ 9.62 (s, 1H), 7.68 (d, J=8.1 Hz, 2H), 7.60 (d, J=8.2 Hz, 2H), 7.56 (d, J=16.0 Hz, 1H), 7.36 (d, J=7.9 Hz, 2H), 6.87 (d, J=7.9 Hz, 1H), 6.53 (d, J=15.9 Hz, 1H), 2.13 (s, 6H), 2.05 (s, 3H), 1.74 (s, 6H). HRMS (TOF MS ES+) for C$_{25}$H$_{27}$O$_3$$^+$ (MH+) calcd. 375.1960, found 375.1921.

Example 35: Benzyl (2E)-3-(4-{[3-(adamantan-1-yl)-4-methoxyphenyl]amino}phenyl)-prop-2-enoate (a) tert-butyl N-[4-(hydroxymethyl)phenyl]carbamate

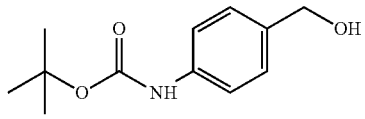 [SMILES: CC(C)(C)OC(=O)Nc1ccc(CO)cc1]

A 100-mL, three-necked, round-bottomed flask, was equipped with a magnetic stirring bar, a reflux condenser, and a pressure-equalizing dropping funnel that was connected to a nitrogen flow line and charged with a solution of 97% di-tert-butyl dicarbonate (4.04 g, 18.5 mmol) in tetrahydrofuran (30 mL). Amino benzyl alcohol (2.5 g, 20.3 mmol) was placed in the flask and suspended in tetrahydrofuran (65 mL) and 99% triethylamine (3.1 mL, 22 mmol). The resulting white suspension was cooled with an ice-water bath and the solution of di-tert-butyl dicarbonate was added dropwise over a period of 30 minutes. After 10 min of additional stirring, the ice-water bath was removed and the suspension was stirred overnight at room temperature, then warmed at 50° C. for a further 3 hours. The solvent was removed under reduced pressure and the residue partitioned between EtOAc (50 mL) and saturated aqueous bicarbonate solution (50 mL). The aqueous phase was extracted with three 50-mL portions of EtOAc. The combined organic phases were dried with anhydrous MgSO$_4$ and concentrated under reduced pressure to give 3.72 g (83% yield) of the product as a brown oil that was used without further purification. $^1$H NMR (as rotamers) (400 MHz, CDCl$_3$) δ 9.26 (s, 1H), 8.64 (s, 1H), 7.39 (4H), 7.20 (4H), 5.75 (s, 1H), 5.05 (2H), 4.49-4.35 (m, 4H), 1.47 (s, 9H), 1.40 (s, 1H).

(b) tert-butyl N-(4-formylphenyl)carbamate

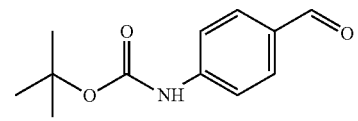 [SMILES: CC(C)(C)OC(=O)Nc1ccc(C=O)cc1]

To a stirring solution of suspended pyridinium chlorochromate (3.84 g, 17.81 mmol) in 100 ml of anhydrous CH$_2$Cl$_2$ was added tort-butyl N-[4-(hydroxymethyl)phenyl]carbamate (2.65 g, 11.87 mmol) in 10 mL CHCl$_2$ in one portion. After 1.5 hrs, TLC showed full consumption of the starting material. Then filtered with a pad of celite and the resulting dark brown solution was rotary evaporated under reduced pressure. The residue was purified on a Biotage SNAP cartridge (100 g) using an EtOAc:cyclohexane gradient (0-20%) to yield a yellowish-white solid. Recrystallized from EtOAc/cyclohexane, 2.26 g (86%). M. p. 140-142° C.; $^1$H NMR (400 MHz, CDCl$_3$) δ 9.89 (s, 1H), 7.82 (d, J=8.6 Hz, 2H), 7.56 (d, J=8.6 Hz, 2H), 6.99 (s, 1H), 1.53 (s, 9H).

(c) benzyl (2E)-3-(4-{[(tert-butoxy)carbonyl]amino}phenyl)prop-2-enoate

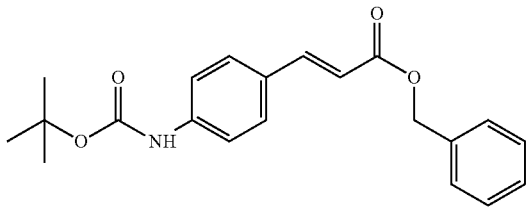 [SMILES: CC(C)(C)OC(=O)Nc1ccc(/C=C/C(=O)OCc2ccccc2)cc1]

To a stirred solution of aldehyde tert-butyl N-(4-formylphenyl)carbamate (1.16 g, 5.24 mmol) in CH$_2$Cl$_2$ (20 mL) was added benzyl-2-(triphenylphosphoranylidene)acetate slowly and stirred for 10 minutes at r.t. Then refluxed for 2 hours at 50° C. and allowed to cool to rt. The solution was concentrated under reduced pressure and purified on Biotage to yield a white solid, 1.80 g (99%). M. p. 93-95° C. $^1$H NMR (400 MHz, CDCl$_3$) δ 7.67 (d, J=16.0 Hz, 1H), 7.49-7.30 (9H), 6.65 (s, 1H), 6.39 (d, J=16.0 Hz, 1H), 5.24 (s, 2H), 1.52 (s, 9H).

(d) benzyl (2E)-3-(4-aminophenyl)prop-2-enoate

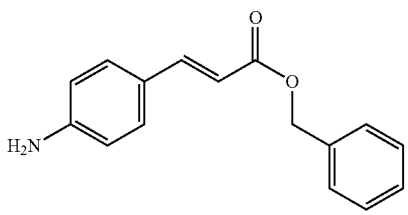 [SMILES: Nc1ccc(/C=C/C(=O)OCc2ccccc2)cc1]

To a stirring solution of benzyl (2E)-3-(4-{[(tert-butoxy)carbonyl]amino}phenyl)prop-2-enoate in CH$_2$Cl$_2$ at 0° C. were added TFA and allowed to warm to r.t. over 2 hours. TLC showed the reaction was complete. It was then quenched by addition of 30 mL saturated NaHCO$_3$ solution and extracted 3×30 mL CH$_2$Cl$_2$. The combined organic phases was dried over MgSO$_4$ and concentrated under reduced pressure. The residue was purified on Biotage on a 50 g Biotage SNAP cartridge using 30% EtOAc:cyclohexane gradient to yield a yellow solid, 1.043 g (85%). M. p. 112-114° C. $^1$H NMR (400 MHz, CDCl$_3$) δ 7.64 (d, J=15.9 Hz, 1H), 7.43-7.29 (7H), 6.63 (d, J=8.5 Hz, 2H), 6.28 (d, J=15.9 Hz, 1H), 5.23 (s, 2H), 3.93 (s, 2H).

(e) benzyl (2E)-3-(4-{[3-(adamantan-1-yl)-4-methoxyphenyl]amino}phenyl)prop-2-enoate

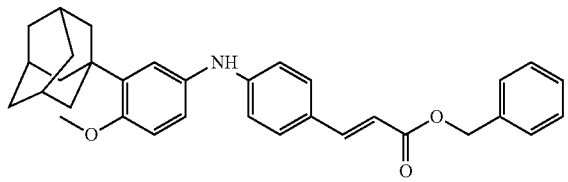 [SMILES: COc1ccc(Nc2ccc(/C=C/C(=O)OCc3ccccc3)cc2)cc1C12CC3CC(CC(C3)C1)C2]

To a 20 mL scintillation vial equipped with a magnetic stir bar was added the 3-(1-adamantyl)-4-methoxyphenylboronic acid (600 mg, 2.1 mmol), benzyl (2E)-3-(4-aminophenyl)prop-2-enoate (531 mg, 2.1 mmol), anhydrous cupric acetate (384 mg, 2.1 mmol), 750 mg of activated 4 Å molecular sieves, pyridine (3.3 mL of 0.67M in CH$_2$Cl$_2$), and 15 mL CH$_2$Cl$_2$. The reaction was stirred at room temperature in the loosely capped vial for 2 days. The reaction was complete as shown by TLC analysis of an aliquot. The reaction was filtered through Celite, washed with methanol and purified on a Biotage SNAP cartridge and eluted with EtOAc:cyclohexane using a gradient (0-15%) to provide a brown solid (661 mg, 64%). M. p. 133-135° C.; Rf=0.38 (15% EtOAc:cyclohexane). 1H NMR (400 MHz, CDCl3) δ 7.65 (d, J=15.9 Hz, 1H), 7.46-7.29 (7H), 7.00 (dd, J=12.8, 2.5 Hz, 2H), 6.85-6.78 (m, 3H), 6.29 (d, J=15.9 Hz, 1H), 5.77 (s, 1H), 5.23 (s, 2H), 3.83 (s, 3H), 2.06 (s, 9H), 1.76 (s, 6H). 13C NMR (101 MHz, CDCl3) δ 167.51, 155.54, 147.90, 145.33, 139.84, 136.40, 133.42, 129.92, 128.52, 128.17, 128.08, 126.75, 126.42, 124.82, 121.72, 120.45, 120.40, 114.27, 113.09, 112.43, 111.67, 66.00, 55.33, 40.52, 37.13, 37.06, 37.03, 29.10, 29.02. HRMS (TOF MS ES+) for C33H36NO3+ (MH+) calcd. 494.2695, found 494.2682.

Example 36: (2E)-3-(4-{[3-(adamantan-1-yl)-4-methoxyphenyl]amino}phenyl)prop-2-enoic Acid

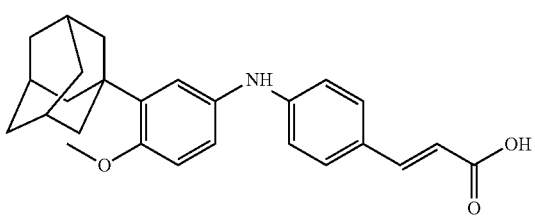 [SMILES: COc1ccc(Nc2ccc(/C=C/C(=O)O)cc2)cc1C12CC3CC(CC(C3)C1)C2]

(2E)-3-(4-{[3-(adamantan-1-yl)-4-methoxyphenyl]amino}phenyl)prop-2-enoic acid was prepared according to example 33 staring from 130 mg of benzyl (2E)-3-(4-{[3-(adamantan-1-yl)-4-methoxyphenyl]amino}phenyl)prop-2-enoate. The residue was purified on Biotage to give 69 mg (66%) of the acid. mp=197-200° C. $^1$H NMR (400 MHz, DMSO) δ 12.03 (s, 1H), 8.32 (s, 1H), 7.47 (d, J=8.3 Hz, 2H), 7.45 (d, J=15.9 Hz, 1H), 6.99 (dd, J=8.6, 2.4 Hz, 1H), 6.94 (dd, J=9.3, 5.6 Hz, 2H), 6.88 (d, J=8.6 Hz, 2H), 6.21 (d, J=15.8 Hz, 1H), 3.77 (s, 3H), 2.02 (s, 9H), 1.72 (s, 6H). HRMS (TOF MS ES+) for C$_{25}$H$_{30}$NO$_3$$^+$ (MH+) calcd. 404.2226, found 404.2191.

Example 37: (2E)-3-(4-{[3-(adamantan-1-yl)-4-hydroxyphenyl]amino}phenyl)prop-2-enoic Acid

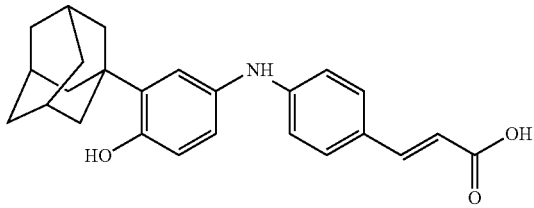 [SMILES: O=C(O)/C=C/c1ccc(Nc2ccc(O)c(C34CC5CC(CC(C5)C3)C4)c2)cc1]

(2E)-3-(4-{[3-(adamantan-1-yl)-4-hydroxyphenyl]amino}phenyl)prop-2-enoic acid was prepared according to example 31 starting from 32 mg of (2E)-3-(4-{[3-(adamantan-1-yl)-4-methoxyphenyl]amino}phenyl)prop-2-enoic acid. The residue was purified on a HP-Sil 25 g Biotage SNAP cartridge and eluted with EtOAc:cyclohexane using a gradient (0-25%) at a flow rate of 20 mL/min to provide a yellow solid (25 mg, 80%). mp=decomposes at 152° C. $^1$H NMR (400 MHz, DMSO) δ 12.01 (s, 1H), 9.05 (s, 1H), 8.17 (s, 1H), 7.50-7.39 (m, 3H), 6.86 (dd, J=9.8, 2.2 Hz, 2H), 6.82 (d, J=8.7 Hz, 3H), 6.73 (d, J=8.3 Hz, 1H), 6.19 (d, J=15.9 Hz, 1H), 2.06 (s, 6H), 2.02 (s, 3H), 1.72 (s, 6H). HRMS (TOF MS ES+) for $C_{23}H_{23}NO_3^+$ (MH+) calcd. 390.2069, found 390.2045.

Example 38: 3-(4-{[3-(adamantan-1-yl)-4-methoxyphenyl]amino}phenyl)propanoic Acid

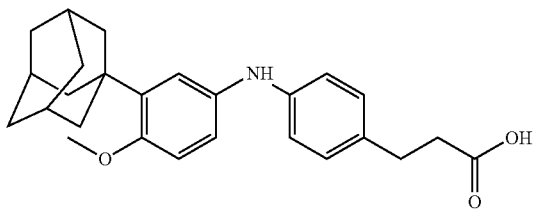 [SMILES: COc1ccc(Nc2ccc(CCC(=O)O)cc2)cc1C12CC3CC(CC(C3)C1)C2]

Benzyl (2E)-3-(4-{[3-(adamantan-1-yl)-4-methoxyphenyl]amino}phenyl)prop-2-enoate (660 mg, 1.33 mmol) was placed in a hydrogenation apparatus equipped with a magnetic stir bar and 50 mL ethanol/EtOAc added. Pd/C (300 mg) in a small amount of MeOH (3 mL) was added and stirring commenced. Hydrogen gas was introduced at a pressure of 20 psi and reacted at rt for 5 hrs. TLC showed full conversion. The black solution was filtered using a celite pad and concentrated under reduced pressure. Further purification on Biotage yielded a brown solid, 200 mg (30%). mp=164-166° C. $^1$H NMR (400 MHz, CDCl$_3$) δ 8.39 (s, 1H), 7.05 (d, J=8.1 Hz, 2H), 6.95 (m, 2H), 6.85 (d, J=7.4 Hz, 2H), 6.80 (d, J=8.5 Hz, 1H), 3.81 (s, 3H), 2.87 (d, J=7.0 Hz, 2H), 2.65 (t, J=7.7 Hz, 2H), 2.07 (s, 9H), 1.76 (s, 6H). HRMS (TOF MS ES+) for $C_{26}H_{32}NO_3^+$ (MH+) calcd. 406.2382, found 406.2410.

Example 39: 3-(4-{[3-(adamantan-1-yl)-4-hydroxyphenyl]amino}phenyl)propanoic Acid

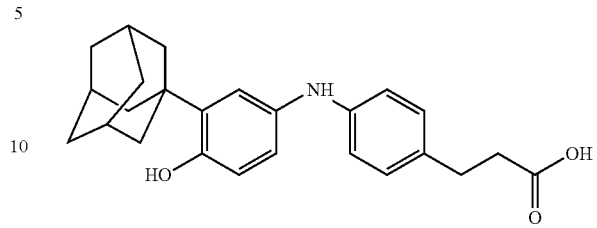

3-(4-{[3-(adamantan-1-yl)-4-hydroxyphenyl]amino}phenyl)propanoic acid was prepared according to example 31 starting from 80 mg of 3-(4-{[3-(adamantan-1-yl)-4-methoxyphenyl]amino}phenyl)propanoic acid. The residue was purified on Biotage to provide a dark green solid (58 mg, 75%). mp=94-96° C. $^1$H NMR (400 MHz, DMSO) δ 12.05 (s, 1H), 8.83 (s, 1H), 6.98 (d, J=8.4 Hz, 2H), 6.81 (d, J=2.5 Hz, 1H), 6.77 (d, J=8.4 Hz, 2H), 6.74 (dd, J=8.3, 2.5 Hz, 1H), 6.65 (d, J=8.4 Hz, 1H), 2.68 (t, J=7.6 Hz, 2H), 2.45 (t, J=7.6 Hz, 2H), 2.05 (s, 6H), 2.01 (s, 3H), 1.71 (s, 6H). HRMS (TOF MS ES+) for $C_{25}H_{30}NO_3^+$ (MH+) calcd, 392.2226, found 392.2246.

Example 40: Benzyl (2E)-3-{4-[(3-tert-butyl-4-methoxyphenyl)amino]phenyl}prop-2-enoate 4-bromo-2-tert-butylphenol

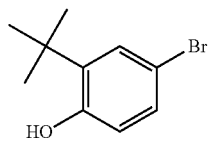

4-bromo-2-tert-butylphenol was prepared according to a procedure described by Berthelot and al. (Can. J. Chem, 1989, 67, 2061-2066). To a solution of 2-tert-butylphenol (154 mL, 1 mmol, 1 eq.) in chloroform (5 mL) was added a solution of TBABr$_3$ (482 mg, 1 mmol, 1 eq.) in chloroform (5 mL). The orange solution became colorless within 5 minutes. A solution of 5% sodium thiosulfate was added (15 mL). The organic layer is extracted with chloroform (2×20 mL), washed with water until pH=7, and evaporated. The crude oil is then diluted in diethyl ether (50 mL) and washed with water again (2×20 mL). The organic layer is then dried over Ca$_2$SO$_4$ and concentrated to dryness to afford a yellow solid (201 mg, 88%). mp=101° C. No further purification is needed. $^1$H NMR (400 MHz, CHLOROFORM-d) δ ppm 1.38 (s, 9H), 4.96 (s, 1H), 6.58 (d, J=8.37 Hz, 1H), 7.15 (dd, J=8.37, 2.41 Hz, 1H), 7.34 (d, J=2.41 Hz, 1H).

(a) 4-bromo-2-tert-butyl-1-methoxybenzene

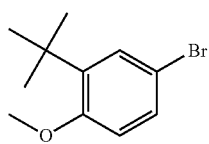

4-bromo-2-test-butyl-1-methoxybenzene was prepared according to example 55(a), starting from 610 mg of 4-bromo-2-tert-butylphenol. A light orange oil is obtained (500 mg, 78%). $^1$H NMR (400 MHz, CHLOROFORM-d) δ ppm 1.34 (m, 9H,), 3.81 (m, 3H), 6.73 (d, J=8.66 Hz, 1H), 7.23-7.29 (m, 1H), 7.35 (d, J=2.38 Hz, 1H).

(b) 3-tert-butyl-4-methoxyphenyl)boronic Acid

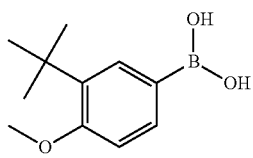

3-tert-butyl-4-methoxyphenyl)boronic acid was prepared according to example 32(b), starting from 500 mg of 4-bromo-2-tert-butyl-1-methoxybenzene. The crude sticky oil obtained, was used in the following step without any purification.

(c) benzyl (2E)-3-{4-[(3-tert-butyl-4-methoxyphenyl)amino]phenyl}prop-2-enoate

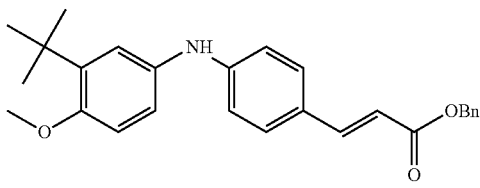 [SMILES: COc1ccc(Nc2ccc(/C=C/C(=O)OCc3ccccc3)cc2)cc1C(C)(C)C]

Benzyl (2E)-3-{4-[(3-tert-butyl-4-methoxyphenyl)amino]phenyl}prop-2-enoate was obtained according to example 35(e), starting from 100 mg of 3-tert-butyl-4-methoxyphenyl)boronic acid. a\After purification by column chromatography using the following gradient system, (cyclohexane/ethyl acetate): (97/3) to (60/40), to yield the title compound as colorless oil (60 mg, 60%). $^1$H NMR (400 MHz, CHLOROFORM-d) δ ppm 1.34 (m, 9H), 3.84 (s, 3H), 5.23 (s, 2H), 5.77 (s, 1H), 6.29 (d, J=15.87 Hz, 1H), 6.83 (t, J=8.22 Hz, 3H), 6.95-7.11 (m, 2H), 7.29-7.47 (m, 7H), 7.65 (d, J=15.87 Hz, 1H).

Example 41: 3-{4-[(3-tert-butyl-4-methoxyphenyl)amino]phenyl}propanoic Acid

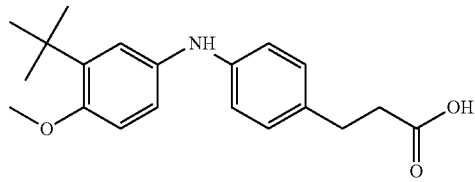 [SMILES: COc1ccc(Nc2ccc(CCC(=O)O)cc2)cc1C(C)(C)C]

3-{4-[(3-tert-butyl-4-methoxyphenyl)amino]phenyl}propanoic acid was prepared according to example 38, starting from 2245 mg of benzyl (2E)-3-{4-[(3-tert-butyl-4-methoxyphenyl)amino]phenyl}prop-2-enoate. A black sticky oil was obtained (73 mg, 38%). $^1$H NMR (400 MHz, CHLOROFORM-d) δ ppm 1.36 (s, 9H), 2.65 (t, J=7.75 Hz, 2H), 2.88 (t, J=7.75 Hz, 2H), 3.82 (s, 3H), 5.30 (s, 1H), 6.76-6.90 (m, 3H), 6.96 (dd, J=8.53, 2.64 Hz, 1H), 6.99-7.12 (m, 3H). HRMS (TOF MS ES−) for C20H24NO3− (M−H)− calcd. 326.1756, found 326.1740.

Scheme 5

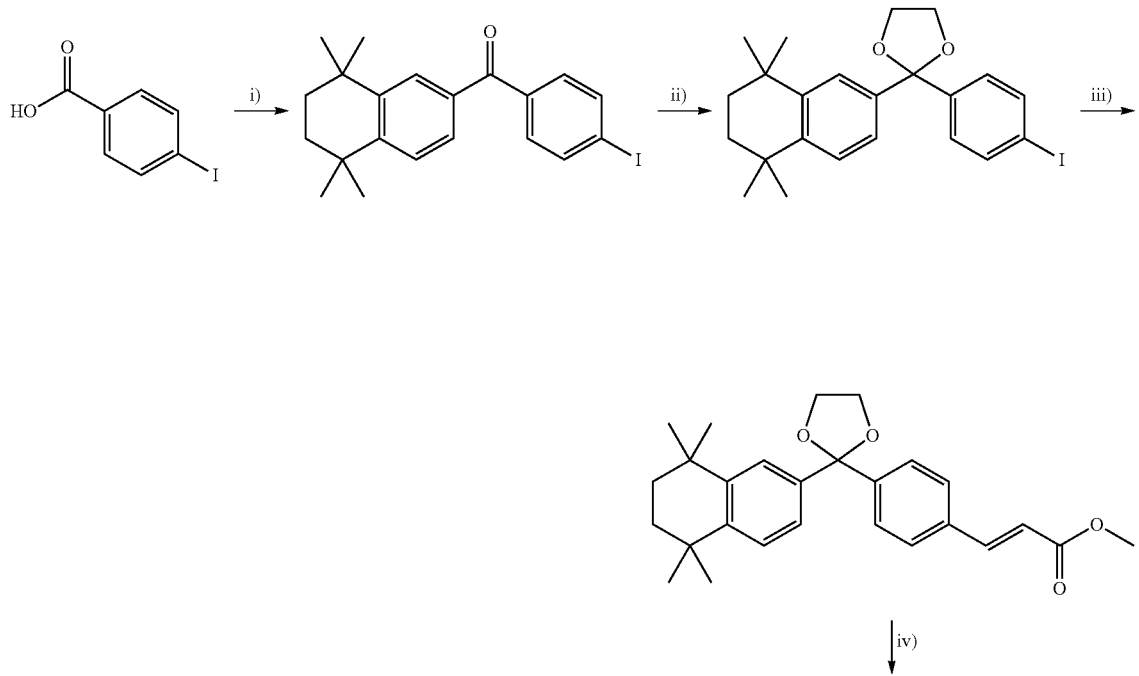

-continued

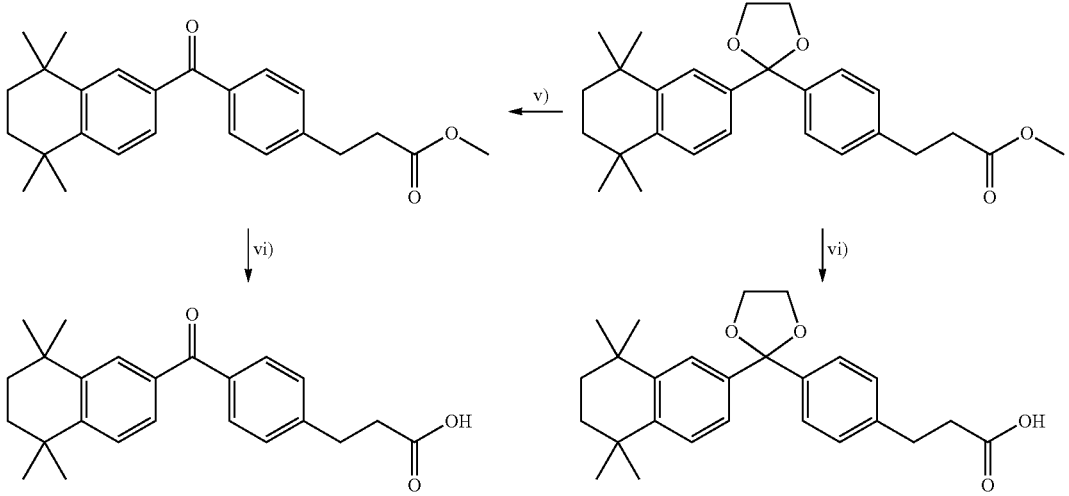

i) 1) SOCl₂, DMF, DCE, reflux, 1 h; 2) 1,1,4,4-tetramethyl-1,2,3,4-tetrahydronaphthalene, AlCl₃, r.t., 2 h;
ii) ethylene glycol, pTsOH, toluene, reflux; overnight; iii) methyl acrylate, Pd(OAc)₂, NEt₃, DMF, 100° C., 3 h;
iv) H₂, Pd/C, EtOH, EtOAc, MeOH, 20 psi, overnight; v) I₂, acetone, MS 4Å, reflux, 14 h ; vi) LiOH 1N, THF, r.t. overnight.

Example 42: Methyl (2E)-3-{4-[2-(5,5,8,8-tetramethyl-5,6,7,8-tetrahydronaphthalen-2-yl)-1,3-dioxolan-2-yl]phenyl}prop-2-enoate (a) (4-iodophenyl)(5,5,8,8-tetramethyl-5,6,7,8-tetrahydronaphthalen-2-yl)methanone

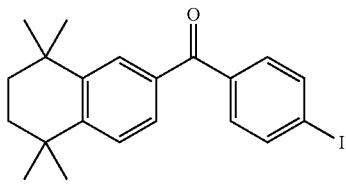 [SMILES: CC1(C)CCC(C)(C)c2cc(C(=O)c3ccc(I)cc3)ccc21]

Compound was prepared according to the procedure described by Boehm et al. (J. Med. Chem. 1994, 37, 2930-2941) starting from 4 g of 4-iodobenzoic acid (16.1 mmol). After work-up, the crude product was purified by column chromatography using the following gradient system, (cyclohexane/dichloromethane): (80/20) to (0/100), to yield the title compound as a light orange solid, 2.8 g (50%). mp=7576° C. ¹H NMR (400 MHz, CHLOROFORM-d) δ 1.31 (2 s, 12H), 1.72 (s, 4H), 7.40 (d, J=8.16 Hz, 1H), 7.45-7.60 (m, 3H), 7.75 (d, J=1.63 Hz, 1H), 7.84 (d, J=8.28 Hz, 2H).

(b) 2-(4-iodophenyl)-2-(5,5,8,8-tetramethyl-5,6,7,8-tetrahydronaphthalen-2-yl)-1,3-dioxolane

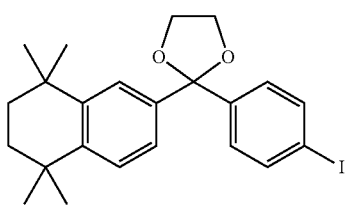 [SMILES: CC1(C)CCC(C)(C)c2cc(C3(c4ccc(I)cc4)OCCO3)ccc21]

(4-iodophenyl)(5,5,8,8-tetramethyl-5,6,7,8-tetrahydronaphthalen-2-yl)methanone (2 g, 4.78 mmol) was treated with ethylene glycol (20 mL) and a catalytic amount of pTsOH (200 mg) in toluene (120 mL) at 145° C. overnight using a Dean Stark trap. After cooling to r.t., the mixture was washed with saturated aqueous NaHCO₃, brine, dried over Ca₂SO₄ and concentrated under reduced pressure. The residue was purified by column chromatography using the following gradient system, (cyclohexane/dichloromethane): (80/20) to (0/100), to yield the title compound as a white solid (1.1 g, 50%) and the starting material (1 g). The reaction was repeated by sequences with the unreacted ketone until fully converted. mp=116-117° C. ¹H NMR (400 MHz, CHLOROFORM-d) δ 1.24 (2 s, 12H), 1.65 (s, 4H), 3.85-4.15 (m, 4H), 7.14 (dd, J=1.76, 8.16 Hz, 1H), 7.22 (d, J=8.16 Hz, 1H), 7.28 (s, 1H), 7.38-7.46 (m, 1H), 7.65 (d, J=8.53 Hz, 3H).

(c) Methyl (2E)-3-{4-[2-(5,5,8,8-tetramethyl-5,6,7,8-tetrahydronaphthalen-2-yl)-1,3-dioxolan-2-yl]phenyl}prop-2-enoate

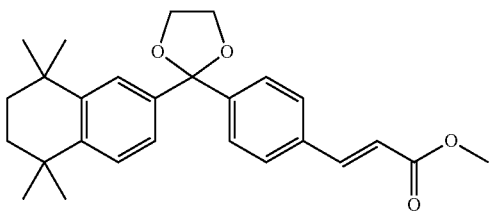 [SMILES: COC(=O)/C=C/c1ccc(C2(c3ccc4c(c3)C(C)(C)CCC4(C)C)OCCO2)cc1]

To a stirred solution of 2-(4-iodophenyl)-2-(5,5,8,8-tetramethyl-5,6,7,8-tetrahydronaphthalen-2-yl)-1,3-dioxolane (1.02 g, 2.2 mmol, 1 eq.) and Et₃N (920 μL, 6.6 mmol, 3 eq.) were added methyl acrylate (300 μL, 3.3 mmol, 1.5 eq.) and palladium (II) acetate (15 mg, 0.1 eq.). The resulting mixture was heated at 100° C. for 3 hours. The reaction mixture was allowed to cool to r.t., concentrated under reduced pressure and purified by column chromatography using the following gradient system, (cyclohexane/dichloromethane): (80/20) to (0/100), to yield the title compound as a white solid, 0.75 g (80%). mp=168-170° C. 1H NMR (400 MHz, CHLOROFORM-d) δ 1.24 (2 s, 12H), 1.65 (s, 4H), 3.80 (s, 3H), 3.96-4.14 (m, 4H), 6.42 (d, J=15.94 Hz, 1H), 7.13-7.20 (m, 1H), 7.23 (d, J=8.16 Hz, 1H), 7.40-7.60 (m, 5H), 7.67 (d, J=15.94 Hz, 1H).

Example 43: Methyl 3-{4-[2-(5,5,8,8-tetramethyl-5,6,7,8-tetrahydronaphthalen-2-yl)-1,3-dioxolan-2-yl]phenyl}propanoate

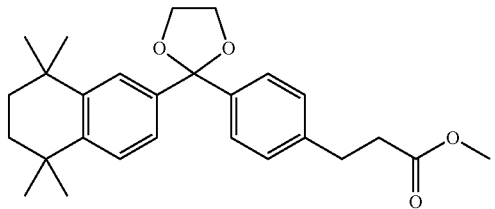 [SMILES: COC(=O)CCc1ccc(C2(c3ccc4c(c3)C(C)(C)CCC4(C)C)OCCO2)cc1]

A solution of methyl (2E)-3-{4-[2-(5,5,8,8-tetramethyl-5,6,7,8-tetrahydronaphthalen-2-yl)-1,3-dioxolan-2-yl]phenyl}prop-2-enoate (750 mg, 1.78 mmol) in 60 mL of (EtOH/EtOAc: (9/1) was placed in a hydrogenation apparatus equipped with a magnetic stir bar. Pd/C (410 mg) in a small amount of MeOH (2 mL) was added. Hydrogen gas was introduced at a pressure of 20 psi and reacted at r.t. overnight. The black solution was filtered using a celite pad and concentrated under reduced pressure. Further purification by chromatography yielded the title compound as a white solid, 520 mg (70%). mp 120-122° C. $^1$H NMR (400 MHz, CHLOROFORM-d) δ 1.24 (2 s, 12H), 1.65 (s, 4H), 2.61 (t, J=7.84 Hz, 2H), 2.93 (t, J=7.84 Hz, 2H), 3.66 (s, 3H), 3.93-4.13 (m, 4H), 7.10-7.19 (m, 3H), 7.19-7.24 (m, 3H), 7.38-7.49 (m, 3H).

Example 44: 3-{4-[2-(5,5,8,8-tetramethyl-5,6,7,8-tetrahydronaphthalen-2-yl)-1,3-dioxolan-2-yl]phenyl}propanoic Acid

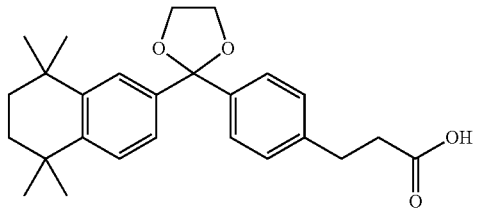 [SMILES: CC1(C)CCC(C)(C)c2cc(C3(c4ccc(CCC(=O)O)cc4)OCCO3)ccc21]

3-{4-[2-(5,5,8,8-tetramethyl-5,6,7,8-tetrahydronaphthalen-2-yl)-1,3-dioxolan-2-yl]phenyl}propanoic acid was prepared according to example 3 starting from 250 mg of methyl 3-{4-[2-(5,5,8,8-tetramethyl-5,6,7,8-tetrahydronaphthalen-2-yl)-1,3-dioxolan-2-yl]phenyl}propanoate (example 43). The title compound was obtained as a white solid (220 mg, 91%). mp=219°-220° C. $^1$H NMR (400 MHz, CHLOROFORM-d) δ ppm 1.23 (s, 6H), 1.24 (s, 6H), 1.65 (s, 4H), 2.66 (t, J=7.78 Hz, 2H), 2.94 (t, J=7.84 Hz, 2H), 3.97-4.09 (m, 4H), 7.17 (m, 3H), 7.19-7.24 (d, J=8.28 Hz 1H), 7.44 (m, 3H). HRMS (ESI+) [M+H]$^+$ for $C_{25}H_{33}O_4^+$ (MH$^+$) 419.0836, calc. 419.0866.

Example 45: Methyl 3-[4-(5,5,8,8-tetramethyl-5,6,7,8-tetrahydronaphthalene-2-carbonyl)phenyl]propanoate

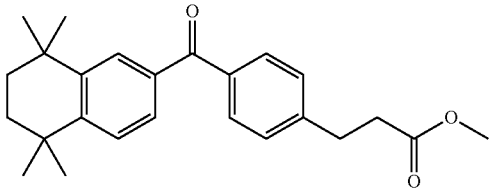 [SMILES: COC(=O)CCc1ccc(C(=O)c2ccc3c(c2)C(C)(C)CCC3(C)C)cc1]

A mixture of methyl 3-{4-[2-(5,5,8,8-tetramethyl-5,6,7,8-tetrahydronaphthalen-2-yl)-1,3-dioxolan-2-yl]phenyl}propanoate (265 mg, 0.63 mmol, 1 eq.), iodine (160 mg, 0.63 mmol, 1 eq.) and 4 Å molecular sieves (250 mg) in acetone (6 mL) was stirred for 8 hours under reflux according to a modified method of Sun et al, (J. Org. Chem. 2004, 69, 8932-8934.). After work-up and purification by column chromatography using the following gradient system, (cyclohexane/dichloromethane): (80/20) to (20/80), the title compound was obtained as a colorless oil (150 mg, 63%). $^1$H NMR (400 MHz, CHLOROFORM-d) δ ppm 1.30 (s, 6H), 1.31 (s, 6H), 1.72 (s, 4H), 2.69 (t, J=7.72 Hz, 2H), 3.04 (t, J=7.78 Hz, 2H), 3.69 (s, 3H), 7.31 (d, J=7.91 Hz, 2H), 7.39 (d, J=8.16 Hz, 1H), 7.53 (d, J=8.16 Hz, 1H), 7.71-7.80 (m, 3H).

Example 46: 3-[4-(5,5,8,8-tetramethyl-5,6,7,8-tetrahydronaphthalene-2-carbonyl)phenyl]propanoic Acid

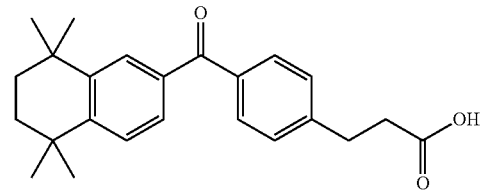 [SMILES: CC1(C)CCC(C)(C)c2cc(C(=O)c3ccc(CCC(=O)O)cc3)ccc21]

3-[4-(5,5,8,8-tetramethyl-5,6,7,8-tetrahydronaphthalene-2-carbonyl)phenyl]propanoic acid was prepared according to example 3 using 50 mg of corresponding ester (example 45). A white solid is obtained (220 mg, 91%). mp=153°-155° C. $^1$H NMR (400 MHz, CHLOROFORM-d) δ 1.31 (2 s, 12H), 1.72 (s, 6H), 2.75 (t, J=7.72 Hz, 2H), 3.05 (t, J=7.72 Hz, 2H), 7.32 (d, J=8.16 Hz, 2H), 7.39 (d, J=8.28 Hz, 1H), 7.53 (dd, J=1.82, 8.22 Hz, 1H), 7.70-7.83 (m, 3H). HRMS (ESI+) [M+H]$^+$ for $C_{23}H_{29}O_3^+$ (MH$^+$) 419.0836, calc. 419.0866.

Example 47: Methyl (2E)-3-{4-[(5,5,8,8-tetramethyl-5,6,7,8-tetrahydronaphthalen-2-yl)carbonyl]phenyl}prop-2-enoate

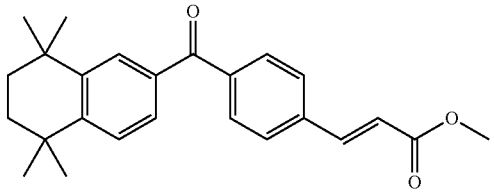 [SMILES: COC(=O)/C=C/c1ccc(C(=O)c2ccc3c(c2)C(C)(C)CCC3(C)C)cc1]

Methyl (2E)-3-{4-[(5,5,8,8-tetramethyl-5,6,7,8-tetrahydronaphthalen-2-yl)carbonyl]phenyl}-prop-2-enoate was prepared according to example 42(c) starting from 1.65 g of (4-iodophenyl)(5,5,8,8-tetramethyl-5,6,7,8-tetrahydronaphthalen-2-yl)methanone. The crude was purified on Biotage to yield a yellow solid, 1.22 g (82%), mp=138-140° C. $^1$H NMR (400 MHz, CDCl$_3$) δ 7.82 (d, J=8.3 Hz, 2H), 7.79 (d, J=1.8 Hz, 1H), 7.75 (d, J=16.1 Hz, 1H), 7.63 (d, J=8.3 Hz, 2H), 7.54 (dd, J=8.2, 1.9 Hz, 1H), 7.41 (d, J=8.2 Hz, 1H), 6.55 (d, 16.0 Hz, 1H), 3.83 (s, 3H), 1.72 (s, 4H), 1.32 (s, 6H), 1.30 (s, 6H).

Example 48: Methyl (2E)-3-{4-[2-(5,5,8,8-tetramethyl-5,6,7,8-tetrahydronaphthalen-2-yl)-1,3-dithiolan-2-yl]phenyl}prop-2-enoate

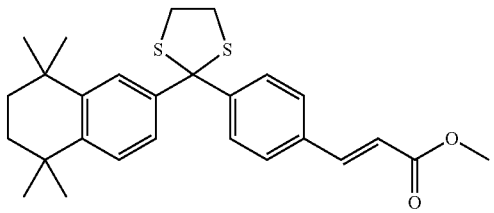 [SMILES: COC(=O)/C=C/c1ccc(C2(c3ccc4c(c3)C(C)(C)CCC4(C)C)SCCS2)cc1]

To a solution of methyl (2E)-3-{4-[(5,5,8,8-tetramethyl-5,6,7,8-tetrahydronaphthalen-2-yl)carbonyl]phenyl}prop-2-enoate (0.35 g, 0.93 mmol) example 47, in CH$_2$Cl$_2$ (20 mL) at 0° C. under Ar was added a solution of ethanedithiol (117 mL, 1.40 mmol, 1.5 eq.) in CH$_2$Cl$_2$ (0.5 mL) followed by BF$_3$.Et$_2$0 (177 µL, 1.40 mmol,). The resulting mixture was stirred at 0° C. for 1 h and then warmed to room temperature overnight. The reaction was quenched by pouring the mixture into saturated Na$_2$CO$_3$, and the mixture was extracted (CH$_2$Cl$_2$). The combined organic layers were dried (MgSO$_4$) and concentrated to afford a colorless oil (380 mg (91%). $^1$H NMR (400 MHz, CDCl$_3$) δ 7.67 (d, J=16.2 Hz, 1H), 7.66 (d, J=8.4 Hz, 2H), 7.50 (d, J=2.0 Hz, 1H), 7.44 (d, J=8.4 Hz, 2H), 7.22 (dd, J=8.4, 2.1 Hz, 1H), 7.18 (d, J=8.3 Hz, 1H), 6.42 (d, J=16.0 Hz, 1H), 3.80 (s, 3H), 3.50-3.40 (m, 2H), 3.42-3.32 (m, 2H), 1.66 (s, 4H), 1.25 (s, 6H), 1.21 (s, 6H).

Example 49: (2E)-3-{4-[2-(5,5,8,8-tetramethyl-5,6,7,8-tetrahydronaphthalen-2-yl)-1,3-dithiolan-2-yl]phenyl}prop-2-enoic Acid

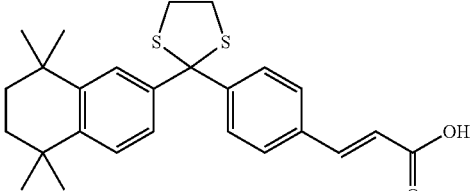

(2E)-3-{4-[2-(5,5,8,8-tetramethyl-5,6,7,8-tetrahydronaphthalen-2-yl)-1,3-dithiolan-2-yl]phenyl}prop-2-enoic acid was prepared according to example 3 starting from 85 mg of methyl (2E)-3-{4-[2-(5,5,8,8-tetramethyl-5,6,7,8-tetrahydronaphthalen-2-yl)-1,3-dithiolan-2-yl]phenyl}prop-2-enoate. Title compound was obtained as a white solid, 81 mg (97%). mp=234-236° C. $^1$H NMR (400 MHz, CDCl$_3$) δ 7.77 (d, J=15.9 Hz, 1H), 7.68 (d, J=8.4 Hz, 2H), 7.50 (d, J=2.0 Hz, 1H), 7.47 (d, J=8.4 Hz, 2H), 7.22 (dd, J=8.4, 2.1 Hz, 1H), 7.18 (d, J=8.3 Hz, 1H), 6.43 (d, J=16.0 Hz, 1H), 3.46 (ddd, J=12.3, 9.4, 7.4 Hz, 2H), 3.42-3.34 (m, 2H), 1.66 (s, 4H), 1.25 (s, 6H), 1.21 (s, 6H), HRMS (TOF MS ES+) for C$_{26}$H$_{34}$O$_2$S$_2$ (MH$^+$) calcd. 439.1765, found 439.1765.

Example 50: (2E)-3-{4-[(5,5,8,8-tetramethyl-5,6,7,8-tetrahydronaphthalen-2-yl)carbonyl]phenyl}prop-2-enoic Acid

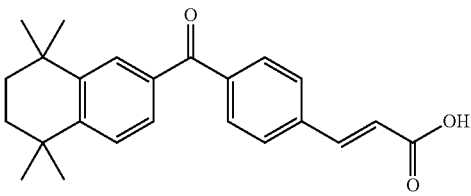 [SMILES: CC1(C)CCC(C)(C)c2cc(C(=O)c3ccc(/C=C/C(=O)O)cc3)ccc21]

(2E)-3-{4-[(5,5,8,8-tetramethyl-5,6,7,8-tetrahydronaphthalen-2-yl)carbonyl]phenyl}prop-2-enoic acid was prepared according to example 3, starting from 310 mg of methyl (2E)-3-{4-[(5,5,8,8-tetramethyl-5,6,7,8-tetrahydronaphthalen-2-yl)carbonyl]phenyl}prop-2-enoate. The crude was purified on Biotage to provide a white solid (278 mg, 93%). mp=220-221° C., $^1$H NMR (400 MHz, CDCl$_3$) δ 7.85 (d, J=16.8 Hz, 1H), 7.84 (d, J=8.0 Hz, 1H), 7.80 (d, J=1.8 Hz, 1H), 7.66 (d, J=8.2 Hz, 2H), 7.54 (dd, J=8.2, 1.8 Hz, 1H), 7.41 (d, J=8.2 Hz, 1H), 6.57 (d, J=16.0 Hz, 1H), 1.73 (s, 4H), 1.32 (s, 6H), 1.30 (s, 6H).

Example 51: Methyl 3-{4-[2-(5,5,8,8-tetramethyl-5,6,7,8-tetrahydronaphthalen-2-yl)-1,3-dithiolan-2-yl]phenyl}propanoate

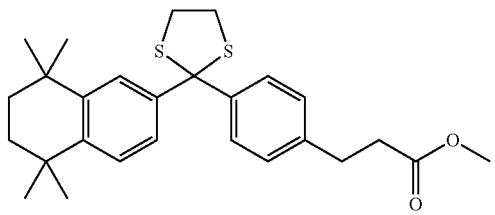 [SMILES: COC(=O)CCc1ccc(C2(c3ccc4c(c3)C(C)(C)CCC4(C)C)SCCS2)cc1]

Methyl 3-{4-[2-(5,5,8,8-tetramethyl-5,6,7,8-tetrahydronaphthalen-2-yl)-1,3-dithiolan-2-yl]phenyl}propanoate was prepared according to example 48, starting from 30 mg of methyl 3-[4-(5,5,8,8-tetramethyl-5,6,7,8-tetrahydronaphthalene-2-carbonyl)phenyl]propanoate to provide a colorless oil (25 mg, 69%). $^1$H NMR (400 MHz, CDCl$_3$) δ 7.54 (d, J=8.4 Hz, 2H), 7.52 (d, J=2.1 Hz, 1H), 7.22 (dd, J=8.4, 2.2 Hz, 1H), 7.16 (d, J=8.4 Hz, 1H), 7.11 (d, J=8.3 Hz, 2H), 3.67 (s, 3H), 3.48-3.29 (m, 4H), 2.93 (t, J=7.9 Hz, 2H), 2.62 (t, J=7.9 Hz, 2H), 1.65 (s, 4H), 1.24 (s, 6H), 1.21 (s, 6H).

Example 52: 3-{4-[2-(5,5,8,8-tetramethyl-5,6,7,8-tetrahydronaphthalen-2-yl)-1,3-dithiolan-2-yl]phenyl}propanoic Acid

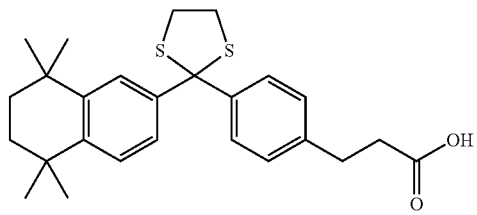

3-{4-[2-(5,5,8,8-tetramethyl-5,6,7,8-tetrahydronaphthalen-2-yl)-1,3-dithiolan-2-yl]phenyl}propanoic acid was prepared according to example 3, starting from 25 mg of Methyl 3-{4-[2-(5,5,8,8-tetramethyl-5,6,7,8-tetrahydronaphthalen-2-yl)-1,3-dithiolan-2-yl]phenyl}propanoate. The residue was purified on Biotage to give title compound as a yellow solid (15 mg, 63%), mp=165-167° C. $^1$H NMR (400 MHz, CDCl$_3$) δ 7.55 (d, J=8.3 Hz, 2H), 7.52 (d, J=2.1 Hz, 1H), 7.22 (dd, J=8.4, 2.2 Hz, 1H), 7.16 (d, J=8.4 Hz, 1H), 7.12 (d, J=7.4 Hz, 2H), 3.49-3.32 (m, 4H), 2.94 (t, J=7.8 Hz, 2H), 2.67 (t, J=7.8 Hz, 2H), 1.65 (s, 4H), 1.25 (d, J=1.7 Hz, 6H), 1.21 (s, 6H). HRMS (TOF MS ES+) for C$_{26}$H$_{33}$O$_2$S$_2^-$ (MH+) calcd. 441.1922, found 441.1918.

Example 53: Methyl 3-{4-[(5,5,8,8-tetramethyl-5,6,7,8-tetrahydronaphthalen-2-yl)methyl]phenyl}propanoate

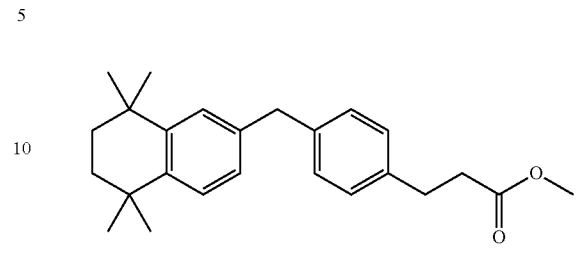

Methyl 3-{4-[(5,5,8,8-tetramethyl-5,6,7,8-tetrahydronaphthalen-2-yl)methyl]phenyl}-propanoate was prepared according to example 38, starting from 515 mg of methyl (2E)-3-{4-[(5,5,8,8-tetramethyl-5,6,7,8-tetrahydronaphthalen-2-yl)carbonyl]phenyl}prop-2-enoate. The crude was purified on a 50 g Biotage cartridge using an EtOAc:cyclohexane gradient (0-10%) to provide a colorless oil (479 mg, 93%). $^1$H NMR (400 MHz, CDCl$_3$) δ 7.19 (d, J=8.1 Hz, 1H), 7.15-7.08 (Aroamtic, 5H), 6.90 (dd, J=8.1, 1.9 Hz, 1H), 3.89 (s, 2H), 3.65 (s, 3H), 2.91 (t, J=7.9 Hz, 2H), 2.61 (t, J=7.9 Hz, 2H), 1.66 (s, 4H), 1.25 (s, 12H).

Example 54: 3-{4-[(5,5,8,8-tetramethyl-5,6,7,8-tetrahydronaphthalen-2-yl)methyl]phenyl}propanoic Acid

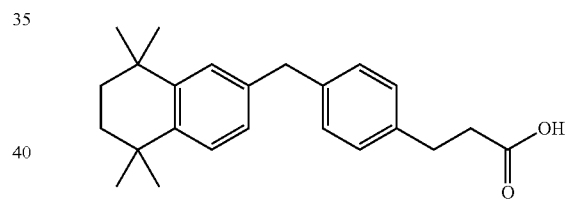

3-{4-[(5,5,8,8-tetramethyl-5,6,7,8-tetrahydronaphthalen-2-yl)methyl]phenyl}propanoic acid was prepared according to example 3, starting from 422 mg of methyl 3-{4-[(5,5,8,8-tetramethyl-5,6,7,8-tetrahydronaphthalen-2-yl)methyl]phenyl}propanoate. The crude was purified on a Biotage SNAP cartridge and eluted with 5% MeOH:CH$_2$Cl$_2$ to provide a white solid (301 mg, 77%). $^1$H NMR (400 MHz, CDCl$_3$) δ 7.20 (d, J=8.1 Hz, 1H), 7.12 (5H), 6.90 (dd, J=8.1, 1.8 Hz, 1H), 3.89 (s, 2H), 2.92 (t, J=7.8 Hz, 2H), 2.66 (t, J=7.8 Hz, 2H), 1.66 (s, 4H), 1.25 (s, 12H). mp=142-143° C. HRMS (TOF MS ES+) for C$_{24}$H$_{31}$O$_2$ (MH+) calcd. 351.2324, found 351.2321.

Scheme 6

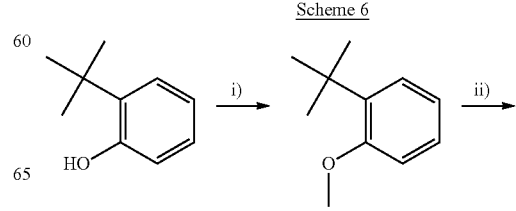

57
-continued

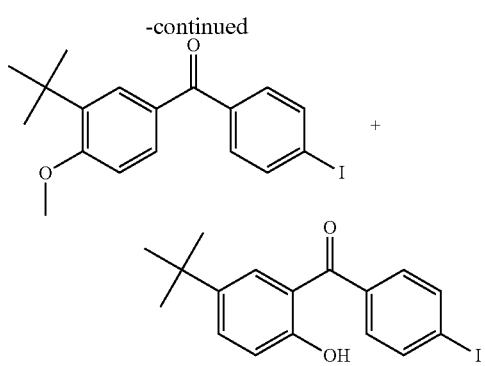

i) 1) NaH, DMF, 2) CH₃I; ii) 4-iodobenzyl chloride, AlCl₃, DCM.

58

Example 55: Benzyl (2E)-3-{4[(3-tert-butyl-4-methoxyphenyl)carbonyl]phenyl}prop-2-enoate (a) 1-tert-butyl-2-methoxybenzene

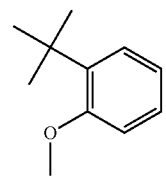

To a suspension of sodium hydroxide (60% in oil, 0.46 g, 1.1 eq.) in DMF (5 mL), was slowly added a solution of Scheme 7

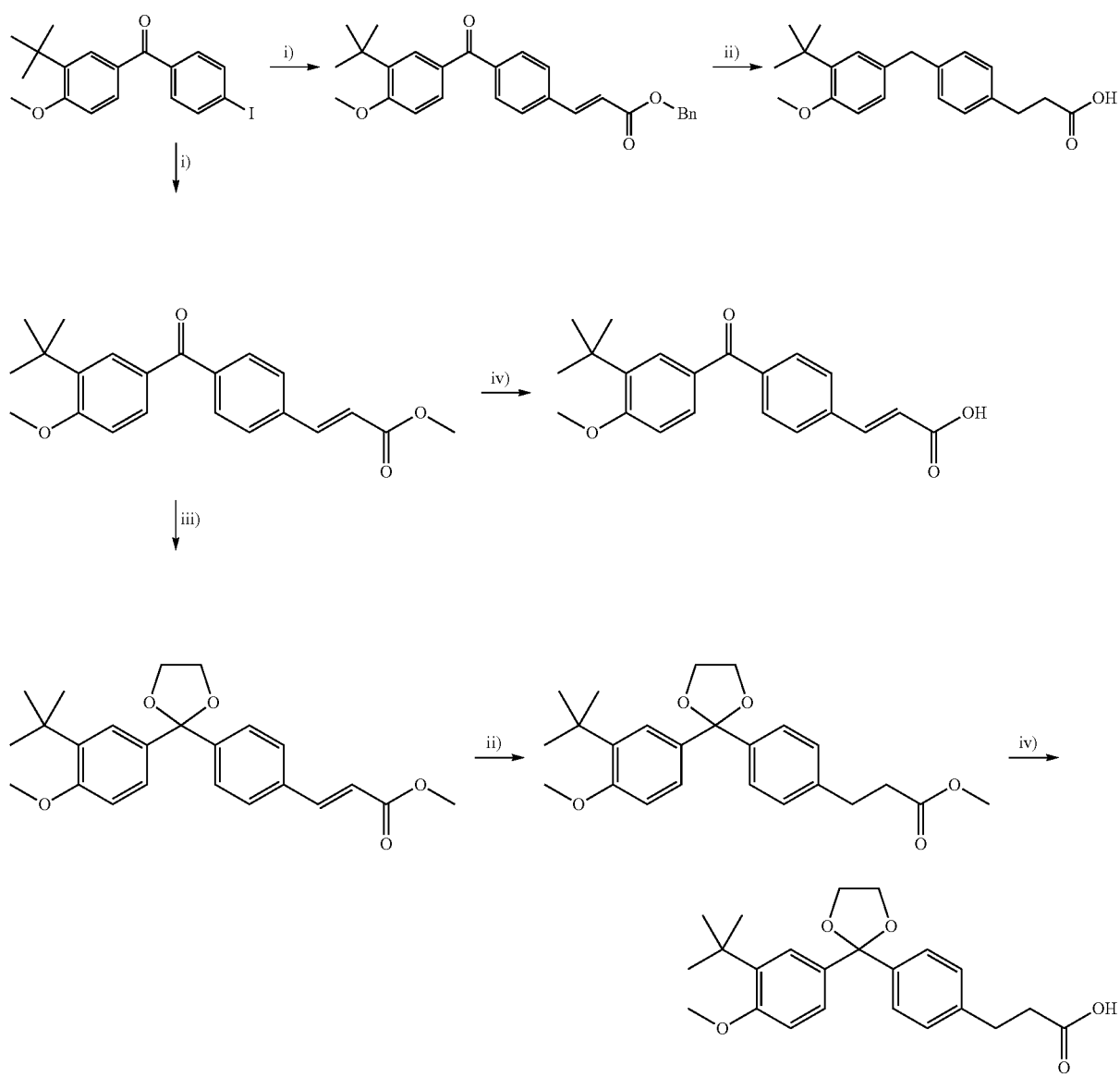

i) methyl or benzyl acrylate, Pd(OAc)₂, NEt₃, DMF, 100° C., 3 h; ii) H₂, Pd/C, EtOH, EtOAc, MeOH, 20 psi, overnight;
iii) ethylene glycol, pTsOH, toluene, reflux; overnight; iv) LiOH 1N, THF, r.t. overnight.

2-tertbutylphenol (1.53 g, 10 mmol, 1 eq.) in DMF (5 mL). The mixture was stirred 1 hour until the solution became clear. Iodomethane (0.68 mL, 1.1 eq.) was the added, and the solution stirred for a further 2 hours. The mixture was poured into water, and extracted with Et₂O. The organic layers were combined, dried with brine and Ca₂SO₄, and concentrated to afford the title compound as a colorless oil (1.40 g, 80%). No further purification was needed. ¹H NMR (400 MHz, CHLOROFORM-d) δ ppm 1.37 (s, 9H), 3.82 (s, 3H), 6.83-6.93 (m, 2H), 7.13-7.23 (m, 1H), 7.28 (dd, J=7.65, 1.38 Hz, 1H).

(b) (3-tert-butyl-4-methoxyphenyl)(4-iodophenyl) methanone

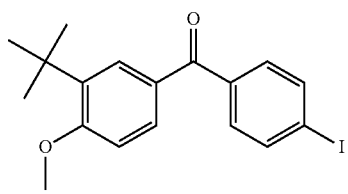 [SMILES: COc1ccc(C(=O)c2ccc(I)cc2)cc1C(C)(C)C]

(3-tert-butyl-4-methoxyphenyl)(4-iodophenyl)methanone was prepared according to example 42(a), starting from 1.40 g of 1-tert-butyl-2-methoxybenzene. Purification of crude by silica gel chromatography using the following gradient system, (cyclohexane/dichloromethane): (80/20) to (0/100), afforded (3-tert-butyl-4-methoxyphenyl)(4-iodophenyl) methanone as a colorless oil (1.1 g, 32%), alongside 4-tert-butyl-2-[(4-iodophenyl)carbonyl]phenol as a yellow solid (1.05 g, 31%). ¹H NMR (400 MHz, CHLOROFORM-d) δ ppm 1.39 (s, 9H) 3.92 (s, 3H) 6.90 (d, J=8.53 Hz, 1H) 7.48 (d, J=8.16 Hz, 2H) 7.63 (dd, J=8.41, 2.01 Hz, 1H) 7.78-7.87 (m, 3H).

(c) 4-tert-butyl-2-[(4-iodophenyl)carbonyl]phenol

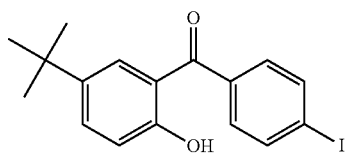 [SMILES: CC(C)(C)c1ccc(O)c(C(=O)c2ccc(I)cc2)c1]

4-tert-butyl-2-[(4-iodophenyl)carbonyl]phenol was obtained in example 55(b). Yellow solid (1.05 g, 30%). mp=101-103° C. ¹H NMR (400 MHz, CHLOROFORM-d) δ ppm 1.25 (s, 9H), 7.02 (d, J=8.78 Hz, 1H), 7.42 (m, J=8.41 Hz, 2H), 7.52 (d, J=2.28 Hz, 1H), 7.58 (dd, J=8.78, 2.28 Hz, 1H), 7.88 (m, J=8.41 Hz, 2H), 11.70 (s, 1H).

(d) Benzyl (2E)-3-{4-[(3-tert-butyl-4-methoxyphenyl)carbonyl]phenyl}prop-2-enoate

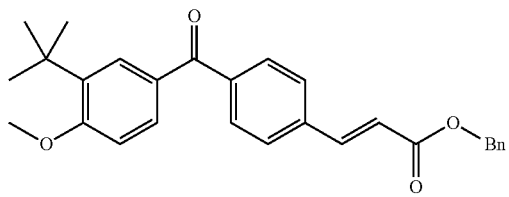 [SMILES: COc1ccc(C(=O)c2ccc(/C=C/C(=O)OCc3ccccc3)cc2)cc1C(C)(C)C]

Ethyl (2E)-3-{4-[(3-tert-butyl-4-methoxyphenyl)carbonyl]phenyl}prop-2-enoate was prepared according example 42(e), starting from 355 mg of (3-tert-butyl-4-methoxyphenyl)(4-iodophenyl)methanone. Purification of the crude by silica gel chromatography using the following gradient system, (cyclohexane/dichloromethane): (20/80) to (0/100), afforded title compound as a colorless oil (330 mg, 85%). ¹H NMR (400 MHz, CHLOROFORM-d) δ ppm 1.39 (s, 9H), 3.93 (s, 3H), 5.27 (s, 2H), 6.59 (d, J=16.06 Hz, 1H), 6.91 (d, J=8.53 Hz, 1H), 7.31-7.47 (m, 5H), 7.56-7.69 (m, 3H), 7.72-7.83 (m, 3H), 7.86 (d, J=2.01 Hz, 1H).

Example 56: 3-{4-[(3-tert-butyl-4-methoxyphenyl) methyl]phenyl}propanoic Acid

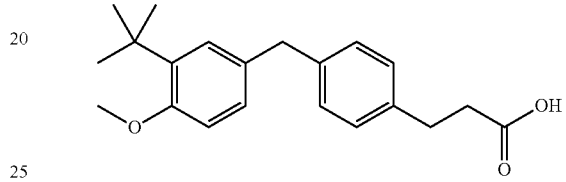

3-{4-[(3-tert-butyl-4-methoxyphenyl)methyl]phenyl}propanoic acid was prepared according to example 38 starting from 330 mg of ethyl (2E)-3-{4-[(3-tert-butyl-4-methoxyphenyl)carbonyl]phenyl}prop-2-enoate. Purification of the crude by silica gel chromatography using the following gradient system, (dichloromethane/methanol): (98/2) to (80/20), afforded the title compound as a light yellow solid (152 mg, 50%). mp=47-48° C. ¹H NMR (400 MHz, CHLOROFORM-d) δ ppm 1.35 (s, 9H), 2.66 (t, J=7.75 Hz, 2H), 2.92 (t, J=7.75 Hz, 2H), 3.80 (s, 3H), 3.88 (s, 2H), 6.78 (d, J=8.28 Hz, 1H), 6.94 (d, J=8.16 Hz, 1H), 7.12 (s, 5H). HRMS (TOF MS ES−) for C21H25O3− (M−H)− calcd. 325.1804, found 325.1801.

Example 57: Methyl (2E)-3-{4-[(3-tert-butyl-4-methoxyphenyl)carbonyl]phenyl}prop-2-enoate

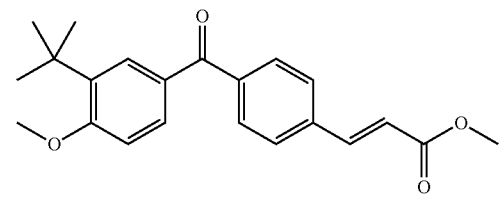 [SMILES: COC(=O)/C=C/c1ccc(C(=O)c2ccc(OC)c(C(C)(C)C)c2)cc1]

Methyl (2E)-3-{4-[(3-tert-butyl-4-methoxyphenyl)carbonyl]phenyl}prop-2-enoate was prepared according example 42(e), starting from 600 mg of (3-tert-butyl-4-methoxyphenyl)(4-iodophenyl) methanone. Purification of the crude by silica gel chromatography using the following gradient system, (cyclohexane/dichloromethane): (20/80) to (0/100), afforded title compound as a white solid (410 mg, 76%). mp=128-129° C. ¹H NMR (400 MHz, CHLOROFORM-d) δ ppm 1.39 (s, 9H), 3.83 (s, 3H), 3.93 (s, 3H), 6.54 (d, J=16.06 Hz, 1H), 6.91 (d, J=8.53 Hz, 1H), 7.57-7.69 (m, 3H), 7.71-7.81 (m, 3H), 7.87 (d, J=2.01 Hz, 1H).

Example 58: (2E)-3-{4-[(3-tert-butyl-4-methoxyphenyl)carbonyl]phenyl}prop-2-enoic Acid

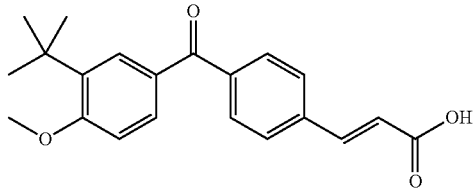 [SMILES: COc1ccc(C(=O)c2ccc(/C=C/C(=O)O)cc2)cc1C(C)(C)C]

(2E)-3-{4-[(3-tert-butyl-4-methoxyphenyl)carbonyl]phenyl}prop-2-enoic acid was prepared according to example 3 using 30 mg of methyl (2E)-3-{4-[(3-tert-butyl-4-methoxyphenyl)carbonyl]phenyl}prop-2-enoate. A white solid is obtained (28 mg, 90%). mp=237-238° C. $^1$H NMR (400 MHz, DMSO-$d_6$) δ ppm 1.38 (s, 9H), 3.94 (s, 3H), 6.69 (d, J=15.94 Hz, 1H), 7.16 (d, J=8.66 Hz, 1H), 7.58-7.82 (m, 5H), 7.88 (d, J=8.16 Hz, 2H), 12.59 (s, 1H). HRMS (TOF MS ES−) for C21H21O4− (M−H)− calcd. 337.1440, found 337.1436.

Example 59: Methyl (2E)-3-{4-[2-(3-tert-butyl-4-methoxyphenyl)-1,3-dioxolan-2-yl]phenyl}prop-2-enoate

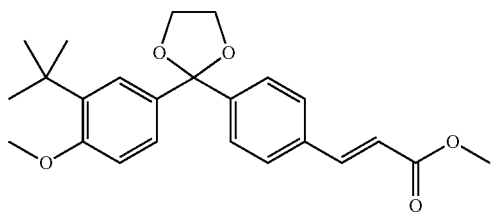 [SMILES: COC(=O)/C=C/c1ccc(C2(c3ccc(OC)c(C(C)(C)C)c3)OCCO2)cc1]

Methyl (2E)-3-{4-[2-(3-tert-butyl-4-methoxyphenyl)-1,3-dioxolan-2-yl]phenyl}prop-2-enoate was prepared according example 42(b), starting from 660 mg methyl (2E)-3-{4-[(3-tert-butyl-4-methoxyphenyl)carbonyl]phenyl}prop-2-enoate. Purification of the crude by silica, gel chromatography using the following gradient system, (cyclohexane/ethyl acetate): (93/7) to (65/35), afforded the title compound as a white solid (490 mg, 65%). mp=132-133° C. $^1$H NMR (400 MHz, CHLOROFORM-d) δ ppm 1.34 (s, 9H), 3.74-3.84 (m, 6H), 3.95-4.14 (m, 4H), 6.42 (d, J=16.00 Hz, 1H), 6.79 (d, J=8.53 Hz, 1H), 7.20-7.25 (m, 1H), 7.39-7.44 (m, 1H), 7.45-7.58 (m, 4H), 7.68 (d, J=16.00 Hz, 1H).

Example 60: Methyl 3-{4-[2-(3-tert-butyl-4-methoxyphenyl)-1,3-dioxolan-2-yl]phenyl}propanoate

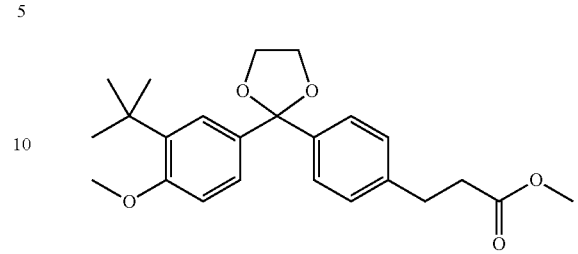

Methyl 3-{4-[2-(3-tert-butyl-4-methoxyphenyl)-1,3-dioxolan-2-yl]phenyl}propanoate was prepared according to example 38, starting from 250 mg of methyl (2E)-3-{4-[2-(3-tert-butyl-4-methoxyphenyl)-1,3-dioxolan-2-yl]phenyl}prop-2-enoate. Purification of the crude by silica gel chromatography using the following gradient system, (cyclohexane/ethyl acetate): (93/7) to (60/40), afforded the title compound as a colorless oil (210 mg, 81%). $^1$H NMR (400 MHz, CHLOROFORM-d) δ ppm 1.34 (s, 9H), 2.61 (t, J=7.91 Hz, 2H), 2.87 (t, J=7.91 Hz, 2H), 3.66 (s, 3H), 3.80 (s, 3H), 6.78 (d, J=8.44 Hz, 1H), 7.15 (d, J=8.03 Hz, 2H), 7.23 (dd, J=8.44, 2.20 Hz, 1H), 7.36-7.47 (m, 3H).

Example 61: 3-{4-[2-(3-tert-butyl-4-methoxyphenyl)-1,3-dioxolan-2-yl]phenyl}propanoic Acid

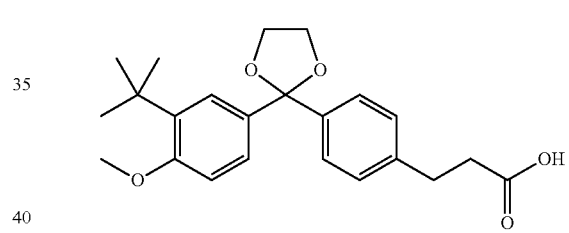

3-{4-[2-(3-tert-butyl-4-methoxyphenyl)-1,3-dioxolan-2-yl]phenyl}propanoic acid was prepared according to example 3 starting from 158 mg of methyl 3-{4-[2-(3-tert-butyl-4-methoxyphenyl)-1,3-dioxolan-2-yl]phenyl}propanoate. A white solid is obtained (148 mg, 97%). mp=121° C. NMR (400 MHz, CHLOROFORM-d) δ ppm 1.34 (s, 9H), 2.66 (t, J=7.78 Hz, 2H), 2.91 (t, J=7.78 Hz, 2H), 3.80 (s, 3H), 3.94-4.13 (m, 4H), 6.79 (d, J=8.44 Hz, 1H), 7.17 (d, J=7.91 Hz, 2H), 7.23 (dd, J=8.44, 1.69 Hz, 1H), 7.38-7.47 (m, 3H). HRMS (TOF MS ES−) for C23H27O5− (M−H)− calcd. 383.1858, found 383.1864.

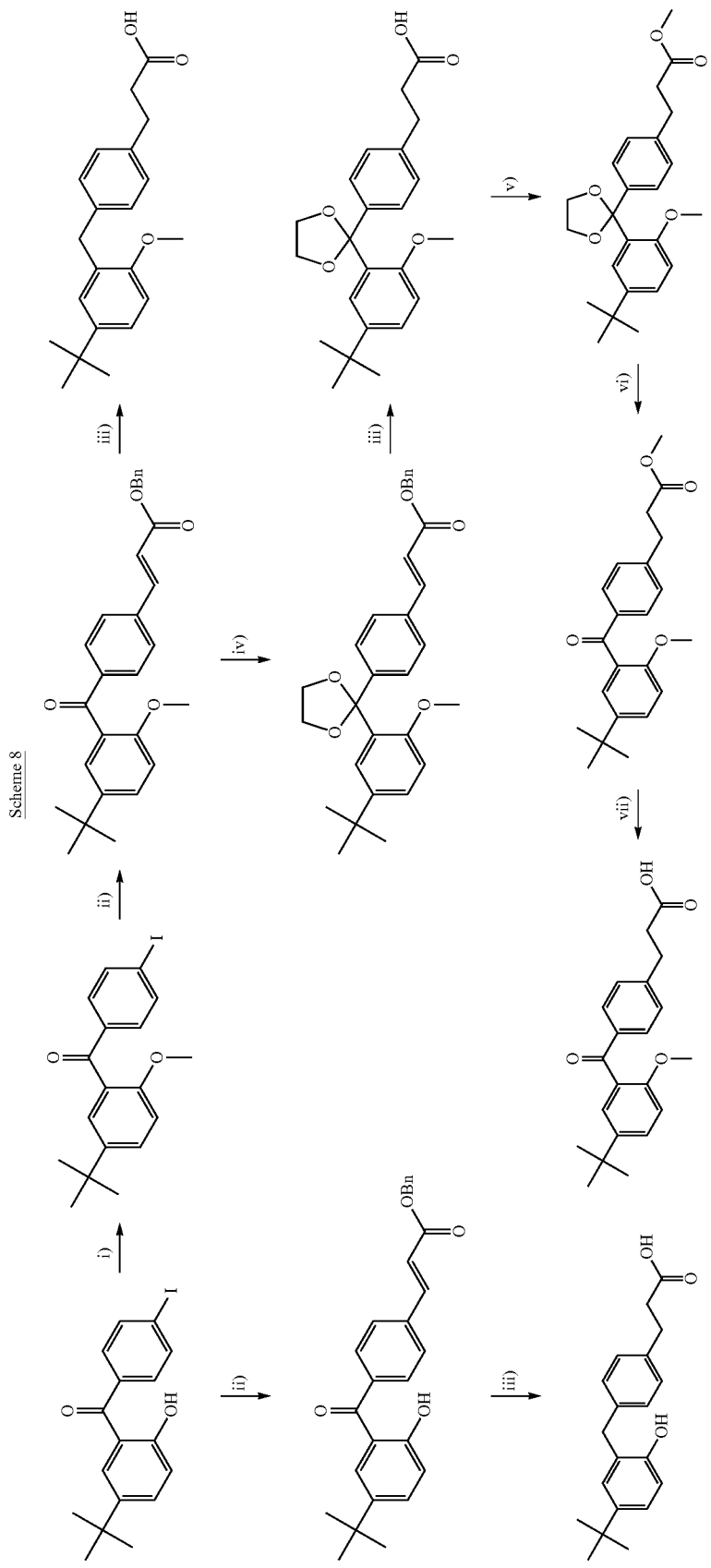
Scheme 8
i) 1) NaH, DMF; 2) CH₃I; ii) benzyl acrylate, Pd(OAc)₂, NEt₃, DMF, 100° C. 3 h; iii) H₂, Pd/C, EtOH, EtOAc, MeOH, 20 psi, overnight;
iv) ethylene glycol, pTsOH, toluene, reflux; v) EDC, DMAP, MeOH, DCM 3 h, r.t.; vi) I₂, acetone, MS 4Å, reflux, 14 h ; vii) LiOH 1N, THF, r.t. overnight.

Example 62: Benzyl 3-[4-(5-tert-butyl-2-methoxybenzoyl)phenyl]propanoate

(a) (5-tert-butyl-2-methoxyphenyl)(4-iodophenyl)methanone

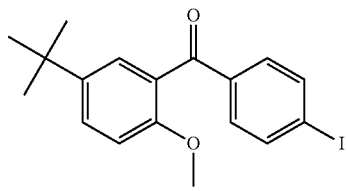 [SMILES: COc1ccc(C(C)(C)C)cc1C(=O)c1ccc(I)cc1]

(5-tert-butyl-2-methoxyphenyl)(4-iodophenyl)methanone was prepared according to example 55(a) starting with 510 mg of 4-tert-butyl-2-[(4-iodophenyl)carbonyl]phenol. Purification of the crude by silica gel chromatography using the following gradient system, (cyclohexane/dichloromethane): (88/12) to (0/100), afforded the title compound as a colorless oil (515 mg, 97%). $^1$H NMR (400 MHz, CHLOROFORM-d) δ ppm 1.31 (s, 9H), 3.69 (s, 3H), 6.91 (d, J=8.78 Hz, 1H), 7.37 (d, J=2.38 Hz, 1H), 7.46-7.55 (m, 3H), 7.79 (d, J=8.41 Hz, 2H).

(b) Benzyl 3-[4-(5-tert-butyl-2-methoxybenzoyl)phenyl]propanoate

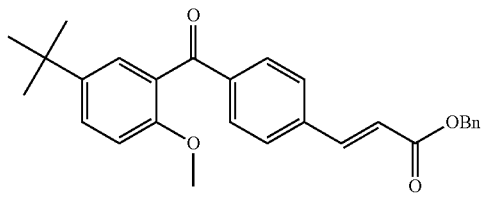 [SMILES: COc1ccc(C(C)(C)C)cc1C(=O)c1ccc(/C=C/C(=O)OCc2ccccc2)cc1]

(3E)-4-{4-[(5-tert-butyl-2-methoxyphenyl)carbonyl]phenyl}but-3-en-2-one was prepared according to example 42(e) starting from 530 mg of (5-tert-butyl-2-methoxyphenyl)(4-iodophenyl)methanone. Purification of the crude by silica gel chromatography using the following gradient system, (cyclohexane/ethyl acetate): (95/5) to (60/40), afforded the title compound as a colorless oil (771 mg, 71%). $^1$H NMR (400 MHz, CHLOROFORM-d) δ ppm 1.31 (s, 9H), 3.68 (s, 3H), 6.57 (d, J=16.06 Hz, 1H), 6.92 (d, J=8.75 Hz, 1H), 7.31-7.46 (m, 6H), 7.50 (dd, J=8.75, 2.57 Hz, 1H), 7.57 (m, J=8.28 Hz, 2H), 7.75 (d, J=16.06 Hz, 1H), 7.82 (m, J=8.28 Hz, 2H).

Example 63: 3-{4-[(5-tert-butyl-2-methoxyphenyl)methyl]phenyl}propanoic Acid

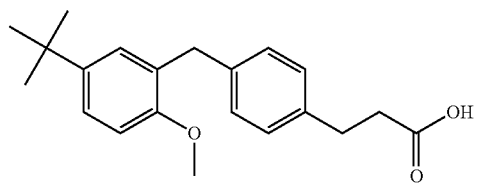 [SMILES: COc1ccc(C(C)(C)C)cc1Cc1ccc(CCC(=O)O)cc1]

3-{4-[(5-tert-butyl-2-methoxyphenyl)methyl]phenyl}propanoic acid was prepared according to example 38 using 235 mg of (3E)-4-{4-[(5-tert-butyl-2-ethoxyphenyl)carbonyl]phenyl}but-3-en-2-one. A white solid is obtained (120 mg, 67%). mp=97-98° C. $^1$H NMR (400 MHz, CHLOROFORM-d) δ ppm 1.20-1.36 (m, 9H), 2.65 (t, J=7.78 Hz, 2H), 2.91 (t, J=7.78 Hz, 2H), 3.77 (s, 3H), 3.93 (s, 2H), 6.79 (d, J=8.50 Hz, 1H), 7.05-7.18 (m, 5H), 7.20 (dd, J=8.50, 2.45 Hz, 1H). HRMS (TOF MS ES-) for C21H25O3- (M-H)- calcd. 325.1804, found 325.1794.

Example 64: Benzyl (2E)-3-[4-(5-tert-butyl-2-hydroxybenzoyl)phenyl]prop-2-enoate

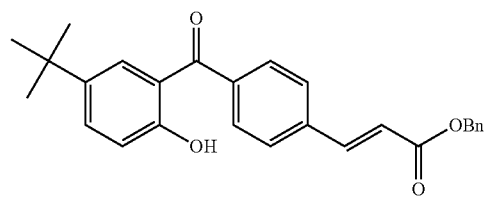 [SMILES: CC(C)(C)c1ccc(O)c(C(=O)c2ccc(/C=C/C(=O)OCc3ccccc3)cc2)c1]

(3E)-4-{4-[(5-tert-butyl-2-hydroxyphenyl)carbonyl]phenyl}but-3-en-2-one was prepared according to example 42(c) starting from 515 mg of 4-tert-butyl-2-[(4-iodophenyl)carbonyl]phenol. Purification of the crude by silica gel chromatography using the following gradient system, (cyclohexane/dichloromethane): (80/20) to (0/100), afforded the title compound as a yellow solid (445 mg, 88%). mp=111° C. $^1$H NMR (400 MHz, CHLOROFORM-d) δ ppm 1.25 (s, 9H), 5.28 (s, 2H), 6.61 (d, J=16.06 Hz, 1H), 7.03 (d, J=8.72 Hz, 1H), 7.32-7.46 (m, 5H), 7.54 (d, J=2.26 Hz, 1H), 7.58 (dd, J=8.72, 2.38 Hz, 1H), 7.63-7.75 (m, 5H), 7.79 (d, J=16.06 Hz, 1H), 11.75 (s, 1H).

Example 65: 3-{4-[(5-tert-butyl-2-hydroxyphenyl)methyl]phenyl}propanoic Acid

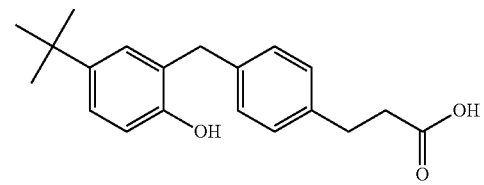 [SMILES: CC(C)(C)c1ccc(O)c(Cc2ccc(CCC(=O)O)cc2)c1]

3-{4-[(5-tert-butyl-2-hydroxyphenyl)methyl]phenyl}propanoic acid was prepared according to example 38 starting from 143 mg of benzyl (2E)-3-[4-(5-tert-butyl-2-hydroxybenzoyl)phenyl]prop-2-enoate. Purification of the crude by silica gel chromatography using the following gradient system, (dichloromethane/methanol): (98/2) to (80/20), afforded the title compound as a white solid (77 mg, 72%). mp=98-99° C. $^1$H NMR (400 MHz, CHLOROFORM-d) δ ppm 1.28 (s, 9H), 2.65 (t, J=7.78 Hz, 2H), 2.92 (t, J=7.78 Hz, 2H), 3.96 (s, 2H), 6.71 (d, J=9.03 Hz, 1H), 7.04-7.22 (m, 6H).

Example 66: Benzyl (2E)-3-{4-[2-(5-tert-butyl-2-methoxyphenyl)-1,3-dioxolan-2-yl]phenyl}prop-2-enoate

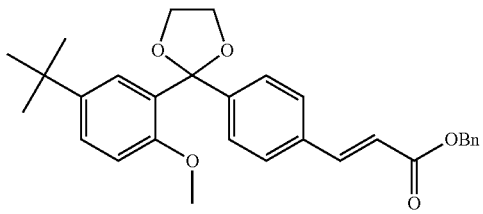 [SMILES: COc1ccc(C(C)(C)C)cc1C1(c2ccc(/C=C/C(=O)OCc3ccccc3)cc2)OCCO1]

(3E)-4-{4-[2-(5-tert-butyl-2-methoxyphenyl)-1,3-dioxolan-2-yl]phenyl}but-3-en-2-one was prepared according to example 42(b), starting from 350 mg of (b) Benzyl 3-[4-(5-tert-butyl-2-methoxybenzoyl)phenyl]propanoate. Purification of the crude by silica gel chromatography using the following gradient system, (cyclohexane/ethyl acetate): (95/5) to (70/30), afforded the title compound as a white solid (230 mg, 60%). mp=100-101° C. $^1$H NMR (400 MHz, CHLOROFORM-d) δ ppm 1.34 (s, 9H), 3.54 (s, 3H), 4.09 (s, 4H), 5.24 (s, 2H), 6.45 (d, J=16.06 Hz, 1H), 6.77 (d, J=8.53 Hz, 1H), 7.28-7.53 (m, 10H), 7.70 (d, J=16.06 Hz, 1H), 7.79 (d, J=2.26 Hz, 1H).

Example 67: Methyl 3-{4-[(5-tert-butyl-2-methoxyphenyl)carbonyl]phenyl}propanoate

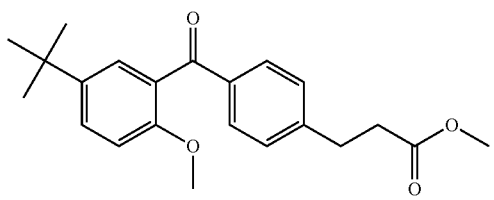 [SMILES: COC(=O)CCc1ccc(C(=O)c2cc(C(C)(C)C)ccc2OC)cc1]

3-{4-[2-(5-tert-butyl-2-methoxyphenyl)-1,3-dioxolan-2-yl]phenyl}propanoic acid was prepared according to example 38 starting from 166 mg of (3E)-4-{4-[2-(5-tert-butyl-2-methoxyphenyl)-1,3-dioxolan-2-yl]phenyl}but-3-en-2-one. 3-{4-[2-(5-tert-butyl-2-methoxyphenyl)-1,3-dioxolan-2-yl]phenyl}propanoic acid was obtained as a mixture with 3-{4-[(5-tert-butyl-2-methoxyphenyl)methyl]phenyl}propanoic acid (25%). It was used in the following reaction without any further purification.

To solution of the previous carboxylic acids mixture (175 mg 0.46 mmol regarding the highest MW, 1 eq.) in DCM (4 mL), were added methanol (100, 1.12 mmol, 6.8 eq.) and EDC.Cl (105 mg, 0.55 mmol, 1.2 mmol). After stirring 3 hours, the mixture was diluted in DCM (50 mL) and washed with aqueous sat.NaHCO$_3$ (2×30 mL) and water (2×30 mL). The organic layer was dried over Ca$_2$SO$_4$ and concentrated. Purification of the crude by silica gel chromatography using the following gradient system, (cyclohexane/ethyl acetate): (93/7) to (40/60), afforded methyl 3-{4-[2-(5-tert-butyl-2-methoxyphenyl)-1,3-dioxolan-2-yl]phenyl}propanoate as a mixture with methyl 3-{4-[(5-tert-butyl-2-methoxy-phenyl)methyl]phenyl}propanoate. It was used in the following step without any further purification.

Title compound was obtained according to example 3, starting from 64 mg of the previously obtained mixture. Purification of the crude by silica gel chromatography using the following gradient system, (cyclohexane/ethyl acetate): (100/0) to (60/40), afforded the title compound as a brown oil (32 mg). $^1$H NMR (400 MHz, CHLOROFORM-d) δ ppm 1.30 (s, 9H), 2.66 (d, J=7.78 Hz, 2H), 3.01 (t, J=7.68 Hz, 2H), 3.70 (s, 3H), 3.67 (s, 3H), 6.92 (d, J=8.72 Hz, 1H), 7.26 (d, J=8.09 Hz, 2H) 7.34 (d, J=2.30 Hz, 1H) 7.47 (dd, J=8.72, 2.30 Hz, 1H) 7.76 (d, J=8.09 Hz, 2H). HRMS (TOF MS ES−) for C20H23O3− (M−H)− calcd. 311.1647, found 311.1658.

Example 68: 3-{4[(5-tert-butyl-2-methoxyphenyl)carbonyl]phenyl}propanoic Acid

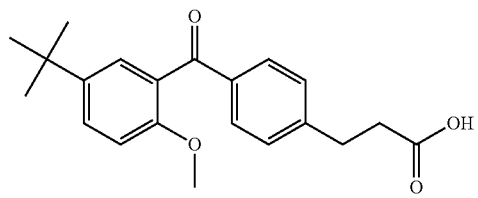 [SMILES: COc1ccc(C(C)(C)C)cc1C(=O)c1ccc(CCC(=O)O)cc1]

3-{4-[(5-tert-butyl-2-methoxyphenyl)carbonyl]phenyl}propanoic acid was prepared according to example 3, starting from 30 mg of methyl 3-{4-[(5-tert-butyl-2-methoxyphenyl)carbonyl]phenyl}propanoate. A yellow oil was obtained (28 mg, 98%). $^1$H NMR (400 MHz, CHLOROFORM-d) δ ppm 1.25-1.38 (m, 9H), 2.71 (t, J=7.72 Hz, 2H), 3.02 (t, J=7.72 Hz, 2H), 3.70 (s, 3H), 6.92 (d, J=8.785 Hz, 1H), 7.23-7.30 (m, 2H), 7.35 (d, J=2.42 Hz, 1H), 7.47 (dd, J=8.75, 2.42 Hz, 1H), 7.77 (d, J=8.16 Hz, 2H). HRMS (TOF MS ES−) for C21H23O4− (M−H)− calcd. 339.1596, found 339.1611.

Example 69: methyl (2E)-3-{4-[5-(adamantan-1-yl)-2-methoxybenzoyl]phenyl}prop-2-enoate (a) 4-(Adamantan-1-yl)phenol Phenol (1.88 g, 0.02 mol) and 3.04 g (0.02 mol) of 1-adamantanol were dissolved in 10 mL of dichloromethane. To the resulting solution was slowly added 1.1 mL (0.02 mol) of concentrated sulfuric acid (98%). The mixture was stirred overnight at room temperature, poured into water, neutralized with sodium bicarbonate, extracted with EtOAc, dried over MgSO$_4$, and evaporated. Recrystallization from cyclohexane provided 2.5 g (55%) of a white solid; M. p. 181-182° C. $^1$H NMR (400 MHz, DMSO) δ 9.08 (s, 1H), 7.12 (d, J=8.6 Hz, 2H), 6.67 (d, J=8.6 Hz, 2H), 2.02 (s, 3H), 1.80 (s, 3H), 1.79 (s, 3H), 1.70 (s, 6H). $^{13}$C NMR (101 MHz, DMSO) δ 154.93, 141.27, 125.37, 114.67, 42.91, 36.22, 34.91, 28.35. HRMS (TOF MS ES−) for C16H19O− (M−H−) calcd. 227.1436, found 227.1433.

(b) 1-(4-Methoxyphenyl)adamantane

To a suspension of sodium hydride (60% in oil, 0.46 g, 10 mmol) in 10 mL of DMF was slowly added, while maintaining the temperature at 20° C., 2.28 g (10 mmol) of 69 (a). The mixture was stirred for 1 h at room temperature at which point CH3I (0.68 mL, 11 mmol) was added. The mixture was then stirred for 2 h at 20° C., poured into water, and extracted with Et$_2$O. After standard work-up followed by chromatography (cyclohexane), 1.426 g (59%) of 29 as a white solid was obtained. M. p. 76-77° C.; Rf=0.34 (5% EtOAc:cyclohexane), $^1$H NMR (400 MHz, CDCl3) δ 7.28 (d, J=8.9 Hz, 1H), 6.86 (d, J=8.9 Hz, 1H), 3.79 (s, 3H), 2.08 (s, 3H), 1.89 (s, 3H), 1.88 (s, 3H), 1.81-1.69 (m, 6H). $^{13}$C NMR (101 MHz, CDCl3) δ 157.32, 143.70, 125.76, 113.38, 55.19, 43.38, 36.79, 35.53, 28.99.

(c) [5-(Adamantan-1-yl)-2-methoxyphenyl](4-iodophenyl)methanone

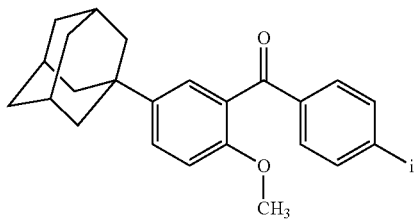

Compound was prepared according to the procedure described by Boehm et al. (J. Med. Chem. 1994, 37, 2930-2941) from example 69 (b). After work-up, the crude product was purified by chromatography to yield 69 (c) as a yellow oil, 1.50 g (28%). Rf=0.60 (5% EtOAc:cyclohexane). $^1$H NMR (400 MHz, CDCl$_3$) δ 7.78 (d, J=8.4 Hz, 2H), 7.52 (d, J=8.4 Hz, 2H), 7.46 (dd, J=8.7, 2.4 Hz, 1H), 7.35 (d, J=2.4 Hz, 1H), 6.93 (d, J=8.7 Hz, 1H), 3.69 (s, 3H), 2.08 (s, 3H), 1.89 (s, 6H), 1.75 (q, J=12.1 Hz, 6H). $^{13}$C NMR (101 MHz, CDCl3) δ 196.26, 155.35, 143.94, 137.57, 131.35, 128.86, 127.72, 126.51, 111.30, 100.84, 55.77, 43.36, 36.79, 35.80, 29.01. HRMS (TOF MS ES+) for C24H26IO2+ (MH+) calcd. 473.0978, found 473.0981.

(d) Methyl (2E)-3-{4-[5-(adamantan-1-yl)-2-methoxybenzoyl]phenyl}prop-2-enoate

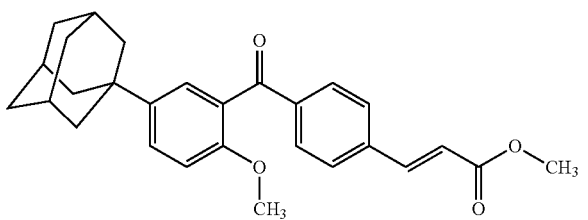 [SMILES: COC(=O)/C=C/c1ccc(C(=O)c2cc(C34CC5CC(CC(C5)C3)C4)ccc2OC)cc1]

To a stirred solution of example 69 (c) (1.24 g, 2.63 mmol) and Et$_3$N (1098 uL, 7.89 mmol) was added 357 uL (3.94 mmol) of methyl acrylate. Palladium (II) acetate (12 mg) and (2-Tol)3P (64 mg) was added and heated at 100° C. for 3 hrs. The reaction mixture was allowed to cool to rt, concentrated under reduced pressure and purified by chromatography to yield a yellow solid, 0.59 g (52%). M. p. 135.5-137° C.; Rf=0.40 (15% EtOAc:cyclohexane). $^1$H NMR (400 MHz, CDCl3) δ 7.82 (d, J=8.2 Hz, 2H), 7.72 (d, J=16.0 Hz, 1H), 7.57 (d, J=8.2 Hz, 2H), 7.47 (dd, J=8.7, 2.4 Hz, 1H), 7.36 (d, J=2.3 Hz, 1H), 6.94 (d, J=8.7 Hz, 1H), 6.52 (d, J=16.0 Hz, 1H), 3.82 (s, 3H), 3.69 (s, 3H), 2.09 (s, 3H), 1.90 (s, 6H), 1.77 (s, 3H), 1.74 (s, 3H). $^{13}$C NMR (101 MHz, CDCl3) δ 196.27, 167.17, 155.42, 143.99, 143.81, 139.40, 138.43, 130.45, 128.84, 128.06, 127.93, 126.54, 120.15, 111.35, 55.81, 52.00, 43.40, 36.83, 35.85, 29.05. HRMS (TOF MS ES+) for C28H31O4+ (MH+) calcd. 431.2222, found 431:2227.

Example 70: Methyl (2E)-3-(4-{2-[5-(adamantan-1-yl)-2-methoxyphenyl]-1,3-dioxolan-2-yl}phenyl)prop-2-enoate

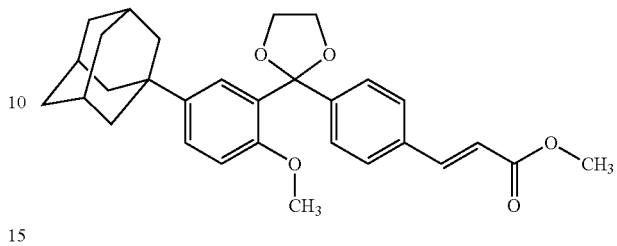

Example 69 (200 mg, 0.46 mmol) was treated with ethylene glycol (2 mL) and a catalytic amount of pTsOH (20 mg) in toluene (10 mL) at 145° C. overnight using a Dean Stark trap according to a modified procedure of Dawson et al. 8 After cooling to rt, it was washed with saturated NaHCO$_3$ (aq.), brine, dried over MgSO$_4$ and concentrated under reduced pressure. The residue was purified using Biotage to yield a white solid, 112 mg (64%, 40 mg of starting material recovered). M.p. 163-165° C.; Rf=0.34 (15% EtOAc:cyclohexane). $^1$H NMR (400 MHz, CDCl3) δ 7.77 (d, J=2.5 Hz, 1H), 7.67 (d, J=16.0 Hz, 1H), 7.49 (d, J=8.3 Hz, 2H), 7.44 (d, J=8.4 Hz, 2H), 7.28 (d, J=8.5, 2.5 Hz, 1H), 6.79 (d, J=8.6 Hz, 1H), 6.40 (d, J=16.0 Hz, 1H), 4.09 (s, 4H), 3.79 (s, 3H), 3.55 (s, 3H), 2.11 (s, 3H), 1.94 (s, 3H), 1.93 (s, 3H), 1.78 (s, 6H). $^{13}$C NMR (101 MHz, CDCl3) δ 167.65, 154.99, 145.17, 144.88, 143.45, 133.70, 129.04, 127.58, 126.82, 126.21, 123.25, 117.69, 112.28, 108.96, 65.28, 56.05, 51.80, 43.58, 36.96, 35.88, 29.18. HRMS (TOF MS ES+) for C30H35O5+ (MH+) calcd. 475.2484, found 475.2484.

Example 71: (2E)-3-(4-{2-[5-(adamantan-1-yl)-2-methoxyphenyl]-1,3-dioxolan-2-yl}phenyl)prop-2-enoic Acid

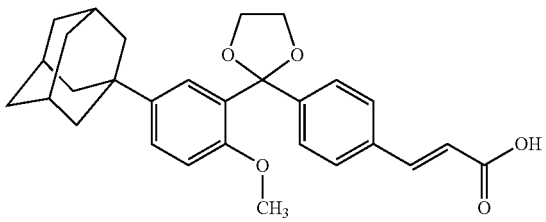 [SMILES: COc1ccc(C23CC4CC(CC(C4)C2)C3)cc1C1(c2ccc(/C=C/C(=O)O)cc2)OCCO1]

To a solution of the example 70 (140 mg, 0.29 mmol) in anhydrous THF (5 mL) was added aqueous LiOH (1.0 mL, 1.0 N) dropwise. The reaction mixture was stirred at 75° C. for 3 hrs. The reaction was then cooled (0° C.), acidified to pH 2 with 1.0 N HCl, and extracted with EtOAc (3×15 mL). The combined organic phases were dried (anhydrous Na2SO4) and concentrated in vacuo to afford a thick colorless oil. The resultant oil was purified on a 30 g Biotage ZIP cartridge and eluted with 0-60% EtOAc:cyclo-hexane+ 0.1% HOAc gradient to provide a white solid (129 mg, 96%). M.p. 238-240° C.; Rf=0.40 (60% EtOAc:cyclohexane+0.1% HOAc), $^1$H NMR (400 MHz, CDCl3) δ 7.78 (d, J=2.5 Hz, 1H), 7.76 (d, J=16.2 Hz, 1H), 7.51 (d, J=8.3 Hz, 2H), 7.47 (d, J=8.4 Hz, 2H), 7.28 (dd, J=8.6, 2.5 Hz, 1H), 6.79 (d, J=8.6 Hz, 1H), 6.41 (d, J=15.9 Hz, 1H), 4.10

(s, 4H), 3.55 (s, 3H), 2.11 (s, 3H), 1.94 (s, 3H), 1.94 (s, 3H), 1.78 (s, 6H). $^{13}$C NMR (101 MHz, CDCl3) δ 171.86, 154.97, 147.06, 145.66, 143.46, 133.36, 128.97, 127.88, 126.90, 126.26, 123.24, 117.02, 112.27, 108.93, 65.29, 56.03, 43.58, 36.96, 35.89, 29.18. HRMS (TOF MS ES+) for C29H35O5+ (MH+) calcd. 463.2484, found 463.2484.

Example 72: 3-(4-{2-[5-(adamantan-1-yl)-2-methoxyphenyl]-1,3-dioxolan-2-yl}phenyl)propanoic Acid

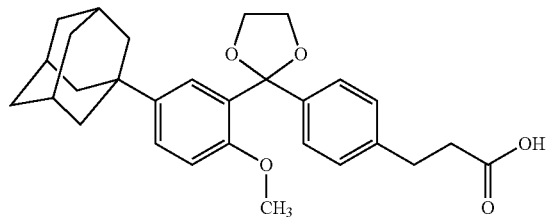

Example 71 was hydrogenated according to the general procedure for the formation of example 38 to provide a white solid 93 mg (86%) after chromatography; m. p. 173-175° C. $^1$H NMR (400 MHz, CDCl3) δ 7.76 (d, J=2.5 Hz, 1H), 7.39 (d, J=8.2 Hz, 2H), 7.26 (d, J=8.5, 2.5 Hz, 1H), 7.11 (d, J=8.2 Hz, 2H), 6.79 (d, J=8.6 Hz, 1H), 4.08 (ddd, J=6.3, 3.4, 1.9 Hz, 4H), 3.54 (s, 3H), 2.92 (t, J=7.8 Hz, 2H), 2.64 (t, J=7.8 Hz, 2H), 2.10 (s, 3H), 1.93 (s, 3H), 1.93 (s, 3H), 1.78 (s, 6H). $^{13}$C NMR (101 MHz, CDCl3) δ 178.29, 155.12, 143.33, 140.85, 139.49, 129.51, 127.60, 126.46, 125.94, 123.37, 112.40, 109.26, 65.17, 56.12, 43.57, 36.97, 35.86, 35.56, 30.46, 29.18. HRMS (TOF MS ES+) for C29H35O5+ (MH+) calcd. 463.2484, found 463.2484.

Example 73: Methyl 3-(4-{2-[5-(adamantan-1-yl)-2-methoxyphenyl]-1,3-dioxolan-2-yl}phenyl)propanoate

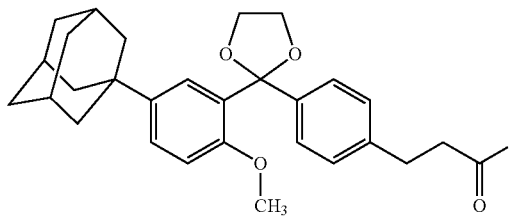

Example 73 was prepared from example 70 by hydrogenation under Pd—C catalysis using the general procedure (example 38) to provide a white solid, 260 mg (85%). M. p. 112-113° C.; R$_f$=0.45 (15% EtOAc:cyclohexane). $^1$H NMR (400 MHz, CDCl$_3$) δ 7.76 (d, J=2.5 Hz, 1H), 7.38 (d, J=8.2 Hz, 2H), 7.26 (dd, J=8.5, 2.6 Hz, 1H), 7.10 (d, J=8.2 Hz, 2H), 6.79 (d, J=8.6 Hz, 1H), 4.17-3.99 (m, 4H), 3.65 (s, 3H), 3.55 (s, 3H), 2.91 (t, J=7.9 Hz, 2H), 2.59 (t, J=7.9 Hz, 2H), 2.10 (s, 3H), 1.93 (s, 3H), 1.93 (s, 3H), 1.86-1.69 (m, 6H). $^{13}$C NMR (101 MHz, CDCl$_2$) δ 173.51, 155.12, 143.32, 140.71, 139.83, 129.52, 127.60, 126.40, 125.92, 123.37, 112.38, 109.27, 65.16, 56.13, 51.71, 43.56, 36.96, 35.85, 35.81, 30.78, 29.17. HRMS (TOF MS ES+) for C$_{30}$H$_{37}$O$_5^+$ (MH+) calcd. 477.2641, found 477.2643.

Example 74: Methyl 3-{4-[3-(adamantan-1-yl)-2-methoxybenzoyl]phenyl}propanoate

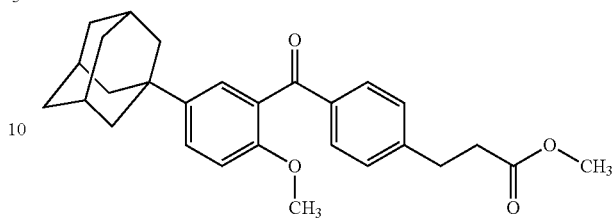

A mixture of example 73 (146 mg, 0.31 mmol) and iodine (100 mg, 0.39 mmol) in acetone (6 mL, reagent ACS, 0.2% H$_2$O) was stirred for 3 hrs under reflux according to the reported method for example 45. After work-up and purification on a Biotage 45 g ZIP cartridge using 0-15% EtOAc:cyclohexane gradient, a brown oil (120 mg, 91%) was obtained; R$_f$=0.40 (15% EtOAc:cyclohexane). $^1$H NMR (400 MHz, CDCl$_3$) δ 7.76 (d, J=8.2 Hz, 2H), 7.44 (dd, J=8.7, 2.4 Hz, 1H), 7.32 (d, J=2.4 Hz, 1H), 7.26 (d, J=8.0 Hz, 2H), 6.93 (d, J=8.7 Hz, 1H), 3.70 (s, 3H), 3.67 (s, 3H), 3.01 (t, J=7.7 Hz, 2H), 2.66 (t, J=7.7 Hz, 2H), 2.08 (s, 3H), 1.89 (s, 3H), 1.88 (s, 3H), 1.75 (q, J=12.1 Hz, 6H). $^{13}$C NMR (101 MHz, CDCl$_3$) δ 196.63, 173.15, 155.24, 146.03, 143.77, 136.33, 130.46, 128.55, 128.30, 128.25, 126.26, 111.30, 55.87, 51.85, 43.39, 36.84, 35.81, 35.29, 31.07, 29.05. HRMS (TOF MS ES+) for C$_{28}$H$_{33}$O$_4^+$ (MH+) calcd. 433.2379, found 433.2381.

Example 75: Methyl 3-(4-{2-[5-(adamantan-1-yl)-2-methoxyphenyl]-1,3-dithiolan-2-yl}phenyl)propanoate

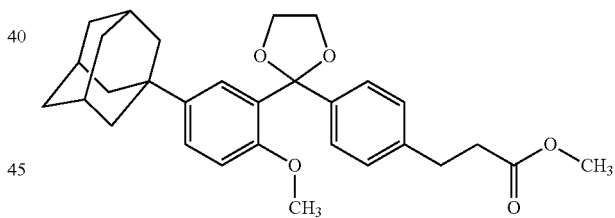

Prepared according to the reported procedure for example 48. To a solution of the keto ester (117 mg, 0.27 mmol) in CR$_2$Cl$_2$ (5 mL) at rt under argon was added a solution of the (CH$_2$SH)$_2$ (35 μL, 0.41 mmol) followed by BF$_3$.Et$_2$0 (52 μL, 0.41 mmol). The resulting mixture was stirred at rt overnight. The reaction was quenched by pouring the mixture into saturated NaHCO$_3$, and the mixture was extracted with 20 mL CH$_2$Cl$_2$. The combined organic layers were dried (MgSO$_4$) and concentrated to afford a solid. Flash chromatography (15% CH$_2$Cl$_2$:cyclohexane) yielded a yellow solid, 106 mg (77%). M. p. 127-1.28° C.; R$_f$=0.50 (15% EtOAc:cyclohexane). $^1$H NMR (400 MHz, CDCl3) δ 8.11 (d, J=2.3 Hz, 1H), 7.39 (d, J=8.2 Hz, 2H), 7.25 (dd, J=8.3, 2.4 Hz, 1H), 7.02 (d, J=8.1 Hz, 2H), 6.79 (d, J=8.5 Hz, 1H), 3.65 (s, 3H), 3.50 (s, 3H), 3.44 (dt, J=10.0, 7.5 Hz, 2H), 3.31 (dt, J=11.8, 7.2 Hz, 2H), 2.89 (t, J=7.9 Hz, 2H), 2.58 (t, J=7.9 Hz, 2H), 2.12 (s, 3H), 1.96 (s, 3H), 1.96 (s, 3H), 1.79 (s, 6H). $^{13}$C NMR (101 MHz, CDCl$_3$) δ 173.55, 154.68, 143.39, 143.34, 138.73, 133.36, 127.59, 127.03, 125.03, 123.78, 112.49, 74.73, 55.88, 51.71, 43.64, 40.41, 36.98, 36.05, 35.71, 30.61, 29.20. HRMS (TOF MS ES+) for $C_{30}H_{37}O_3S_2^+$ (MH+) calcd. 509.2184, found 509.2184.

Example 76: 3-(4-{2-[5-(adamantan-1-yl)-2-methoxyphenyl]-1,3-dithiolan-2-yl}phenyl)propanoic Acid

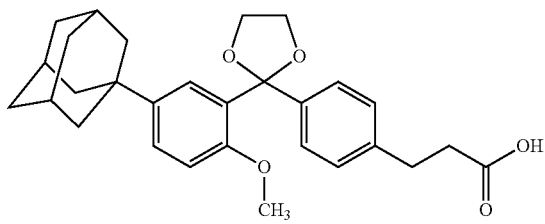 [SMILES: COc1ccc(C23CC4CC(CC(C4)C2)C3)cc1C1(c2ccc(CCC(=O)O)cc2)OCCO1]

Example 75 was hydrolyzed according to example 3 to yield a white solid, 49 mg (55%). $^1$H NMR (400 MHz, CDCl$_3$) δ 8.11 (d, J=2.4 Hz, 1H), 7.40 (d, J=8.2 Hz, 2H), 7.25 (dd, J=8.3, 2.4 Hz, 1H), 7.03 (d, J=8.2 Hz, 2H), 6.79 (d, J=8.5 Hz, 1H), 3.50 (s, 3H), 3.48-3.39 (m, 2H), 3.36-3.26 (m, 2H), 2.90 (t, J=7.8 Hz, 2H), 2.63 (t, J=7.8 Hz, 2H), 2.12 (s, 3H), 1.96 (s, 3H), 1.96 (s, 3H), 1.85-1.71 (m, 6H). $^{13}$C NMR (101 MHz, CDCl$_3$) δ 178.06, 154.68, 143.54, 143.34, 138.38, 133.35, 127.59, 127.08, 125.05, 123.77, 112.50, 74.71, 55.89, 43.65, 40.42, 36.98, 36.05, 35.40, 30.27, 29.20. HRMS (TOF MS ES+) for $C_{29}H_{35}O_3S_2^+$ (MH+) calcd. 495.2028, found 495.2030.

Example 77: Methyl (2E)-3-{4-[5-(adamantan-1-yl)-2-hydroxybenzoyl]phenyl}prop-2-enoate (a) [5-(Adamantan-1-yl)-2-hydroxyphenyl](4-iodophenyl)methanone

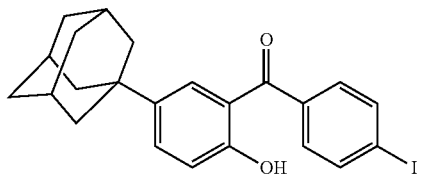 [SMILES: O=C(c1ccc(I)cc1)c1cc(C23CC4CC(CC(C4)C2)C3)ccc1O]

The compound was obtained following the procedure used for Example 48 using example 69 (c). After work-up, the crude product was purified by chromatography and recrystallized from EtOAc to yield example 77 (a) as a yellow solid, 1.09 g (21%). M. p. 186-187° C.; R$_f$=0.50 (5% EtOAc:cyclohexane). $^1$H NMR (400 MHz, CDCl$_3$) δ 11.72 (s, 1H), 7.89 (d, J=8.4 Hz, 2H), 7.57 (dd, J=8.8, 2.4 Hz, 1H), 7.47 (d, J=2.4 Hz, 1H), 7.43 (d, J=8.4 Hz, 2H), 7.03 (d, J=8.8 Hz, 1H), 2.08 (s, 3H), 1.80 (s, 3H), 1.80 (s, 3H), 1.76 (s, 3H), 1.72 (s, 3H). $^{13}$C NMR (101 MHz, CDCl$_3$) δ 200.72, 161.24, 142.04, 137.76, 137.59, 134.05, 130.93, 129.17, 118.37, 118.24, 99.50, 43.25, 36.69, 35.68, 28.92. HRMS (TOF MS ES+) for $C_{23}H_{24}IO_2^+$ (MH+) calcd. 459.0821, found 459.0818.

(b) Methyl (2E)-3-{4-[5-(adamantan-1-yl)-2-hydroxybenzoyl]phenyl}prop-2-enoate

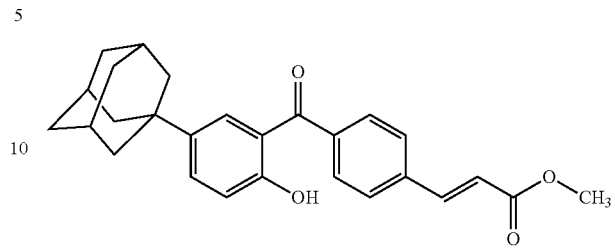

Prepared according to the procedure of 42 (c) to yield a yellow solid after purification by chromatography, 0.85 g (94%). M. p. 158-160° C.; R$_f$=0.45 (15% EtOAc:cyclohexane). $^1$H NMR (400 MHz, CDCl$_3$) δ 11.78 (s, 1H), 7.77 (d, J=16.1 Hz, 1H), 7.73 (d, J=8.3 Hz, 2H), 7.68 (d, J=8.3 Hz, 2H), 7.58 (dd, J=8.8, 2.4 Hz, 1H), 7.49 (d, J=2.4 Hz, 1H), 7.04 (d, J=8.8 Hz, 1H), 6.58 (d, J=16.0 Hz, 1H), 3.84 (s, 3H), 2.07 (s, 3H), 1.80 (s, 3H), 1.80 (s, 3H), 1.76 (d, J=13.4 Hz, 3H), 1.69 (d, J=12.0 Hz, 3H). $^{13}$C NMR (101 MHz, CDCl$_3$) δ 200.79, 167.10, 161.28, 143.54, 142.00, 139.54, 137.84, 134.01, 130.02, 129.30, 128.03, 120.34, 118.54, 118.21, 52.05, 43.25, 36.70, 35.68, 28.93. HRMS (TOF MS ES+) for $C_{27}H_{29}O_4^+$ (MH+) calcd. 417.2066, found 417.2068.

Example 78: Methyl 3-(4-{[5-(adamantan-1-yl)-2-hydroxyphenyl]methyl}phenyl)-propanoate

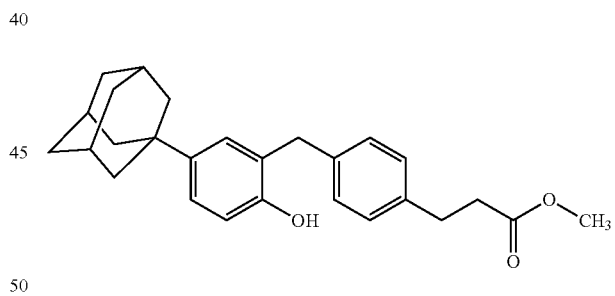

Example 77 was hydrogenated using the same procedure as for the formation of example 38 to provide 90 mg (82%) of a white solid. M, p. 102-103° C.; R$_f$=0.25 (10% EtOAc:cyclohexane). $^1$H NMR (400 MHz, CDCl$_3$) δ 7.19-7.01 (m, 6H), 6.73 (d, J=8.0 Hz, 1H), 4.53 (s, 1H), 3.96 (s, 2H), 3.66 (s, 3H), 2.91 (t, J=7.8 Hz, 2H), 2.60 (t, J=7.8 Hz, 2H), 2.07 (s, 3H), 1.87 (s, 6H), 1.75 (q, J=12.3 Hz, 6H). $^{13}$C NMR (101 MHz, CDCl$_3$) δ 173.56, 151.66, 144.26, 138.57, 138.17, 128.81, 128.67, 127.75, 126.23, 124.33, 115.51, 51.76, 43.56, 36.96, 36.72, 35.85, 35.71, 30.68, 29.16. HRMS (TOF MS ES+) for $C_{27}H_{33}O_3^+$ (MH+) calcd. 405.2430, found 405.2430.

Example 79: 3-(4-{[5-(adamantan-1-yl)-2-hydroxyphenyl]methyl}phenyl)propanoic Acid

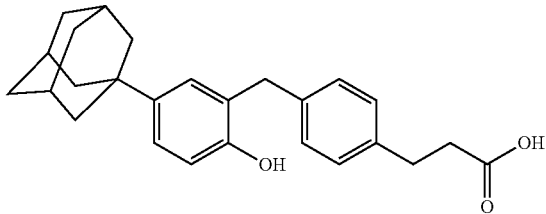 [SMILES: O=C(O)CCc1ccc(Cc2cc(C34CC5CC(CC(C5)C3)C4)ccc2O)cc1]

Example 78 was hydrolyzed following the same procedure as for the preparation of example 3 to obtain a yellow oil, 80 mg (89%). $R_f$=0.40 (50% EtOAc:cyclohexane). $^1$H NMR (400 MHz, CDCl$_3$) δ 7.13 (Aromatic, 6H), 6.73 (d, J=8.1 Hz, 1H), 3.96 (s, 2H), 2.92 (t, 7.7 Hz, 2H), 2.65 (t, J=7.7 Hz, 2H), 2.07 (s, 3H), 1.87 (s, 3H), 1.87 (s, 3H), 1.75 (q, J=12.3 Hz, 7H), $^{13}$C NMR (101 MHz, CDCl$_3$) δ 178.18, 151.63, 144.28, 138.32, 138.21, 128.86, 128.66, 127.77, 126.21, 124.34, 115.51, 43.56, 36.95, 36.71, 35.71, 30.34, 29.15. HRMS (TOF MS ES+) for $C_{52}H_{61}O_6^+$ (2MH+) calcd. 781.4468, found 781.4467.

Example 80: Characterization of Inhibitors of Cytochrome P450 26B1

9-cis-RA, acitretin, 4-[(5,6,7,8-tetrahydro-5,5,8,8-tetramethyl-2-naphthalenyl)carboxamido]benzoic acid (AM 580) and NADPH were purchased from Sigma-Aldrich (St. Louis, Mo.). (R)—N-[4-[2-ethyl-1-(1H-1,2,4-triazol-1-yl)butyl]phenyl]-2-benzo-thiazolamine (R115866, talarozole) and R116010 were gifts from Johnson & Johnson (Beerse, Belgium). 4-[(E)-2-(5,6,7,8-Tetrahydro-5,5,8,8-tetramethyl-2-naphthalenyl)-1-propenyl]benzoic acid (TTNPB), 6-[2-(3,4-Dihydro-4,4-dimethyl-2H-1-benzothiopyran-6-yl)ethynyl]-3-pyridinecarboxylic acid ethyl ester (Tazarotene), 4-[2-(5,6,7,8-Tetrahydro-5,5,8,8-tetramethyl-2-naphthalenyl)ethynyl)-benzoic acid (EC23), 4-[[(2,3-Dihydro-1,1,3,3-tetramethyl-2-oxo-1H-inden-5-yl)carbonyl]amino]benzoic acid (BMS753), 3-Fluoro-4-[[2-hydroxy-2-(5,5,8,8-tetramethyl-5,6,7,8,-tetrahydro-2-naphthalenyl)acetyl]amino]-benzoic acid (BMS961), and 4-[[(5,6,7,8-Tetrahydro-5,5,8,8-tetramethyl-2-naphthalenyl)amino]carbonyl]benzoic acid (AM80) and liarozole were purchased from Tocris Bioscience (Ellisville, Mo.). 4-OH-9-cis-RA was purchased from Toronto Research Chemicals Inc. (North York, ON, Canada). All solvents used were HPLC grade or higher and were purchased from EMD Chemicals (Gibbstown, N.J.), Mallinckrodt Baker, Inc. (Phillipsburg, N.J.), or Thermo Fisher Scientific (Waltham, Mass.).

Compound 1 was obtained in 73% yield by reacting 2-Bromo-1-(5,5,8,8-tetramethyl-5,6,7,8-tetrahydronaphthalen-2-yl)ethan-1-one with Methyl-4-hydroxybenzoate in the presence of K$_2$CO$_3$ in Methyl ethyl ketone under microwave conditions. Compound B was obtained after saponification of the methyl ester of compound A using sodium hydroxide. Reaction of B with hydroxylaminehydrochloride in MeOH under reflux yielded 2 isomers of the corresponding oximes, E-(E) and Z-(F). Compounds E and F yielded crystals of suitable quality for X-ray diffraction by slow evaporation of ethyl acetate/heptane solutions. These crystals were used to confirm the structures using X-ray data collected at 90 K, with Cu Kα radiation (λ=1.54178 Å) on a Bruker Kappa Apex-II diffractometer. Crystals of E are triclinic, space group P-1 with Z=2, R=0.036. Crystals of F are monoclinic, space group P2$_1$/c with Z=4. R=0.065. There is a conformational disorder of the six-membered ring carrying the four methyl groups. The Z-isomer was further hydrolyzed under basic conditions to provide the desired product D. Reduction of compound A using sodium borohydride followed by saponification yielded compound C. Tazarotene was hydrolyzed by reflux in K$_2$CO$_3$/MeOH to yield the corresponding acid in excellent yield.

Incubation Conditions for CYP26A1 and CYP26B1 and HPLC Analysis of RA Isomers and Metabolites CYP26A1 and CYP26B1 were expressed in Sf9 cells and used as microsomal fractions supplemented with rat P450 reductase expressed in *Escherichia coli* as described previously. Incubations were performed with 5 pmol of P450 (CYP26A1 or CYP26B1) and 10 pmol of P450 reductase. The purified rat reductase was added to CYP26A1 or CYP26B1 microsomes, and allowed to incorporate into the membrane for 10 min at room temperature. The final volume of each incubation sample was then brought to 1 ml by adding 100 mM potassium phosphate (KPi) buffer, pH 7.4, 9-cis-RA, and, when appropriate, inhibitor or solvent. Compounds were dissolved in methanol or dimethyl sulfoxide, and final solvent amounts in the incubations were kept at 1%. The samples were preincubated for 5 min at 37° C. before the reaction was initiated with NADPH (final concentration 1 mM). Incubation times were 1 minute and 5 minutes for CYP26A1 and CYP26B1 incubations respectively.

To determine whether the RA isomer 9-cis-RA is a substrate of CYP26B1, 9-cis-RA was incubated with CYP26B1. The formation of 9-cis-4-OH-RA by CYP26B1 was measured by HPLC as described previously for CYP26A1. Product formation was linear from 1 minute to 8 minutes. The $K_m$ and $V_{max}$ of 9-cis-RA hydroxylation by CYP26B1 was determined by incubating 8 different concentrations of 9-cis-RA between 50 nM and 1000 nM with CYP26B1. Five minutes after reactions were initiated with NADPH the reactions were quenched with 5 ml of ethyl acetate, acitretin was added as an internal standard, samples extracted, evaporated to dryness, reconstituted in methanol and analyzed by HPLC as described previously. A standard curve of 9-cis-4-OH-RA was used to quantify product formation by analysis of the peak area of the primary metabolite on an HPLC. The Michaelis-Menten equation was fit to the data using GraphPad Prism (GraphPad Software Inc., San Diego, Calif.), and the $K_m$ and $V_{max}$ values were obtained from this fit. 9-cis-RA was then used at 100 nM concentration as the substrate for subsequent assays of inhibitor potency.

CYP26A1 and CYP26B1 Inhibition Assay

Eighteen compounds were tested as potential inhibitors of CYP26A1 and CYP26B1. The formation of 9-cis-4-OH-RA metabolite was monitored and the percent activity remaining in the presence of the inhibitor in comparison to the solvent only control was quantified. For IC$_{50}$ determination, 6-8 concentrations of the inhibitor spanning below and above the predicted IC$_{50}$ were tested, and each concentration was analyzed in triplicate. The IC$_{50}$ values were determined by nonlinear regression using GraphPad Prism, according to equation 1:

$$100\% \cdot \frac{V_i}{V} = \left(\frac{V_i}{V}\right)_{min} \cdot 100\% + \frac{((V_i/V)_{max} - (V_i/V)_{min} \cdot 100\%)}{(1 + 10^{(I-logIC_{50})})} \quad (1)$$

in which 100%*(V$_i$/V) is the percentage of activity remaining at a given inhibitor (I) concentration, (V$_i$/V)$_{max}$*100% is the fitted maximum percentage activity remaining, and (V$_i$/V)$_{min}$*100% is the minimum percentage activity remaining. For compounds with IC$_{50}$ values less than 100 nM, all fits were corrected for inhibitor depletion, and the K$_d$ was determined using the Morrison equation as described previously according to equation 2:

$$[EI] = \frac{[E] + [I] + K_d - \sqrt{([E] + [I] + K_d)^2 - 4[E][I]}}{2} \quad (2)$$

in which K$_d$ is the affinity constant of the inhibitor, [I] is the concentration of inhibitor, [E] is the concentration of enzyme, and [EI] is the concentration of the enzyme-inhibitor complex.

Inhibition Assay for CYP2B8, CYP2C9 and CYP3A4

Compounds were assessed for inhibition (IC$_{50}$, n=2) of CYP2C8, CYP2C9 and CYP3A4 in pooled human liver microsomes using selective probe substrates at their previously determined K$_m$ values (CYP2C8: paclitaxel, 4 µM; CYP2C9: diclofenac, 5 µM; CYP3A4: midazolam, 0.5 µM). Incubations contained 0.1 mg/mL human liver microsomes, 3 mM MgCl2, probe substrate and various concentrations of inhibitor (12-point IC$_{50}$ curve) in 100 mM potassium phosphate buffer (pH 7.4). Concentrations of organic solvents were kept to <1% (v/v). All incubations were pre-incubated at 37° C. for 5 minutes prior to addition of 1 mM NADPH (final concentration). Incubations were stopped after 5 (CYP3A4) or 15 minutes (CYP2C8 and CYP2C9) with one volume (v/v) of ice-cold acetonitrile containing 0.1 µM tolbutamide as an internal standard. All samples were vortexed and centrifuged prior to LC-MS/MS analysis.

Detection of 6-hydroxypaclitaxel, 4-hydroxydiclofenac or 1'-hydroxymidazolam was achieved using a Gemini C18 2.0×30 mm 5 column (Phenomenex, Torrance, Calif.). Gradient elution (flow rate=500 µL/min) carried out using a mobile phase system consisting of (A) 5 mM ammonium formate with 0.1% formic acid and (B) acetonitrile with 0.1% formic acid. HPLC flow was diverted from the MS/MS system for the first 20 seconds to remove any non-volatile salts. Generic MS parameters included the curtain gas (10 arbitrary units), CAD gas (medium), ionspray voltage (4500 V), source temperature (450° C.) and ion source gas 1 and gas 2 (40 arbitrary units, each). Interface heaters were kept on for all analytes. Probe substrate mass transitions were identical to previously published methods. Briefly, the LC-MS/MS system utilized was comprised of an Applied Biosystems 4000 Q-Trap equipped with an electrospray ionization source (Applied Biosystems, Foster City, Calif.). The MS/MS system was coupled to two LC-20AD pumps with an in-line CBM-20A controller and DGU-20A$_5$ solvent degasser (shinadzu, Columbia, Md.) and a LEAP CTC HTS PAL autosampler equipped with a dual-solvent self-washing system (CTC Analytics, Carrboro, N.C.). An injection volume of 20 µL was used for all analyses. Standard curves and mass spectrometry data were fit using Analyst (version 1.4; Applied Biosystems, Foster City, Calif.). Analysis of IC$_{50}$ data was performed as described above for CYP26 inhibition assays.

CYP26B1 Homology Model.

The amino acid sequence of human CYP26B1 was obtained from the NCBI protein server (UniProtKB/Swiss-Prot Accession Number: Q9NR63) and used to construct a three-dimensional homology model of CYP26B1 using Prime (Schrodinger LLC, New York). The crystal structure of cyanobacterial CYP120A1 with atRA bound in the active site (pdb 2VE3) was used as the template for model based on sequence similarity between the two proteins (34% sequence identity; 54% positive sequence coverage). Protein structure alignment between the newly constructed homology model and a crystal structure of CYP3A4 with ketoconazole bound (pdb 2V0M) was used to position the heme prosthetic group within the active site of CYP26B1. The heme iron was ligated to Cys441 of CYP26B1 and the entire protein structure subject to energy minimization using the OPLS_2005 force field constraints within the MacroModel module (Schrodinger LLC, New York). Glide (Schrodinger LLC, New York) was then used to define a 14×14×14 Å receptor grid centered approximately 2 Å above the heme iron. Ramachandran plots and visual inspection were used to assess the structural plausibility of the homology model. Glide was also used to dock ligands within the defined active site of the CYP26B1 homology model using the ligand docking algorithm such that the center of each ligand was located within the defined grid. Prior to docking, ligands were prepared using the OPLS_2005 force field constraints within LigPrep (Schrodinger LLC, New York). Final docking poses were evaluated using GlideScore and eModel parameters.

Validation of CYP26B1 Inhibition Assay

To determine the inhibition of CYP26A1, a method was previously developed using recombinant CYP26A1 microsomes and 9-cis-RA as a substrate. To allow characterization of inhibition of CYP26B1, 9-cis-RA turnover by recombinant CYP26B1 was tested. 9-cis-RA was shown to be a substrate of CYP26B1 and metabolite formation was NADPH dependent (FIG. 1A). A single metabolite was detected from 9-cis-RA and the retention time of this metabolite was compared to synthetic 9-cis-4-OH-RA (FIG. 1A). The similar retention time suggests that the metabolite formed is 9-cis-4-OH-RA, The K$_m$ and V$_{max}$ for 9-cis-4-OH-RA formation by CYP26B1 were of 555 nM and 3.6 pmol/min/pmol P450, respectively resulting in an intrinsic clearance of 6.5 µL/min (FIG. 1B). Based on the K$_m$ value, all potential inhibitors of CYP26B1 were evaluated at a substrate concentration of 100 nM (concentration <<K$_m$ to increase sensitivity and decrease the dependence of IC$_{50}$ values on inhibition mechanism). 9-cis-RA was used as the probe substrate for inhibition screening instead of atRA since it has a 50-fold greater K$_m$ than atRA for CYP26B1 (555 nM versus 19 nM), allowing incubations under linear, steady-state conditions. In addition, only a single metabolite is formed from 9-cis-RA by CYP26B1 and no subsequent sequential metabolism was observed.

Figure 2:
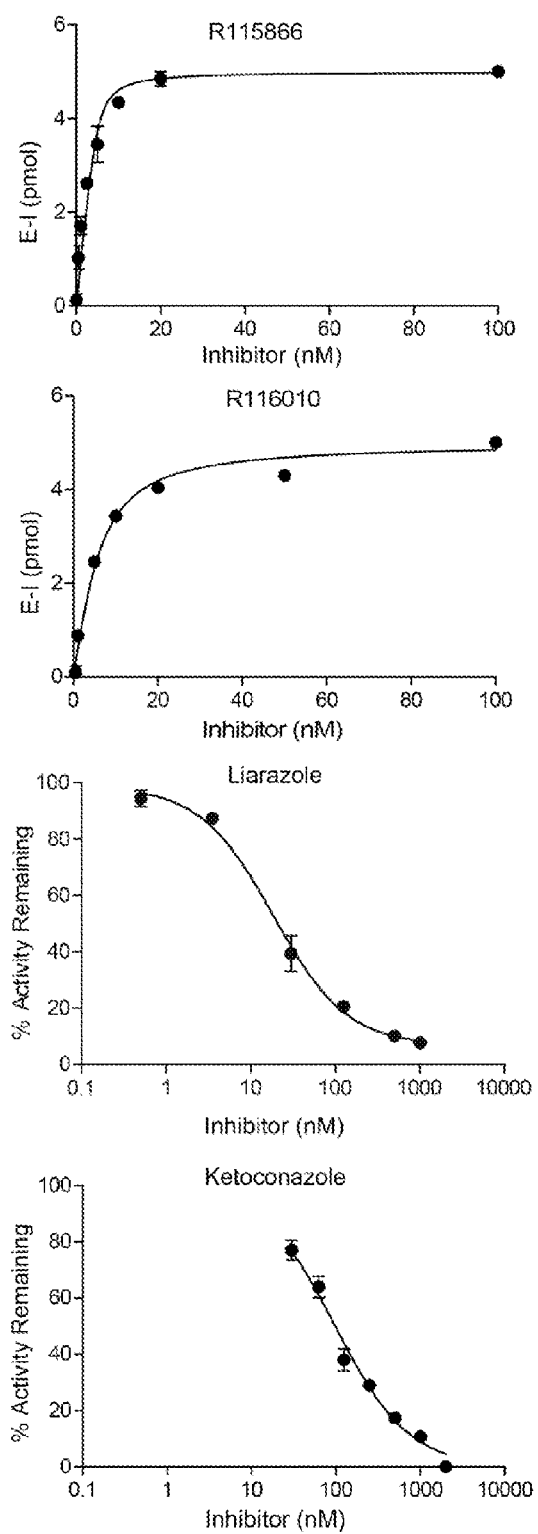
FIG. 2 illustrates azole $IC_{50}$'s and $K_d$'s with CYP26B1.

Characterization of CYP26 Isoform Selectivity of Known Azole Inhibitors of RA Metabolism The inhibition of CYP26A1 and CYP26B1 known azole inhibitors of atRA metabolism (liarozole, ketoconazole, Talarozole and R116010) was tested using recombinant CYP26A1 and CYP26B1 insect cell microsomes. The IC$_{50}$ values are summarized in Table 1 and FIG. 2.

TABLE 1

IC$_{50}$ values for CYP Panel with Azole inhibitors

| Structure | CYP26A1 IC$_{50}$ nM 95% CI | CYP26B1 IC$_{50}$ nM 95% CI | CYP26A1/ CYP26B1 | CYP2C8 IC$_{50}$ nM | CYP2C9 IC$_{50}$ nM | CYP3A4 IC$_{50}$ nM |
|---|---|---|---|---|---|---|
| Liarozole | 1900 1500-2300 | 18 13-27 | 106 | 480 | 1,630 | 10,000 |
| Ketoconazole | 660 370-1.2 | 140 34-560 | 5 | 1,560 | 2,570 | <20 |
| Talarozole (R115866) | 5.1[a,b] 3.4-6.8 | 0.46[a] 0.069-0.85 | 11 | 220 | 680 | 470 |
| R116010 | 4.3[a,b] 2.8-5.8 | 3.1[a] 2.5-3.7 | 1 | 1,760 | 5,760 | 120 |

[a] $K_s$ determined using Equation, Equation 2,
[b] data from Thatcher, et al. *Mol Pharmacol* 2011, 80 (2), 228-39.

All four azole inhibitors also inhibited at least one drug metabolizing P450 potently (Table 1), but no correlation was observed between inhibitory potency of either CYP26 enzyme and inhibition of specific drug metabolizing P450s. Liarozole inhibited CYP2C8 potently and was a weak inhibitor of CYP2C9 and CYP3A4. R116010 and ketoconazole were potent CYP3A4 inhibitors and weak (IC$_{50}$>1 µM) inhibitors of CYP2C9 and CYP2C8. Talarozole inhibited all three drug metabolizing P450 enzymes with nanomolar affinity.

In addition to inhibiting CYP26s, liarozole also inhibits other cytochromes involved in the biosynthetic pathways of testicular, ovarian and adrenal steroids (Berth-Jones J, et al. Treatment of psoriasis with oral liarozole: a dose-ranging study. *British Journal of Dermatology*. 2000; 143(6):1170-6; Bruynseels J, et al. R 75251, a new inhibitor of steroid biosynthesis. *The Prostate*. 1990; 16(4):345-57.) The results of a recent study do not support the assumption that pituitary compensation will compensate for the decrease on steroid biosynthesis induced by azole-containing RAMBA (Woerdeman; J, et al. In Young Men, a Moderate Inhibition of Testosterone Synthesis Capacity is Only Partly Compensated by Increased Activity of the Pituitary and the Hypothalamus. *Clin Endocrinol*. 2010; 72(3):76-80.)

Inhibition of CYP26B1 and CYP26A1 by RAR Agonists

Figure 3:
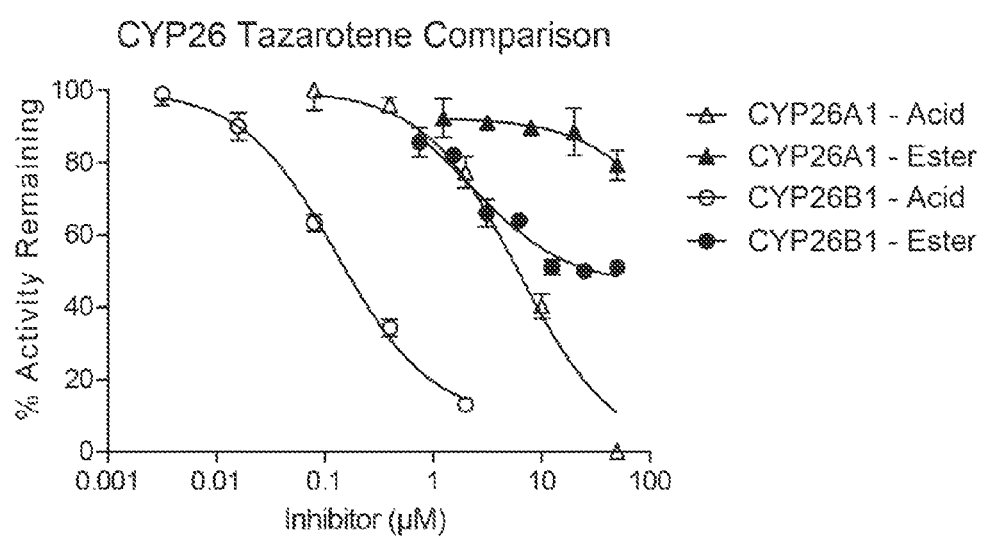
FIG. 3 illustrates tazarotenic acid and tazarotene $IC_{50}$'s with A1 and B1 ester versus acid for 2 and 5 and 1 and 4 with 26B1.
Figure 4:
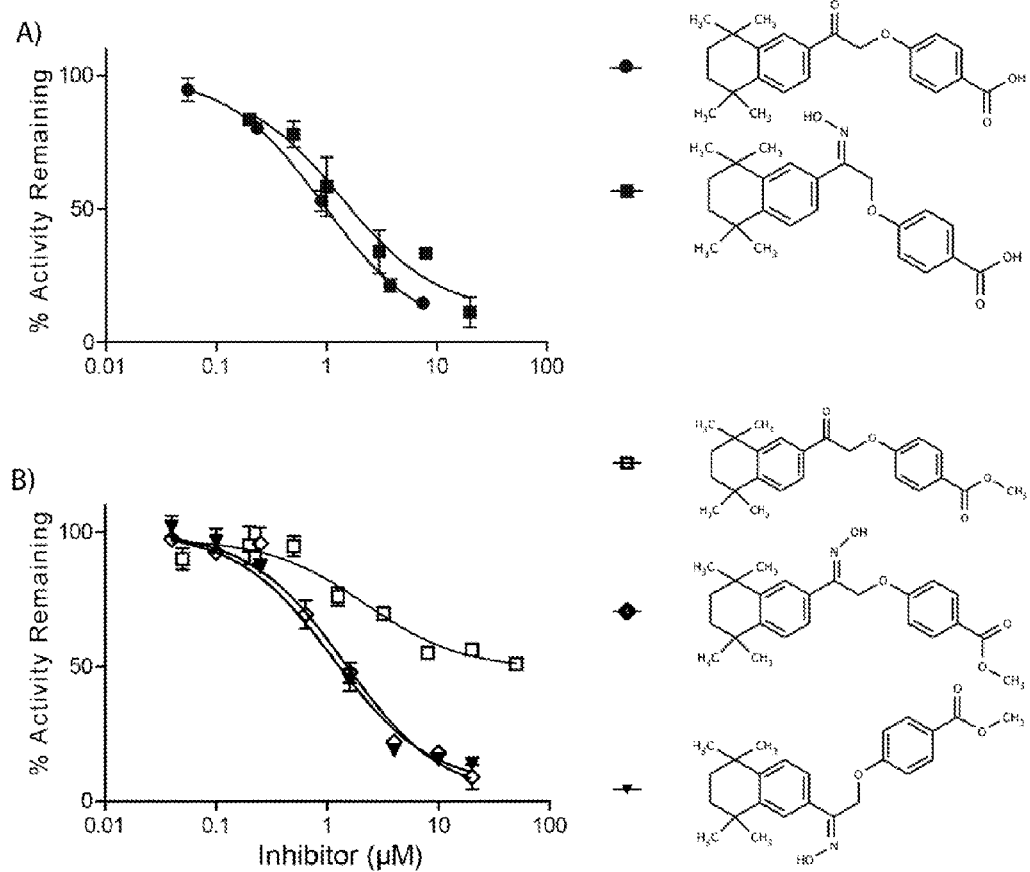
FIG. 4 shows the activity of NOH-containing compounds.

A series of commercially available RAR agonists were tested for CYP26A1 and CYP26B1 inhibition due to their similarity with atRA in polarity, size, charge and 3D space. Six new structural analogs of the tested RAR agonists were also synthesized to further evaluate the structural requirements of selective and potent CYP26A1 and CYP26B1 inhibition and possible hydrogen bonding interactions within CYP26A1 and CYP26B1 active site. The IC$_{50}$ values are summarized in Table 2 and FIGS. 3 and 4.

TABLE 2

IC$_{50}$ values for RAR agonists containing a carboxylic acid with CYP26A1 and CYP26B1

| Structure | CYP26A1 IC$_{50}$ μM | CYP26B1 IC$_{50}$ μM | CYP26A1/ CYP26B1 |
|---|---|---|---|
| AM80 | 12<br>8.1-18 | 6.6<br>2.3-19 | 1.8 |
| AM580 | 5.6<br>3.0-10 | 2.2<br>1.4-3.2 | 2.5 |
| TTNPB | 3.7$^a$<br>1.4-9.8 | 3.4<br>2.2-5.2 | 1.1 |
| Compound B | 4.0<br>2.5-6.3 | 0.93<br>0.61-1.4 | 4 |
| Compound C | 2.8<br>1.7-4.8 | 1.4<br>0.77-2.6 | 2 |

TABLE 2-continued

IC$_{50}$ values for RAR agonists containing a carboxylic acid with CYP26A1 and CYP26B1

| Structure | CYP26A1 IC$_{50}$ μM | CYP26B1 IC$_{50}$ μM | CYP26A1/ CYP26B1 |
|---|---|---|---|
| Compound D | 3.5 <br> 2.2-5.6 | 1.4 <br> 0.40-4.8 | 3 |
| BMS753 | 18 <br> 4.4-76 | 28 <br> 21-37 | 0.6 |
| BMS961 | 14 <br> 9.6-20 | 31 <br> 15-63 | 0.5 |
| Tazarotenic acid (DDBEP) | 6.1 <br> 3.2-12 | 0.13 <br> 0.090-0.19 | 47 |
| EC23 | 8.3 <br> 4.0-17 | 0.94 <br> 0.44-2.0 | 9 |

TABLE 2-continued

IC$_{50}$ values for RAR agonists containing a carboxylic acid with CYP26A1 and CYP26B1

| Structure | CYP26A1 IC$_{50}$ μM | CYP26B1 IC$_{50}$ μM | CYP26A1/ CYP26B1 |
|---|---|---|---|
| Tazarotene | ND$^a$ | 2.3$^b$ 1.0-5.3 | NA |
| Compound A | ND$^c$ | 2.1$^d$ 1.0-4.9 | |
| Compound E | 12 6.3-22 | 1.5 0.96-2.2 | 8 |
| Compound F | 8.5 4.8-15 | 1.1 0.70-1.8 | 7 |

$^a$Maximum 15% inhibition observed at 100 μM
$^b$Only partial inhibition obtained, maximum inhibition was 54%
$^c$Maximum 15% inhibition observed at 100 μM
$^d$Only partial inhibition obtained, maximum inhibition was 51%

The data shown here suggests that synthetic retinoids can bind to CYP26A1 and CYP26B1 but have variable potency as CYP26 inhibitors.

Example 81: Characterization of Inhibitors of Cytochrome P450 26A1

Compounds of the disclosure were tested as potential inhibitors of CYP26A1 and CYP26B1. The conditions for $IC_{50}$ experiments along with the methods of data analysis are the same as described in Example 80. The results are shown in Tables 3, 4, and 5.

TABLE 3

Inhibitors for CYP26A1 selective inhibition

| Inhibitor | CYP26A1 | CYP26B1 |
|---|---|---|
| 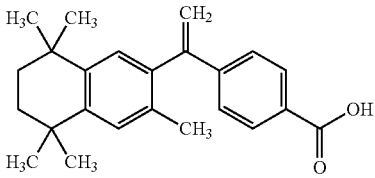 Bexarotene | 12.3 | 4.0 |
| 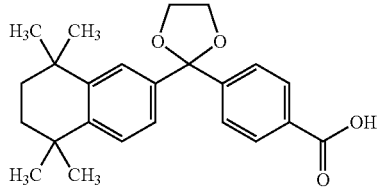 SR11237 | 3.3 | 14.2 |
| 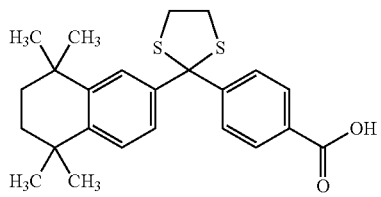 MM11253 | 0.061 | 1.03 |

TABLE 4

Acidic compounds designed to target CYP26A1 selective inhibition

| Inhibitor | CYP26A1 | CYP26B1 |
|---|---|---|
| 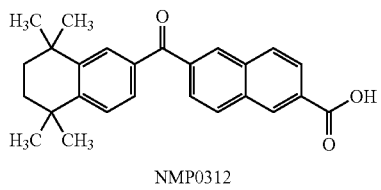 NMP0302 | >25 | >25 |
| 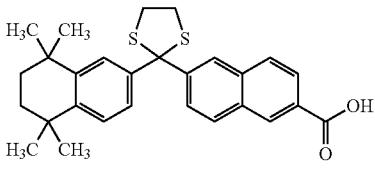 NMP0306 | 7.78 | 12.6 |
| 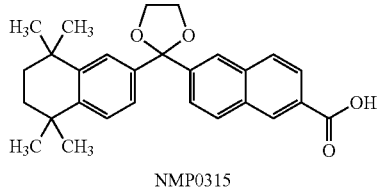 NMP0305 | 1.28 | 1.09 |
| 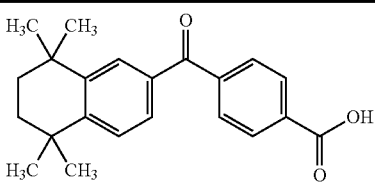 NMP0312 | 1.63 | 0.53 |
| 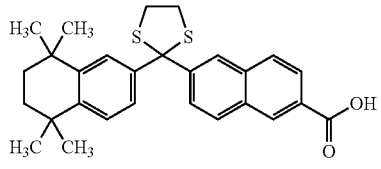 NMP0315 | 0.109 | 1.03 |
|  NMP0313 | 0.061 | 1.03 |

TABLE 5
Compound of the disclosure as inhibitors of CYP26A1 and CYP26B1
| Structure | CYP26A1 μM | CYP26B1 μM | CYP3A4 |
|---|---|---|---|
| 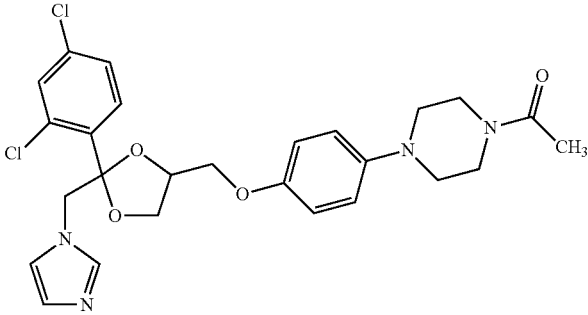<br>Ketoconazole | 0.66 | 0.14 | |
| 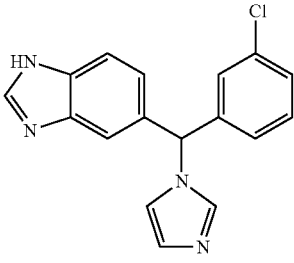<br>Liarozole | 1.9 | 0.018 | |
| 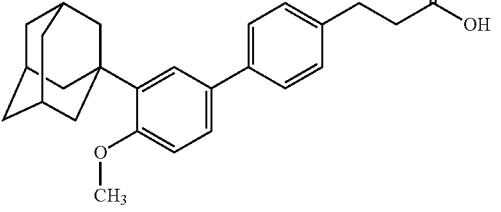<br>Example 30 | | 0.516 | |
| 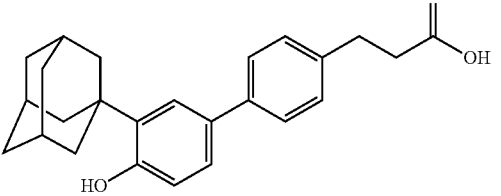<br>Example 31 | 0.314 | 0.302 | |
| 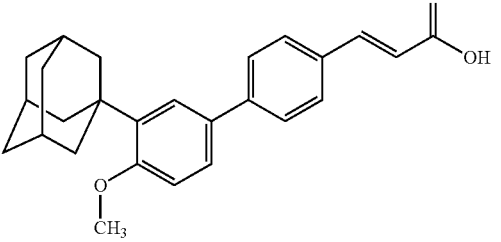<br>Example 33 | >25 | >25 | |

TABLE 5-continued

Compound of the disclosure as inhibitors of CYP26A1 and CYP26B1

| Structure | CYP26A1 μM | CYP26B1 μM | CYP3A4 |
|---|---|---|---|
| Example 36 | 0.729 | 0.087 | |
| Example 37 | 0.232 | 0.095 | |
| Example 38 | 0.051 | 0.051 | 24 |
| Example 39 | 1.752 | 0.108 | 2.4 |
| Example 44 | 0.34 | 14.5 | 50 |

TABLE 5-continued

Compound of the disclosure as inhibitors of CYP26A1 and CYP26B1

| Structure | CYP26A1 μM | CYP26B1 μM | CYP3A4 |
|---|---|---|---|
| Example 49 | 0.006 | 4.4 | |
| Example 52 | 0.269 | 0.684 | |
| Example 54 | >10 | 1.66 | |
| (structure) | 0.239 | >10 | |
| Talarozole (R115866) | 0.0051 | 4.60E-04 | |

The earliest compounds designed to inhibit the metabolism of atRA, ketoconazole, liarozole and talarozole, all were shown to increase the concentration of atRA in vivo in animal models, which agrees with the microsomal inhibition of atRA metabolism that was found in both our recombinantly expressed protein prepared as microsomes, as well as previous reports containing microsomal extracts that had been made from cell lines induced to express CYP26A1. In many of the experiments that have taken place to induce apoptosis or inhibit metabolism with small molecules, the consideration for the presence of both enzymes, CYP26A1 and CYP26B1, is not taken into consideration. There are also many tissues that have been profiled for protein content and found to have equal amounts of either isozyme. The repetition of two enzymes that have very similar functions is an interesting phenomenon and selective inhibition of either enzyme will help to characterize whether there are any differences in function between the two proteins, or whether they are redundant in function in an adult.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of the formula (I):

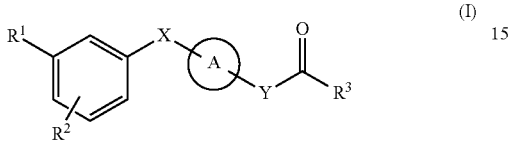

or a pharmaceutically acceptable salt thereof, wherein

A represents phenyl optionally substituted with one or two groups that are each independently halogen, cyano, nitro, $C_{1-6}$ alkyl, $C_{1-6}$ haloalkyl, —$NH_2$, —$NH(C_1-C_6$ alkyl), —$N(C_1-C_6$ alkyl)$_2$, —OH, $C_1-C_6$ alkoxy, and $C_1-C_6$ haloalkoxy;

X is —$CH_2$—, —$CHR^5$—, —$NR^4$—, —O—, —S—, —SO—, —$SO_2$—, —C(O)—, or —$C(NR^4)$—, or X is of formula

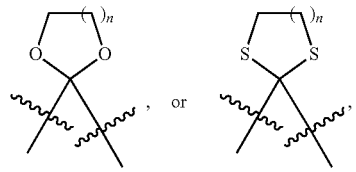

wherein
each n is independently 1, 2, or 3;
each $R^4$ is independently hydrogen or $C_{1-6}$ alkyl;
$R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl;
Y is $C_{1-6}$ alkylene or $C_{2-6}$ alkenylene moiety;
$R^1$ is $C_{3-12}$ cycloalkyl optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl;
$R^2$ is halogen, $C_{1-6}$ alkyl, or —$OR^8$, where $R^8$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl; and $R^3$ is hydrogen, $C_{1-6}$ alkyl, $C_{1-6}$ haloalkyl, —OR, —SR, or —$NR_2$,
and each R is independently hydrogen, $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^0$, —$SR^0$, —$N(R^0)_2$, —$C(O)R^0$, —$C(O)OR^0$, —$C(O)N(R^0)_2$, —$S(O)_2R^0$, —$OC(O)R^0$, —$OC(O)OR^0$, —$OC(O)N(R^0)_2$, —$N(R^0)C(O)R^0$, —$N(R^0)C(O)OR^0$, or —$N(R^0)C(O)N(R^0)_2$, wherein each $R^0$ is independently hydrogen or $C_{1-6}$ alkyl.

2. The compound according to claim 1, wherein
X is —$CH_2$—, —$CHR^5$—, —$NR^4$—, —O—, —S—, —SO—, —$SO_2$—, —C(O)—, —$C(NR^4)$—, wherein each $R^4$ is independently hydrogen or $C_{1-6}$ alkyl; and
$R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl.

3. The compound according to claim 1, wherein
X is —$CH_2$— or —$CHR^5$—, wherein $R^5$ is independently hydrogen, $C_{1-6}$ alkyl, or —$OR^6$, where $R^6$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl.

4. The A compound according to claim 3, wherein X is —$CH_2$—.

5. The compound according to claim 1, wherein
X is —$NR^4$—, —O—, —S—, —SO—, —$SO_2$—, —C(O)—, —$C(NR^4)$—, wherein each $R^4$ is independently hydrogen or $C_{1-6}$ alkyl.

6. The compound according to claim 5, wherein X is —O—, —S—, —SO—, —$SO_2$—, —C(O)—, or —$C(NR^4)$—.

7. The compound according to claim 5, wherein X is —O—, —S—, —SO—, or —$SO_2$—.

8. The compound according to claim 5, wherein X is —O—.

9. The compound according to claim 5, wherein X is —S—, —SO—, or —$SO_2$—.

10. The compound according to claim 8, wherein X is —C(O)—.

11. The compound according to claim 1, wherein X is of formula

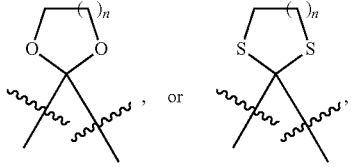

and each n is independently 1 or 2.

12. The compound according to claim 11, wherein each n is independently 1.

13. The compound according to claim 1, wherein X is —$CH_2$—, —NH—, —S—, —$SO_2$—, —C(O)—,

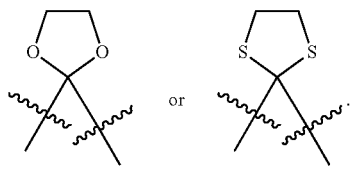 [SMILES: *C1(*)OCCO1 ; *C1(*)SCCS1]

14. The compound according to claim 1, wherein X is —CH$_2$—, —NH—, —S—, —SO$_2$—, —C(O)—,

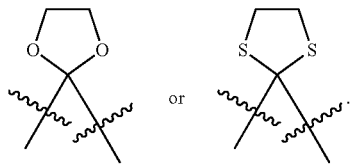 [SMILES: *C1(*)OCCO1 ; *C1(*)SCCS1]

15. The compound according to claim 1, wherein Y is C$_{1-4}$ alkylene or C$_{2-4}$ alkenylene.

16. The compound according to claim 1, wherein Y is C$_{1-4}$ alkylene.

17. The compound according to claim 16, wherein Y is methylene, ethylene, or propylene.

18. The compound according to claim 17, wherein Y is methylene or ethylene.

19. The compound according to claim 1, wherein Y is C$_{2-4}$ alkenylene.

20. The compound according to claim 19, wherein Y is —CH=CH—, —CH$_2$CH=CH—, or —CH=CHCH$_2$—.

21. The compound according to claim 1, wherein Y is methylene, ethylene, or —CH=CH—.

22. The compound according to claim 1, wherein R$^3$ is hydrogen, C$_{1-6}$ alkyl, —OR, or —NR$_2$,
and each R is independently hydrogen, C$_{1-6}$ alkyl, C$_{2-6}$ alkenyl, C$_{1-6}$ haloalkyl, C$_{3-12}$ cycloalkyl, heterocyclyl, aryl, arylC$_{1-6}$ alkyl, heteroaryl, or heteroarylC$_{1-6}$ alkyl, wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R$^0$, —N(R$^0$)C(O)OR$^0$, or —N(R$^0$)C(O)N(R$^0$)$_2$, wherein each R$^0$ is independently hydrogen or C$_{1-6}$ alkyl.

23. The compound according to claim 22, wherein R$^3$ is hydrogen or C$_{1-6}$ alkyl.

24. The compound according to claim 23, wherein R$^3$ is hydrogen.

25. The compound according to claim 23, wherein R$^3$ is C$_{1-6}$ alkyl.

26. The compound according to claim 22, wherein R$^3$ is —NR$_2$.

27. The compound according to claim 26, wherein each R is independently hydrogen or C$_{1-6}$ alkyl optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R$^0$, —N(R$^0$)C(O)OR$^0$, or —N(R$^0$)C(O)N(R$^0$)$_2$, wherein each R$^0$ is independently hydrogen or C$_{1-6}$ alkyl.

28. The compound according to claim 22, wherein R$^3$ is —OR.

29. The compound according to claim 28, wherein R is hydrogen, C$_{1-6}$ alkyl, C$_{2-6}$ alkenyl, C$_{1-6}$ haloalkyl, C$_{3-12}$ cycloalkyl, heterocyclyl, aryl, arylC$_{1-6}$ alkyl, heteroaryl, or heteroarylC$_{1-6}$ alkyl, wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, and —S(O)$_2$R$^0$, wherein each R$^0$ is independently hydrogen or C$_{1-6}$ alkyl.

30. The compound according to claim 28, wherein R is hydrogen, C$_{1-6}$ alkyl, C$_{1-6}$ haloalkyl, C$_{3-12}$ cycloalkyl, aryl, arylC$_{1-6}$ alkyl, heteroaryl, or heteroarylC$_{1-6}$ alkyl, wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, and —S(O)$_2$R$^0$, wherein each R$^0$ is independently hydrogen or C$_{1-6}$ alkyl.

31. The compound according to claim 28, wherein R is hydrogen, C$_{1-6}$ alkyl, C$_{1-6}$ haloalkyl, or arylC$_{1-6}$ alkyl, wherein the alkyl and arylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, and —S(O)$_2$R$^0$, wherein each R$^0$ is independently hydrogen or C$_{1-6}$ alkyl.

32. The compound according to claim 28, wherein R is hydrogen or C$_{1-6}$ alkyl.

33. The compound according to claim 32, wherein R is hydrogen.

34. The compound according to claim 32, wherein R is C$_{1-4}$ alkyl.

35. The compound according to claim 32, wherein R is hydrogen, methyl, ethyl, propyl, or butyl.

36. The compound according to claim 28, wherein R is arylC$_{1-6}$ alkyl.

37. The compound according to claim 36, wherein R is benzyl.

38. The compound according to claim 1, wherein R$^1$ is unsubstituted C$_{3-12}$ cycloalkyl.

39. The compound according to claim 1, wherein R$^1$ is adamantyl.

40. The compound according to claim 1, wherein R$^2$ is halogen, C$_{1-6}$ alkyl, or —OR$^8$.

41. The compound according to claim 40, wherein R$^2$ is halogen or C$_{1-6}$ alkyl.

42. The compound according to claim 36, wherein R$^2$ is —OR$^8$.

43. The compound according to claim 42, wherein R$^8$ is selected from the group consisting of hydrogen, C$_{1-6}$ alkyl, C$_{3-12}$ cycloalkyl, heterocyclyl, aryl, arylC$_{1-6}$ alkyl, heteroaryl, or heteroarylC$_{1-6}$ alkyl, wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^7$, —SR$^7$, —N(R$^7$)$_2$, —C(O)R$^7$, —C(O)OR$^7$, —C(O)N(R$^7$)$_2$, —S(O)$_2$R$^7$, —OC(O)R$^7$, —OC(O)OR$^7$, —OC(O)N(R$^7$)$_2$, —N(R$^7$)C(O)R$^7$, —N(R$^7$)C(O)OR$^7$, or —N(R$^7$)C(O)N(R$^7$)$_2$, wherein each R$^7$ is independently hydrogen or C$_{1-6}$ alkyl.

44. The compound according to claim 42, wherein R$^8$ is selected from the group consisting of hydrogen, C$_{1-6}$ alkyl, or arylC$_{1-6}$ alkyl, wherein the alkyl and arylalkyl are optionally substituted with one, two, three, or four groups that are each independently halogen, cyano, nitro, $C_{1-6}$ alkyl, $C_{1-6}$ haloalkyl, —$OR^7$, —$SR^7$, —$N(R^7)_2$, —$C(O)R^7$, —$C(O)OR^7$, —$C(O)N(R^7)_2$, —$S(O)_2R^7$, —$OC(O)R^7$, —$OC(O)OR^7$, —$OC(O)N(R^7)_2$, —$N(R^7)C(O)R^7$, —$N(R^7)C(O)OR^7$, or —$N(R^7)C(O)N(R^7)_2$, wherein each $R^7$ is independently hydrogen or $C_{1-6}$ alkyl.

45. The compound according to claim 42, wherein $R^8$ is of hydrogen or $C_{1-6}$ alkyl.

46. The compound according to claim 42, wherein $R^8$ is of hydrogen.

47. The compound according to claim 42, wherein $R^8$ is $C_{1-6}$ alkyl.

48. The compound according to claim 42, wherein $R^8$ is of hydrogen or methyl.

49. The compound according to claim 42, wherein $R^8$ is of aryl$C_{1-6}$ alkyl.

50. The compound according to claim 42, wherein $R^8$ is benzyl.

51. The compound according to claim 42, wherein $R^8$ is of hydrogen, $C_{1-6}$ alkyl, or benzyl.

52. A compound according to claim 1, which is:
Methyl 2-(4-{[3-(adamantan-1-yl)-4-methoxyphenyl]sulfanyl}phenyl)acetate;
Butyl 2-(4-{[3-(adamantan-1-yl)-4-methoxyphenyl]sulfanyl}phenyl)acetate;
2-(4-{[3-(adamantan-1-yl)-4-methoxyphenyl]sulfanyl}phenyl)acetic acid;
Methyl 2-(3-{[3-(adamantan-1-yl)-4-methoxyphenyl]sulfanyl}phenyl)acetate;
Butyl 2-(3-{[3-(adamantan-1-yl)-4-methoxyphenyl]sulfanyl}phenyl)acetate;
2-(3-{[3-(Adamantan-1-yl)-4-methoxyphenyl]sulfanyl}phenyl)acetic acid;
Methyl 2-(4-{[3-(adamantan-1-yl)-4-methoxybenzene]sulfonyl}phenyl)acetate;
Butyl 2-(4-{[3-(adamantan-1-yl)-4-methoxybenzene]sulfonyl}phenyl)acetate;
2-(4-{[3-(adamantan-1-yl)-4-methoxybenzene]sulfonyl}phenyl)acetic acid;
Methyl 2-(3-{[3-(adamantan-1-yl)-4-methoxybenzene]sulfonyl}phenyl)acetate;
Butyl 2-(3-{[3-(adamantan-1-yl)-4-methoxybenzene]sulfonyl}phenyl)acetate;
2-(3-{[3-(adamantan-1-yl)-4-methoxybenzene]sulfonyl}phenyl)acetic acid;
Ethyl 3-{4-[3-(adamantan-1-yl)-4-methoxyphenyl]phenyl}propanoate;
3-{4-[3-(adamantan-1-yl)-4-methoxyphenyl]phenyl}propanoic acid;
3-{4-[3-(adamantan-1-yl)-4-hydroxyphenyl]phenyl}propanoic acid;
Benzyl (2E)-3-{4-[3-(adamantan-1-yl)-4-methoxyphenyl]phenyl}prop-2-enoate;
2(E)-3-{4-[3-(adamantan-1-yl)-4-methoxyphenyl]phenyl}prop-2-enoic acid;
(2E)-3-{4-[3-(adamantan-1-yl)-4-hydroxyphenyl]phenyl}prop-2-enoic acid;
Benzyl (2E)-3-(4-{[3-(adamantan-1-yl)-4-methoxyphenyl]amino}phenyl)prop-2-enoate;
(2E)-3-(4-{[3-(adamantan-1-yl)-4-methoxyphenyl]amino}phenyl)prop-2-enoic acid;
(2E)-3-(4-{[3-(adamantan-1-yl)-4-hydroxyphenyl]amino}phenyl)prop-2-enoic acid;
3-(4-{[3-(adamantan-1-yl)-4-methoxyphenyl]amino}phenyl)propanoic acid;
3-(4-{[3-(adamantan-1-yl)-4-hydroxyphenyl]amino}phenyl)propanoic acid;
methyl (2E)-3-{4-[5-(adamantan-1-yl)-2-methoxybenzoyl]phenyl}prop-2-enoate;
Methyl (2E)-3-(4-{2-[5-(adamantan-1-yl)-2-methoxyphenyl]-1,3-dioxolan-2-yl}phenyl)prop-2-enoate;
(2E)-3-(4-{2-[5-(adamantan-1-yl)-2-methoxyphenyl]-1,3-dioxolan-2-yl}phenyl)prop-2-enoic acid;
3-(4-{2-[5-(adamantan-1-yl)-2-methoxyphenyl]-1,3-dioxolan-2-yl}phenyl)propanoic acid;
Methyl 3-(4-{2-[5-(adamantan-1-yl)-2-methoxyphenyl]-1,3-dioxolan-2-yl}phenyl)propanoate;
Methyl 3-{4-[5-(adamantan-1-yl)-2-methoxybenzoyl]phenyl}propanoate;
Methyl 3-(4-{2-[5-(adamantan-1-yl)-2-methoxyphenyl]-1,3-dithiolan-2-yl}phenyl)propanoate;
3-(4-{2-[5-(adamantan-1-yl)-2-methoxyphenyl]-1,3-dithiolan-2-yl}phenyl)propanoic acid;
Methyl (2E)-3-{4-[5-(adamantan-1-yl)-2-hydroxybenzoyl]phenyl}prop-2-enoate;
Methyl 3-(4-{[5-(adamantan-1-yl)-2-hydroxyphenyl]methyl}phenyl)propanoate;
3-(4-{[5-(adamantan-1-yl)-2-hydroxyphenyl]methyl}phenyl)propanoic acid; or
pharmaceutically acceptable salts thereof.

53. A pharmaceutical composition comprising one or more of compounds according to claim 1 and a pharmaceutically acceptable carrier, diluent, or excipient.

* * * * *